(12) United States Patent
Rachet et al.

(10) Patent No.: US 11,828,710 B2
(45) Date of Patent: Nov. 28, 2023

(54) SYSTEMS AND METHODS FOR IN-OPERATING-THEATRE IMAGING OF FRESH TISSUE RESECTED DURING SURGERY FOR PATHOLOGY ASSESSMENT

(71) Applicant: SamanTree Medical SA, Lausanne (CH)

(72) Inventors: Bastien Rachet, Lausanne (CH); Davor Kosanic, Lausanne (CH); Etienne Shaffer, Pailly (CH)

(73) Assignee: SamanTree Medical SA, Lausanne (CH)

( * ) Notice: Subject to any disclaimer, the term of this patent is extended or adjusted under 35 U.S.C. 154(b) by 0 days.

(21) Appl. No.: 18/103,069

(22) Filed: Jan. 30, 2023

(65) Prior Publication Data

US 2023/0175969 A1 Jun. 8, 2023

Related U.S. Application Data

(63) Continuation of application No. 16/054,681, filed on Aug. 3, 2018, now Pat. No. 11,609,186, which is a (Continued)

(51) Int. Cl.
*G02B 21/00* (2006.01)
*G01N 21/77* (2006.01)
(Continued)

(52) U.S. Cl.
CPC ......... *G01N 21/77* (2013.01); *G01N 21/6428* (2013.01); *G01N 21/6458* (2013.01);
(Continued)

(58) Field of Classification Search
CPC .................................................. G02B 21/0076
See application file for complete search history.

(56) References Cited

U.S. PATENT DOCUMENTS

| | | |
|---|---|---|
| 3,814,504 A | 6/1974 | Brady et al. |
| 4,927,254 A | 5/1990 | Kino et al. |

(Continued)

FOREIGN PATENT DOCUMENTS

| | | |
|---|---|---|
| DE | 19632594 A1 | 2/1998 |
| DE | 19729245 C1 | 5/1999 |

(Continued)

OTHER PUBLICATIONS

Afzal, R. S. et al., Optical Tweezers Using a Diode Laser, Review of Scientific Instruments, IAP 63(4):2157-2163 (1992).
(Continued)

*Primary Examiner* — Jonathan M Hurst
(74) *Attorney, Agent, or Firm* — Choate, Hall & Stewart LLP; Michael D. Schmitt

(57) ABSTRACT

The disclosed technology brings histopathology into the operating theatre, to enable real-time intra-operative digital pathology. The disclosed technology utilizes confocal imaging devices image, in the operating theatre, "optical slices" of fresh tissue—without the need to physically slice and otherwise process the resected tissue as required by frozen section analysis (FSA). The disclosed technology, in certain embodiments, includes a simple, operating-table-side digital histology scanner, with the capability of rapidly scanning all outer margins of a tissue sample (e.g., resection lump, removed tissue mass). Using point-scanning microscopy technology, the disclosed technology, in certain embodiments, precisely scans a thin "optical section" of the resected tissue, and sends the digital image to a pathologist rather than the real tissue, thereby providing the pathologist with the opportunity to analyze the tissue intra-operatively. Thus, the disclosed technology provides digital images with similar information content as FSA, but faster and without destroying the tissue sample itself.

20 Claims, 40 Drawing Sheets

Related U.S. Application Data continuation of application No. 15/200,126, filed on Jul. 1, 2016, now Pat. No. 10,094,784, which is a continuation of application No. 15/087,601, filed on Mar. 31, 2016, now Pat. No. 10,088,427.

(60) Provisional application No. 62/141,223, filed on Mar. 31, 2015.

(51) Int. Cl.
  *G02B 21/26* (2006.01)
  *G02B 21/34* (2006.01)
  *G02B 21/36* (2006.01)
  *G01N 21/64* (2006.01)
  *G01N 33/483* (2006.01)
  *G02B 21/16* (2006.01)
  *G02B 21/24* (2006.01)

(52) U.S. Cl.
  CPC ....... *G01N 33/4833* (2013.01); *G02B 21/004* (2013.01); *G02B 21/0032* (2013.01); *G02B 21/0076* (2013.01); *G02B 21/0088* (2013.01); *G02B 21/16* (2013.01); *G02B 21/26* (2013.01); *G02B 21/34* (2013.01); *G02B 21/361* (2013.01); *G01N 2021/6439* (2013.01); *G01N 2021/6463* (2013.01); *G01N 2021/7786* (2013.01); *G01N 2201/068* (2013.01); *G01N 2201/0633* (2013.01); *G02B 21/0012* (2013.01); *G02B 21/0044* (2013.01); *G02B 21/24* (2013.01)

(56) References Cited

U.S. PATENT DOCUMENTS

| | | |
|---|---|---|
| 5,161,053 A | 11/1992 | Dabbs |
| 5,257,128 A | 10/1993 | Diller et al. |
| 5,463,223 A | 10/1995 | Wong et al. |
| 5,557,452 A | 9/1996 | Harris |
| 5,580,827 A | 12/1996 | Akamine |
| 5,689,109 A | 11/1997 | Schutze |
| 6,052,224 A | 4/2000 | Richardson |
| 6,133,986 A | 10/2000 | Johnson |
| 6,185,030 B1 | 2/2001 | Overbeck |
| 6,335,824 B1 | 1/2002 | Overbeck |
| 6,348,999 B1 | 2/2002 | Summersgill et al. |
| 6,392,752 B1 | 5/2002 | Johnson |
| 6,424,852 B1 | 7/2002 | Zavislan |
| 6,937,886 B2 | 8/2005 | Zavislan |
| 7,193,782 B2 | 3/2007 | Menon et al. |
| 7,225,010 B1 | 5/2007 | Zavislan |
| 7,285,089 B2 | 10/2007 | Viellerobe et al. |
| 7,312,919 B2 | 12/2007 | Overbeck |
| 7,628,865 B2 | 12/2009 | Singh |
| 7,706,043 B2 | 4/2010 | Uhl et al. |
| 7,759,635 B2 | 7/2010 | Boer et al. |
| 7,968,839 B2 | 6/2011 | Merenda et al. |
| 8,121,670 B2 | 2/2012 | Zavislan |
| 8,553,337 B2 | 10/2013 | Webb et al. |
| 8,606,343 B2 | 12/2013 | Zavislan |
| 8,686,376 B2 | 4/2014 | Wimberger-Friedl et al. |
| 9,075,227 B2 | 7/2015 | Rachet et al. |
| 9,333,036 B2 | 5/2016 | Ben-Yakar et al. |
| 9,563,044 B2 | 2/2017 | Kosanic et al. |
| 9,677,869 B2 | 6/2017 | Berkeley et al. |
| 9,678,323 B2 | 6/2017 | Orth et al. |
| 10,088,427 B2 | 10/2018 | Rachet et al. |
| 10,539,776 B2 | 1/2020 | Shaffer et al. |
| 10,816,788 B2 | 10/2020 | Shaffer et al. |
| 11,181,728 B2 | 11/2021 | Shaffer et al. |
| 2001/0048467 A1 | 12/2001 | Fiedler |
| 2002/0088858 A1 | 7/2002 | Tanaami et al. |
| 2003/0032204 A1 | 2/2003 | Walt et al. |
| 2003/0147083 A1 | 8/2003 | Hill |
| 2004/0012853 A1 | 1/2004 | Garcia et al. |
| 2004/0125370 A1 | 7/2004 | Montagu |
| 2004/0204651 A1 | 10/2004 | Freeman et al. |
| 2004/0256542 A1 | 12/2004 | Okazaki |
| 2004/0264856 A1 | 12/2004 | Farr |
| 2005/0014201 A1 | 1/2005 | Deuthsch |
| 2005/0018199 A1 | 1/2005 | LeBlanc |
| 2005/0098717 A1 | 5/2005 | Grier et al. |
| 2005/0146794 A1 | 7/2005 | Menon et al. |
| 2006/0077536 A1 | 4/2006 | Bromage et al. |
| 2006/0121298 A1 | 6/2006 | Wittke et al. |
| 2006/0163463 A1 | 7/2006 | Grier |
| 2007/0235640 A1 | 10/2007 | Gruber et al. |
| 2007/0251543 A1 | 11/2007 | Singh |
| 2008/0030742 A1 | 2/2008 | Hill |
| 2008/0121790 A1 | 5/2008 | Grier |
| 2009/0028407 A1 | 1/2009 | Seibel et al. |
| 2009/0190221 A1 | 7/2009 | Boer et al. |
| 2009/0225409 A1 | 9/2009 | Ilev et al. |
| 2010/0200739 A1 | 8/2010 | Anderson et al. |
| 2010/0207016 A1 | 8/2010 | McBride et al. |
| 2011/0116694 A1 | 5/2011 | Gareau |
| 2011/0211104 A1 | 9/2011 | Hendriks |
| 2011/0300490 A1 | 12/2011 | Rachet et al. |
| 2012/0133757 A1 | 5/2012 | Thomas et al. |
| 2013/0211391 A1 | 8/2013 | BenYakar et al. |
| 2014/0193892 A1 | 7/2014 | Mohan et al. |
| 2015/0085289 A1 | 3/2015 | Kang |
| 2015/0198793 A1 | 7/2015 | Kosanic et al. |
| 2015/0355449 A1 | 12/2015 | Orth et al. |
| 2016/0091799 A1 | 3/2016 | Rachet et al. |
| 2016/0305926 A1 | 10/2016 | Rachet et al. |
| 2017/0055837 A1 | 3/2017 | Skitzki |
| 2017/0150872 A1 | 6/2017 | Kosanic et al. |
| 2019/0129158 A1 | 5/2019 | Shaffer et al. |
| 2019/0137752 A1 | 5/2019 | Shaffer et al. |
| 2020/0033581 A1 | 1/2020 | Shaffer et al. |
| 2020/0393665 A1 | 12/2020 | Shaffer et al. |

FOREIGN PATENT DOCUMENTS

| | | |
|---|---|---|
| EP | 0294902 A1 | 12/1988 |
| EP | 0991959 B1 | 6/2004 |
| EP | 1548481 A1 | 6/2005 |
| EP | 2299307 A2 | 3/2011 |
| EP | 1011441 B1 | 7/2011 |
| GB | 2408587 A | 6/2005 |
| WO | WO-90/01716 A1 | 2/1990 |
| WO | WO-97/34171 A2 | 9/1997 |
| WO | WO-1999/03008 A1 | 1/1999 |
| WO | WO-03/035824 A1 | 5/2003 |
| WO | WO-03/056378 A1 | 7/2003 |
| WO | WO-03065774 A1 | 8/2003 |
| WO | WO-2004/025668 A2 | 3/2004 |
| WO | WO-2005/096115 A1 | 10/2005 |
| WO | WO-2007/042989 A1 | 4/2007 |
| WO | WO-2008/012767 A2 | 1/2008 |
| WO | WO-2009/064746 A2 | 5/2009 |
| WO | WO-2010/084478 A2 | 7/2010 |
| WO | WO-2011/091283 A1 | 7/2011 |
| WO | WO-2014/013412 A1 | 1/2014 |
| WO | WO-2016/156516 A2 | 10/2016 |
| WO | WO-2017/001537 A1 | 1/2017 |
| WO | WO-2019/086550 A2 | 5/2019 |

OTHER PUBLICATIONS

Casaburi, A. et al., Two-and three-beam interferometric optical tweezers, Optics Communication, 251(4-6):393-404 (2005).

Constable, A. et al., Demonstration of a Fiber-Optic Light-Force Trap, Optics Letters, Optical Society of America, 18(21)1867-1869 (1993).

Cuche, E. et al., Digital Holography for quantitative phase-contrast imaging, Optics Letters, 24(5):291-293 (1999).

Davidson, N. et al, High-numerical-aperture focusing of radially polarized doughnut beams with a parabolic mirror and a flat diffractive lens, Optics Letters, 29(12)1318-1320 (2004).

(56) References Cited

OTHER PUBLICATIONS

Engelbrecht, C. J. et al., Ultra-compact fiber-optic two-photon microscope for functional fluorescence imaging in vivo, Optics Express, 16(8):5556-5564 (2008).

Glaser, A. K. et al., Light-sheet microscopy for slide-free non-destructive pathology of large clinical specimens, Nature Biomedical Engineering, 1(0084):1-10, (2017).

Guenther, R. et al., Device for the Optical Analysis of Samples, DE19729245C1, machine translation.

Hell, S. W. et al., Breaking the diffraction resolution limit by stimulated emission: stimulated-emission-depletion flourescence microscopy, Optics Letters 19(11):780-782 (1994).

International Search Report, PCT/EP2016/057113, 7 pages, dated Sep. 29, 2016.

Moktadir, Z. et al., Etching techniques for realizing optical microcavity atom traps on silicon, J. Micromech. Microeng., 14(9)S82-S85 (2004).

Orth, A. and Crozier, K., Gigapizel fluorescence microscopy with a water immersion microlens array, OSA, Optics Express, 21(2):2361-2368, (2013).

Orth, A. and Crozier, K., Microscopy with microlens arrays: high throughput, high resolution and light-field imaging, OSA, 20(12):Optics Express 13522, 10 pages (2012).

Partial International Search, PCT/EP2016/057113, 6 pages, dated Aug. 1, 2016.

Schmitt, J. M., Optical Coherence Tomography (OCT): A Review, IEEE Journal of Selected Topics in Quantum Electronics, 5(4):1205-1215 (1999).

Tiziani, H. J. et al., Three-dimensional analysis by a microlens-array confocal arrangement, Applied Optics, 33(4):567-572 (1994).

Völkel, R. et al., Microlens Lithograph, Diffractive Optics and micro-Optics: Summaries of the Papers Presented at the Topical Meeting, 1996 Technical Digets Series, Opitcal Society of America, 5:278-281, (1996).

Walecki, W. J. et al., Fast in-line surface topography metrology enabling stress calculation for solar cell manufacturing for throughput in excess of 2000 wafers per hour, Measurement Science and Technology, 19(025302):6 pages (2008).

Written Opinion, PCT/EP2016/057113, 13 pages, dated Sep. 29, 2016.

Zemanek, P. et al., Optical Trapping of Nanoparticles and Microparticles by a Gaussian Standing Wave, Optics Letters, Optical Society of America, 24(21)1448-1450 (1999).

Zhao, Y. et al., Development of a versatile two-photon endoscope for biological imaging, Biomedical Optics Express, 1(4):1159-1172 (2010).

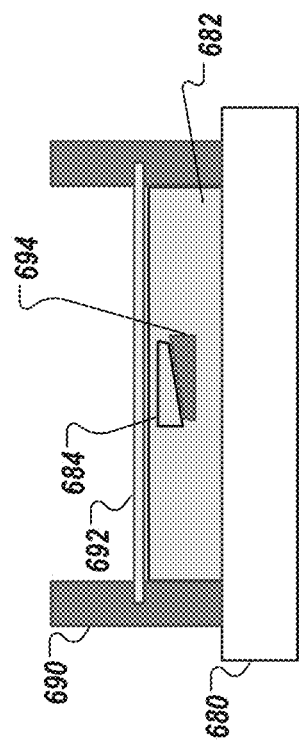
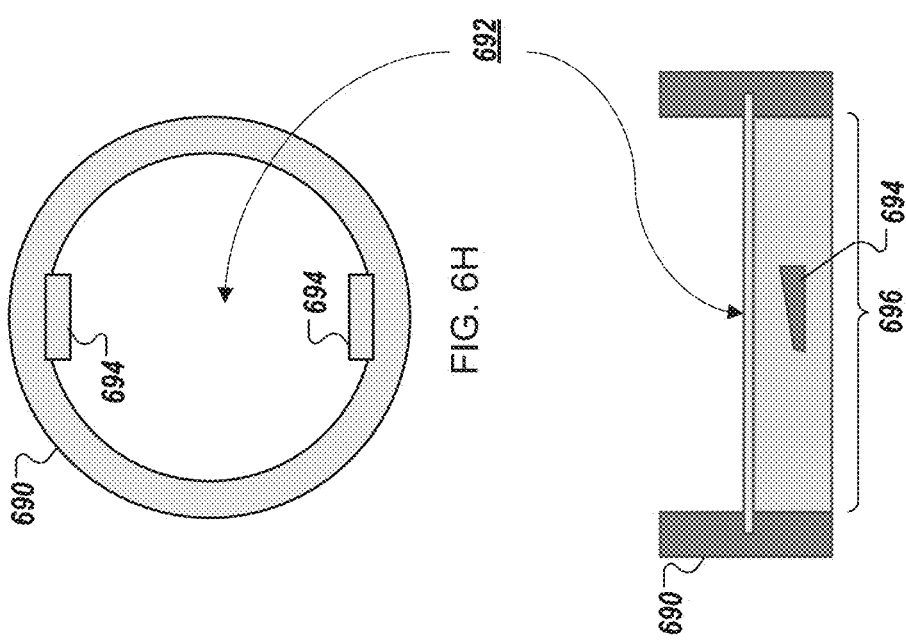

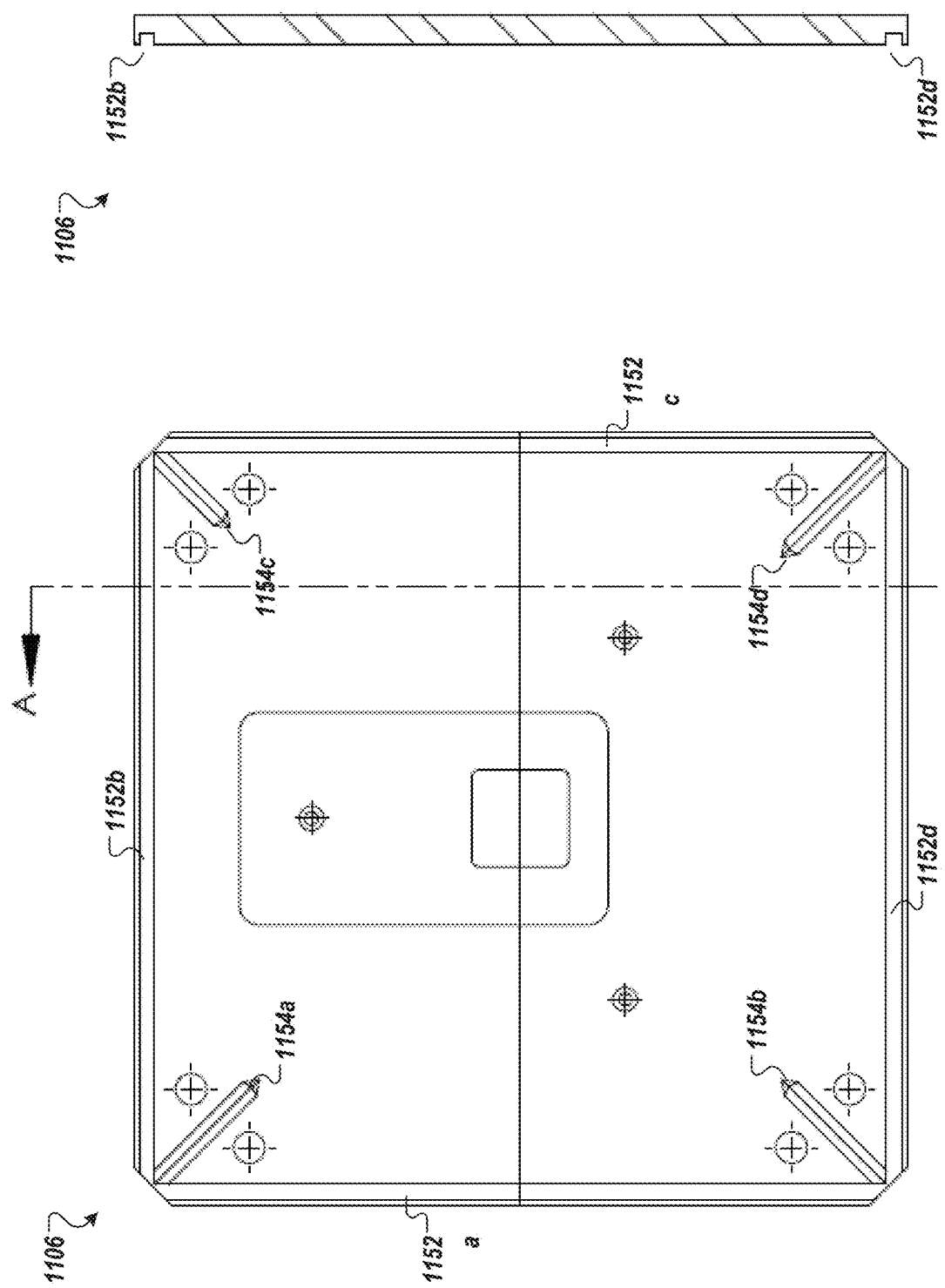

SYSTEMS AND METHODS FOR IN-OPERATING-THEATRE IMAGING OF FRESH TISSUE RESECTED DURING SURGERY FOR PATHOLOGY ASSESSMENT

RELATED APPLICATIONS

This application is a continuation of U.S. patent application Ser. No. 16/054,681, filed on Aug. 3, 2018, entitled Systems and Methods for In-Operating-Theatre Imaging of Fresh Tissue Resected During Surgery for Pathology Assessment, which is a continuation of U.S. patent application Ser. No. 15/200,126, filed on Jul. 1, 2016, entitled Systems and Methods for In-Operating-Theatre Imaging of Fresh Tissue Resected During Surgery for Pathology Assessment, which is a continuation of U.S. patent application Ser. No. 15/087,061, filed on Mar. 31, 2016, entitled Systems and Methods for In-Operating-Theatre Imaging of Fresh Tissue Resected During Surgery for Pathology Assessment, which claims priority to U.S. Provisional Patent Application Ser. No. 62/141,223, entitled Systems and Methods for In-Operating-Theatre Imaging of Fresh Tissue Resected During Surgery for Pathology Assessment by Rachet et al., the content of each of which is incorporated herein by reference in its entirety.

BACKGROUND OF THE INVENTION

Solid epithelial cancers account for over 10% of all deaths each year world-wide. This figure is expected to increase. Early-stage cancer diagnosis and subsequent complete surgical removal of the tumor offers the best chance for complete cancer cure. With early-stage tumor screening and diagnostics becoming more efficient, the bottleneck lies in efficient surgical management. Current surgical technology cannot precisely define the margins of a tumor, resulting in missed opportunities for life-saving treatment. Tumor residues may remain undetected and untreated until they grow to advanced stages, at which point both patient death rate and overall treatment costs can dramatically increase.

The diagnosis of a solid tumor typically involves (i) a screen via a blood test or mucosal smear (molecular diagnostics assays); (ii) gross tumor localization in the body typically by means of radiological imaging (e.g., PET, CT, MRI and ultrasound); and (iii) a visual inspection (e.g., endoscopy), and if necessary, the excision of a tissue sample (e.g., biopsy), and a subsequent pathologic examination.

The pathology laboratory analysis is crucial in the diagnostic process as it is often the basis for the final diagnosis at which the stage of the tumor is confirmed. The pathologist typically prepares thin tissue sections of a frozen or otherwise fixed tissue sample (e.g., a sample processed with formalin or paraffin) obtained during a diagnostic biopsy, then the pathologist examines the thin tissue sections under a microscope. The morphology of the tissue (e.g., cell size and cell arrangement) is the principal basis for distinguishing between healthy and cancer tissue, and for distinguishing between malignant and benign cancer tissue.

Because diagnostic techniques and cancer screens are improving, cancers are more frequently detected in the earlier stages. This gives oncology surgeons the opportunity to apply the most efficient and least invasive cancer treatment—complete surgical removal of the tumor.

If no metastases are present, minimally invasive surgical procedures can be used to remove the solid tumor. Typically, chemotherapy is not necessary for patients who undergo a complete resection of the tumor. However, a complete resection requires "tumor-free margins" of the resected tissue, meaning that no tumor cells are left behind in the patient.

Currently, there is no reliable means available to guide the resection of solid tumors. For certain indications, this results in the need to re-operate on many patients days after the initial operation when an analysis is obtained from the histo-pathology laboratory. Such follow-up surgical procedures usually lead to less favorable outcomes for the patient, psychological stress, and can roughly double treatment and hospitalization costs.

Healthcare institutions sometimes perform intra-operative frozen-section analysis (FSA) during certain tumor surgeries. Intra-operative FSA is a pathologic assessment of the resected tissue during ongoing surgeries. In spite of inherent problems, such as inferior sample quality when compared to standard paraffin-embedded histology, possible wrong diagnosis due to freezing artifacts (e.g., fatty tissue, like breast or brain tissue, is not suitable for rapid freezing), and tedious sample preparation (e.g., FSA needs to be planned ahead of surgery), long term studies show that intraoperative FSA can reduce the reoperation rate to 10% in the case of breast tumor resections.

However, intra-operative FSA requires the prolongation of operation time by at least 30 minutes, which, in addition to inconvenience for the patient and the clinical personnel, results in increased cost of the surgery and complications for operating theatre planning and management. Further, many tumor surgeries today do not include pathologic margin assessment, primarily due to the inconvenience and cost of a frozen section analysis. Thus, there is a need for a system for more efficient in-operating-theatre imaging of tissue.

SUMMARY OF THE INVENTION

The disclosed technology brings histopathology into the operating theatre, to enable real-time intra-operative digital pathology. The disclosed technology utilizes a confocal imaging device that can analyze, in the operating theatre, "optical slices" of fresh tissue without having to fix the resected tissue by freezing and/or processing with formalin or paraffin. This greatly reduces the time necessary for preparing and analyzing a sample and facilitates in-operating-theater analysis of tissue samples obtained during surgery.

For example, a tissue sample is obtained during surgery and the fresh tissue sample is analyzed by a confocal imaging device located in the operating theatre (e.g., where "operating theatre" includes the area in the operating room, adjacent to the operating room, and/or sufficiently near the operating room such that transport of the sample can be quick and/or does not involve taking the tissue sample out of a sterile environment). The sample is analyzed as a fresh tissue sample (without freezing or other fixation processing that kills cells in the sample), and results are obtained in a timely manner so that feedback is provided to the surgeon while the surgery is still proceeding. For example, images and/or other data obtained from the confocal imaging device can be analyzed remotely by a pathologist (and/or by automated analysis) such that results can be communicated to the surgeon in near real-time. In certain embodiments, the fresh tissue sample is analyzed and results provided to the surgeon within 1 minute of obtaining the sample, within 5 minutes of obtaining the sample, within 10 minutes of obtaining the sample, or within 15 minutes of obtaining the sample. In certain embodiments, the fresh tissue sample has a thickness within a range of 0.5-20 mm, 3-5 mm, 5-10 mm, 7-15 mm, 10-25 mm, 15-30 mm, or 25-35 mm or is no less than 0.2 mm, no less than 0.5 mm, no less than 1 mm, no less than 3 mm, or no less than 5 mm).

The disclosed technology, in certain embodiments, includes a simple, operating table-side digital histology scanner, with the capability of rapidly scanning all outer margins of a tissue sample (e.g., resection lump, removed tissue mass). Using point-scanning microscopy technology, the disclosed system, in certain embodiments, precisely scans an "optical section" of the resected tissue, and sends the digital image to a pathologist rather than the real tissue, thereby providing the pathologist with the opportunity to analyze the tissue intra-operatively. Thus, the disclosed technology provides digital images with the same information content as FSA, but faster and without destroying the tissue sample itself (e.g., without killing cells).

For example, a resection lump may be placed into the disclosed histology scanner by an operating theatre nurse and the scanner will rapidly (e.g., in less than 10 minutes) acquire pathology information necessary for an intra-operative pathology consultation. A pathologist can receive and view the digital images remotely and communicate his/her analysis digitally back into the operating theatre to guide the next surgical steps. Further, since the tissue is imaged outside of the patient, it can be stained with one or more of a wide range of fluorescent dyes (e.g., Proflavin, Acridin Orange, and eosin stain).

The disclosed technology, in some implementations, includes a medical device to assist a surgery group in obtaining a digital image at the microscopy level of a patient sample, for example, a tumorous tissue resected during cancer surgery. The captured image can be used by a pathologist to provide assistance, for example, from a remote location, to the surgery group. For example, the pathologist may evaluate the quality of the surgery from a remote location to ensure that the tumor has been completely removed. In certain embodiments, this review by the pathologist is performed quickly (e.g., in less than 5, 10, 15, or 20 minutes) such that if further removal of the tumor is necessary, the remaining portions of the tumor can be removed during the same operation.

In some implementations, the device includes a holder to carry the sample and position it on the reader and an imaging system (e.g., a reader) capable of fluorescence microscopy imaging on thick fresh tissue. In some implementations, a computer interface displays the images from the reader to the surgery group. In some implementations, sharing software is used to share images and comments with the pathology group (e.g., outside of the operating theatre).

In one aspect, the invention is directed to a system for in-operating-theatre imaging of fresh tissue samples resected during surgery (e.g., cancer surgery) for pathology assessment, the system comprising: a light source for providing (e.g., laser or other light source providing light with a wavelength of 488 nm or between 450-490 nm) an illumination beam that illuminates a fluorescent stained, fresh sample (e.g., a fluorescent-stained fresh sample) (e.g., an unsliced sample preserved for definitive assessment in follow-up testing), wherein the fresh sample is held by a sample holder located in an operating theatre; a beam expander (e.g., collimating lens (e.g., for use with a monomode fibered laser) or a telecentric afocal magnification relay (e.g., for use with a collimated laser)) for expanding the waist of the illumination beam to a size comparable to the field of view to be illuminated, thereby providing a collimated illumination beam; a beam splitter (e.g., dichroic mirror/filter, prism, or grating(s)) located between the sample and a detector array, for directing the collimated illumination beam toward a micro optical element array; the micro optical element array (e.g., comprising refractive lenses, Fresnel zone plates, micro reflective objectives, and/or GRIN lenses; e.g., a micro lens array) for focusing the collimated illumination beam from the beam splitter onto the sample, thereby forming an array of tight foci for exciting the fluorescence in the sample to produce the back-emitted light, wherein the micro optical element array is configured such that: the micro optical element array collects back-emitted light from the sample, and the collected back-emitted light propagates (e.g., as individual collimated beams) and is directed (e.g., by a set of optics) to a detector array; and a gap (e.g., an airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; a scanning stage for moving a position of the micro optical element array relative to the transparent window and the detector array such that back-emitted light collected by the micro optical element array is detected by the detector array to form a scanned confocal image (e.g., to construct an optical slice of the sample), wherein: the position of the transparent window relative to the detector array is fixed (e.g., during imaging of the sample by the system), and the scanning stage and micro optical element array are confined (e.g., fully confined) within the system such that the scanning stage and micro optical element array are protected from the sample (e.g., and the outside environment) by the transparent window; an aperture stop for spatially filtering the back-emitted light (e.g., fluorescent light between 510-520 nm, or light with a wavelength greater than or equal to 490 nm and, in some implementations, less than 530 nm; between 491 nm and 520 nm), thereby rejecting out-of-focus light (e.g., filtering out collected sample information that does not originate from the foci of the micro optical elements prior to detection by the detector array), wherein the detector array comprises a plurality of detectors, each detector independently detecting a portion of the back-emitted light originating from a micro optical element in the micro optical element array; and a computing device comprising a processor and a memory storing instructions thereon that, when executed by the processor, cause the processor to construct an image representing an optical slice of the fresh tissue sample based on the back-emitted light detected by the detector array.

In another aspect, the invention is directed to a system for in-operating-theatre imaging of fresh tissue samples resected during surgery (e.g., cancer surgery) for pathology assessment, the system comprising: a light source for providing (e.g., laser) an illumination beam that illuminates a fluorescent stained, fresh sample (e.g., a preserved sample—i.e., unsliced thereby preserving the sample for definitive assessment) held by a sample holder in an operating theatre; a beam expander (e.g., collimating lens) for expanding a waist of the illumination beam, thereby providing a collimated illumination beam; a beam splitter (e.g., dichroic mirror/filter, prism, or grating(s)), located between the sample and a detector array, for directing the collimated illumination beam toward a micro optical element array (e.g., using refractive lenses, Fresnel zone plates, micro reflective objectives, and/or GRIN lenses; e.g., a micro lens array); the micro optical element array for focusing the collimated illumination beam from the beam splitter onto the sample, thereby forming an array of tight foci for exciting the fluorescence in the sample to produce back-emitted light, wherein: the micro optical element array collects back-emitted light from the sample, and the collected back-emitted light propagates (e.g., as individual collimated beams) and is directed (e.g., by a set of optics) to a detector array; and a gap (e.g., an airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; a scanning stage for moving a position of the transparent window relative to the micro optical element array and the detector array such that back-emitted light collected by the micro optical element array is detected by the detector array to form a scanned confocal image (e.g., to construct an optical slice of the sample), wherein the position of the micro optical element array relative to the detector array is fixed (e.g., during imaging of the sample by the system); an aperture stop for spatially filtering the back-emitted light (e.g., fluorescent light between 510-520 nm, or light with a wavelength greater than or equal to 490 nm and, in some implementations, less than 530 nm, or between 491 nm and 520 nm), thereby rejecting out-of-focus light (e.g., filtering out collected sample information that is not originating from the foci of the micro optical elements prior to detection by the detector array), wherein the detector array comprises a plurality of detectors, each detector independently detecting a portion of the back-emitted light originating from a micro optical element in the micro optical element array; and a computing device comprising a processor and a memory storing instructions thereon that, when executed by the processor, cause the processor to construct an image representing an optical slice of the fresh tissue sample based on the back-emitted light detected by the detector array.

In certain embodiments, the memory stores instructions thereon that, when executed by the processor, cause the processor to send, via a network, the image to a second computing device such that a pathologist in a remote location (e.g., outside of the operating theatre) can perform the pathology assessment.

In certain embodiments, the micro optical element array comprises a plurality of micro optical elements having curved surfaces facing the sample. In certain embodiments, the micro optical element array comprises a plurality of micro optical elements having curved surfaces facing the collimated illumination beam.

In certain embodiments, the system comprises a kinematic support structure having at least three feet of adjustable height, the support structure supporting the scanning stage such that the height and tilt of the transparent window relative to the micro optical element array and the corresponding optical path are adjustable.

In certain embodiments, the system comprises a first flat mirror for reflecting the collimated illumination beam onto the beam splitter. In certain embodiments, the system comprises a second flat mirror for reflecting the collimated illumination beam from the beam splitter to the micro optical element array. In certain embodiments, the second flat mirror reflects the back-emitted light passed through the micro optical element array from the sample through the beam splitter.

In certain embodiments, the system comprises a field lens for focusing the back-emitted light prior to spatially filtering the back-emitted light.

In certain embodiments, the beam expander is a collimating lens.

In certain embodiments, the ratio of detectors to micro optical elements is from 1:1 to 1:12 (e.g., about 1:1, 1:2, 1:3, 1:4, 1:6, 1:8, or 1:12, e.g., to the nearest whole number, or within a range of any two of these values).

In certain embodiments, the micro optical element array comprises from 1000 to 100,000 micro optical elements (e.g., 1600 micro optical elements for a 10 mm field of view; 6400 micro optical elements for a 20 mm field of view, etc.).

In certain embodiments, the sample is stained with a fluorescent stain (e.g., proflavine, acridine orange, hematoxylin or eosin).

In certain embodiments, the system is configured for in-operating-theatre imaging of tissue (e.g., fresh) resected during surgery (e.g., cancer surgery) in less than 10 minutes (e.g., less than 5 minutes).

In certain embodiments, the system comprises a first computing device for sending information regarding the detected back-emitted light (e.g., an image captured by the camera) to a second computing device (e.g., remote from the first computer device—i.e., outside the operating theatre).

In certain embodiments, the sample holder is screwed onto the scanning stage.

In certain embodiments, the scanning stage is a three axis positioning stage (e.g., a high precision positioning stage, e.g., with precision equal or better than one micrometer; in other embodiments, the stage is a two-axis positioning stage, e.g., high precision positioning stage).

In certain embodiments, the sample holder comprises the transparent window.

In certain embodiments, the transparent window is a thin transparent window (e.g., 25-50 µm, or 50-100 µm thick; e.g., thin glass with a thickness from 25-50 µm or 50-100 µm).

In certain embodiments, the sample holder comprises a seal at the bottom of the transparent window to protect the system from sample liquid.

In certain embodiments, the transparent window provides an optical interface (e.g., transparent and flat between the sample and the micro optical element array.

In certain embodiments, the scanning stage is configured to bring the transparent window in close proximity to the micro optical element array (e.g., within 100 µm).

In certain embodiments, the sample holder comprises a metallic body.

In certain embodiments, the sample holder comprises an opening window (e.g., 40×20 mm, 10-50 mm by 10-50 mm; e.g., covered/filled by the transparent window).

In certain embodiments, the scanning stage comprises a translation mechanism which is configured for establishing a relative motion between said sample and said micro optical element array.

In certain embodiments, the sample is located in the focus area of the micro optical element array; and each micro optical element is configured to collect and direct sample information from the sample toward the detector.

In certain embodiments, the sample holder is configured (e.g. is sized and shaped) to accommodate a sample having a thickness that is within a range of 0.5-20 mm (e.g., that is within a range of 3-5 mm, 5-10 mm, 7-15 mm, 10-25 mm, 15-30 mm, or 25-35 mm, and/or that is no less than 0.5 mm, no less than 1 mm, no less than 3 mm, or no less than 5 mm).

In another aspect, the invention is directed to a method for in-operating-theatre imaging of fresh tissue samples resected during surgery (e.g., cancer surgery) for pathology assessment, the method comprising: providing, by a light source (e.g., laser or other light source providing light with a wavelength of 488 nm or between 450-490 nm), an illumination beam for illuminating a fluorescent stained, fresh sample (e.g., a fluorescent-stained fresh sample) (e.g., an unsliced sample preserved for definitive assessment in follow-up testing) held by a sample holder located in an operating theatre; directing a collimated light beam via illumination optics onto the fresh sample (e.g., the fresh fluorescent stained sample) held by the sample holder in the operating theatre, wherein the illumination optics comprise: a beam expander expanding a waist of the illumination beam, thereby providing the collimated illumination beam, a beam splitter (e.g., dichroic mirror/filter, prism, or grating(s)), located between the sample and a detector array, directing the collimated illumination beam toward a micro optical element array (e.g., the micro optical element array comprising refractive lenses, Fresnel zone plates, micro reflective objectives, and/or GRIN lenses; e.g., a micro lens array), and the micro optical element array for focusing the collimated illumination beam from the beam splitter onto the sample, thereby forming an array of tight foci for exciting the fluorescence in the sample to produce the back-emitted light, wherein: each micro optical element focuses a portion of the collimated illumination beam onto the sample, and a gap (e.g., airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; directing the back-emitted light from the sample to the detector array via detecting optics, the detecting optics comprising: the micro optical element array, which collects the back-emitted light from the sample, which propagates (e.g., as individual collimated beams) and is directed (e.g., by a set of optics) to the detector array, and an aperture stop spatially filtering the back-emitted light, thereby rejecting out-of-focus light; moving, by a scanning stage, a position of the micro optical element array relative to the transparent window and the detector array such that back-emitted light focused by the micro optical element array is detected by the detector array to form a scanned confocal image (e.g., to construct an optical slice of the sample), wherein: the position of the transparent window relative to the detector array is fixed (e.g., during imaging of the sample by the system), and the scanning stage and micro optical element array are confined (e.g., fully confined) within the system such that the scanning stage and micro optical element array are protected from the sample (e.g., and the outside environment) by the transparent window; detecting, by the detector array, the back-emitted light filtered by the aperture stop, wherein the detector array comprises a plurality of detectors, each detector independently detecting a portion of the back-emitted light originating from a micro optical element in the micro optical element array; and constructing, by a processor of a computing device, an image representing an optical slice of the fresh tissue sample based on the back-emitted light detected by the detector array.

In another aspect, the invention is directed to a method for in-operating-theatre imaging of fresh tissue resected during surgery (e.g., cancer surgery) for pathology assessment, the method comprising: providing, by a light source (e.g., laser or other light source providing light with a wavelength of 488 nm or between 450-490 nm), an illumination beam for illuminating a fluorescent stained, fresh sample (e.g., a preserved sample—i.e., unsliced thereby preserving the sample for definitive assessment) held by a sample holder in an operating theatre; directing a collimated light beam via illumination optics onto a fresh (e.g., fluorescent-stained) sample held by a sample holder in an operating theatre, wherein the illumination optics comprise: a beam expander expanding a waist of the illumination beam, thereby providing the collimated illumination beam, a beam splitter (e.g., dichroic mirror/filter, prism, or grating(s)), located between the sample and a detector array, directing the collimated illumination beam toward a micro optical element array (e.g., the micro optical element array comprising refractive lenses, Fresnel zone plates, micro reflective objectives, and/or GRIN lenses; e.g., a micro lens array), and the micro optical element array focusing the collimated illumination beam from the beam splitter onto the sample, thereby forming an array of tight foci for exciting the fluorescence in the sample to produce the back-emitted light, wherein: each micro optical element in the micro optical element array focuses a portion of the collimated illumination beam onto the sample, and a gap (e.g., airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; directing the back-emitted light from the sample to the detector array via detecting optics, the detecting optics comprising: the micro optical element array, which collects the back-emitted light that propagates (e.g., as individual collimated beams) and is directed (e.g., by a set of optics) to a detector array, and an aperture stop spatially filtering the back-emitted light, thereby rejecting out-of-focus light; moving, by a scanning stage, a position of the transparent window relative to the micro optical element array and the detector array such that back-emitted light focused by the micro optical element array is detected by the detector array to form a scanned confocal image (e.g., to construct an optical slice of the sample, wherein the position of the micro optical element array relative to the detector array is fixed (e.g., during imaging of the sample by the system); detecting, by the detector array, the back-emitted light filtered by the aperture stop, wherein the detector array comprises a plurality of detectors, each detector independently detecting a portion of the back-emitted light originating from a micro optical element in the micro optical element array; and constructing, by a processor of a computing device, an image representing an optical slice of the fresh tissue sample based on the back-emitted light detected by the detector array.

In certain embodiments, the method comprises sending, by the processor, via a network, the image to a second computing device such that a pathologist in a remote location (e.g., outside of the operating theatre) can perform the pathology assessment.

In certain embodiments, the micro optical element array comprises a plurality of micro optical elements having curved surfaces facing the sample.

In certain embodiments, the micro optical element array comprises a plurality of micro optical elements having curved surfaces facing the collimated illumination beam.

In certain embodiments, a kinematic support structure having at least three feet of adjustable height supports the scanning stage such that the height and tilt of the transparent window relative to the micro optical element array (e.g., and the corresponding optical path) are adjustable.

In certain embodiments, the illumination optics comprises: a first flat mirror reflecting the collimated illumination beam onto the beam splitter. In certain embodiments, the illumination optics comprises: a second flat mirror reflecting the collimated illumination beam from the beam splitter to the micro optical element array. In certain embodiments, the second flat mirror reflects the back-emitted light passed through the micro optical element array from the sample through the beam splitter.

In certain embodiments, the detection optics comprises: a field lens focusing the back-emitted light prior to spatially filtering the back-emitted light.

In certain embodiments, the beam expander is a collimating lens.

In certain embodiments, the ratio of detectors to micro optical elements is from 1:1 to 1:12 (e.g., about 1:1, 1:2, 1:3, 1:4, 1:6, 1:8, or 1:12, e.g., to the nearest whole number, or within a range of any two of these values).

In certain embodiments, the micro optical element array comprises from 1000 to 100,000 micro optical elements (e.g., 1600 micro optical elements for a 10 mm field of view; 6400 micro optical elements for a 20 mm field of view, etc.).

In certain embodiments, the sample is stained with a fluorescent stain (e.g., proflavine, acridine orange, hematoxylin or eosin).

In certain embodiments, the method is performed in less than 10 minutes (e.g., less than 5 minutes).

In certain embodiments, the method comprises sending, by a processor of a first computing device, to a second computing device (e.g., remote from the first computer device—i.e., outside the operating theatre) information regarding the detected back-emitted light (e.g., an image captured by the camera).

In certain embodiments, the method comprises, prior to providing an illumination beam for illuminating the sample: staining the sample with a fluorescent stain; and placing the sample in/on the sampler holder.

In certain embodiments, the sample holder is screwed onto the scanning stage.

In certain embodiments, the scanning stage is a three axis positioning stage (e.g., high precision positioning stage; e.g., in other embodiments, the scanning stage is a two-axis positioning stage, e.g., high precision positioning stage).

In certain embodiments, the sample holder comprises the transparent window.

In certain embodiments, the transparent window is a thin transparent window (e.g., 25-50 μm, or 50-100 μm thick).

In certain embodiments, the sample holder comprises a seal at the bottom of the transparent window to protect the system from sample liquid.

In certain embodiments, the transparent window provides an optical interface (e.g., transparent and flat) between the sample and the micro optical element array.

In certain embodiments, the scanning stage brings the transparent window in close proximity to the micro optical element array (e.g., within 100 μm).

In certain embodiments, the sample holder comprises a metallic body.

In certain embodiments, the sample holder comprises an opening (e.g., 40×20 mm, 10-50 mm by 10-50 mm) covered/filled by the transparent window.

In certain embodiments, the scanning stage comprises a translation system for establishing a relative motion between the sample and the micro optical element array.

In certain embodiments, the sample is located in the focus area of the micro optical element array; and each micro optical element is configured to collect and direct sample information from the sample towards the detector.

In certain embodiments, the sample has a thickness that is within a range of 0.5-20 mm (e.g., that is within a range of 3-5 mm, 5-10 mm, 7-15 mm, 10-25 mm, 15-30 mm, or 25-35 mm, and/or that is no less than 0.5 mm, no less than 1 mm, no less than 3 mm, or no less than 5 mm).

In another aspect, the invention is directed to a method for in-operating-theatre imaging of tissue (e.g., fresh tissue) resected during surgery (e.g., cancer surgery) for pathology assessment, the method comprising: intraoperatively resecting tissue to obtain a fresh tissue sample; procuring an image of the fresh tissue sample (e.g., using an embodiment of the system described herein); and sending, by a processor of a first computing device, to a second computing device (e.g., remote from the first computer device—i.e., outside the operating theatre) the image of the fresh tissue sample.

In various embodiments, elements or features described with respect to one aspect of the invention can be used with respect to another aspect of the invention (e.g., any limitation described with respect to a system embodiment of the invention can apply to a method embodiment of the invention, and vice versa).

In another aspect, the disclosed technology includes a system for in-operating-theatre imaging of fresh tissue samples resected during surgery (e.g., cancer surgery) for pathology assessment, the system including: a light source for providing (e.g., laser or other light source providing light with a wavelength of 488 nm or between 450-490 nm) an illumination beam that illuminates a fluorescent stained, fresh sample (e.g., a fluorescent-stained fresh sample) (e.g., an unsliced sample preserved for definitive assessment in follow-up testing), wherein the fresh sample is held by a sample holder located in an operating theatre; a beam expander (e.g., collimating lens (e.g., for use with a monomode fibered laser) or a telecentric afocal magnification relay (e.g., for use with a collimated laser)) for expanding the waist of the illumination beam to a size comparable to the field of view to be illuminated, thereby providing a collimated illumination beam; a beam splitter (e.g., dichroic mirror/filter, prism, or grating(s)) located between the sample and a detector array, for directing the collimated illumination beam toward a micro optical element array; the micro optical element array (e.g., comprising refractive lenses, Fresnel zone plates, micro reflective objectives, and/or GRIN lenses; e.g., a micro lens array) for focusing the collimated illumination beam from the beam splitter onto the sample, thereby forming an array of tight foci for exciting the fluorescence in the sample to produce the back-emitted light, wherein the micro optical element array is configured such that: the micro optical element array collects back-emitted light from the sample, and the collected back-emitted light propagates (e.g., as individual collimated beams) and is directed (e.g., by a set of optics) to a detector array; and a gap (e.g., an airgap) of less than 500 μm (e.g., 50-150 μm, 80-120 μm) is maintained between the micro optical element array and a window (e.g., a transparent window, e.g., made of glass, quartz, sapphire, plastic) onto which (e.g., above which) the sample is placed for imaging; a scanning stage for moving a position of the micro optical element array relative to the transparent window and the detector array such that back-emitted light collected by the micro optical element array is detected by the detector array to form a scanned confocal image (e.g., to construct an optical slice of the sample), wherein: the position of the transparent window relative to the detector array is fixed (e.g., during imaging of the sample by the system), and the scanning stage and micro optical element array are confined (e.g., fully confined) within the system such that the scanning stage and micro optical element array are protected from the sample (e.g., and the outside environment) by the transparent window; an aperture stop for spatially filtering the back-emitted light (e.g., fluorescent light between 510-520 nm, or light with a wavelength greater than or equal to 490 nm and, in some implementations, less than 530 nm; between 491 nm and 520 nm), thereby rejecting out-of-focus light (e.g., filtering out collected sample information that does not originate from the foci of the micro optical elements prior to detection by the detector array), wherein the detector array comprises a plurality of detectors, each detector independently detecting a portion of the back-emitted light originating from a micro optical element in the micro optical element array; and a computing device comprising a processor and a memory storing instructions thereon that, when executed by the processor, cause the processor to construct an image representing an optical slice of the fresh tissue sample based on the back-emitted light detected by the detector array.

In certain embodiments, the memory stores instructions thereon that, when executed by the processor, cause the processor to send, via a network, the image to a second computing device such that a pathologist in a remote location (e.g., outside of the operating theatre) can perform the pathology assessment.

In certain embodiments, the micro optical element array comprises a plurality of micro optical elements having curved surfaces facing the sample.

In certain embodiments, the micro optical element array comprises a plurality of micro optical elements having curved surfaces facing the collimated illumination beam.

In certain embodiments, the curved surface of each micro optical element has a conical shaped surface.

In certain embodiments, the curved surface of each micro optical element has a hyperbolic shaped surface.

In certain embodiments, the curved surface of each micro optical element has a conic constant from −1.8 to −2.2 (e.g., −2).

In certain embodiments, each micro optical element has a Strehl ratio greater than or equal to 0.8.

In certain embodiments, each micro optical element has a spot size from 0.2 μm to 5 μm, 0.2 μm to 1 μm, 0.3 μm to 0.6 μm, and 0.4 μm to 0.5 μm.

In certain embodiments, a free working distance (i.e., a distance from the tip of the micro optical elements to a focal plane of the micro optical element array) is from 80 μm to 450 μm, 150 μm to 350 μm, or 250 μm to 300 μm.

In certain embodiments, the micro optical element array has a focal plane from 10 μm to 200 μm, 20 μm to 150 μm, or 50 μm to 100 μm above the transparent window.

In certain embodiments, the system includes a kinematic support structure having at least three feet (e.g., four) of adjustable height, the support structure supporting the scanning stage such that the height and tilt of the transparent window relative to the micro optical element array and the corresponding optical path are adjustable.

In certain embodiments, the system includes a first flat mirror for reflecting the collimated illumination beam onto the beam splitter.

In certain embodiments, the system includes a second flat mirror for reflecting the collimated illumination beam from the beam splitter to the micro optical element array.

In certain embodiments, the second flat mirror reflects the back-emitted light passed through the micro optical element array from the sample through the beam splitter.

In certain embodiments, the system includes a field lens for focusing the back-emitted light prior to spatially filtering the back-emitted light.

In certain embodiments, the beam expander is a collimating lens.

In certain embodiments, the ratio of micro optical elements to detectors is from 1:1 to 1:100, 1:5 to 1:80, 1:20 to 1:70, 1:30 to 1:60, or 1:40 to 1:50 (e.g., about 1:1, 1:2, 1:3, 1:4, 1:6, 1:8, or 1:12, e.g., to the nearest whole number, or within a range of any two of these values).

In certain embodiments, the micro optical element array comprises from 1000 to 100,000 micro optical elements (e.g., 1600 micro optical elements for a 10 mm field of view; 6400 micro optical elements for a 20 mm field of view, etc.).

In certain embodiments, the sample is stained with a fluorescent stain (e.g., proflavine, acridine orange, hematoxylin or eosin).

In certain embodiments, the system is configured for in-operating-theatre imaging of tissue (e.g., fresh) resected during surgery (e.g., cancer surgery) in less than 10 minutes (e.g., less than 5 minutes).

In certain embodiments, the system includes a first computing device for sending information regarding the detected back-emitted light (e.g., an image captured by the camera) to a second computing device (e.g., remote from the first computer device—i.e., outside the operating theatre).

In certain embodiments, the system includes the sample holder is screwed onto the scanning stage.

In certain embodiments, the scanning stage is a three axis positioning stage (e.g., a high precision positioning stage, e.g., with precision equal or better than one micrometer; in other embodiments, the stage is a two-axis positioning stage, e.g., high precision positioning stage).

In certain embodiments, the sample holder comprises the transparent window.

In certain embodiments, the transparent window is a thin transparent window (e.g., 50-100 μm, or 100-500 μm thick; e.g., thin glass with a thickness from 50-100 μm or 100-500 μm).

In certain embodiments, the system includes an optical interface clamp (e.g., ring-shaped) that maintains the transparent window in place.

In certain embodiments, the sample holder comprises a seal at the bottom of the transparent window to protect the system from sample liquid.

In certain embodiments, the transparent window provides an optical interface (e.g., transparent and flat between the sample and the micro optical element array.

In certain embodiments, the scanning stage is configured to bring the transparent window in close proximity to the micro optical element array (e.g., within 100 μm).

In certain embodiments, the sample holder comprises a metallic body.

In certain embodiments, the sample holder comprises an opening window (e.g., 40×20 mm, 10-50 mm by 10-50 mm; e.g., covered/filled by the transparent window).

In certain embodiments, the scanning stage comprises a translation mechanism which is configured for establishing a relative motion between said sample and said micro optical element array.

In certain embodiments, the sample is located in the focus area of the micro optical element array; and each micro optical element is configured to collect and direct sample information from the sample toward the detector.

In certain embodiments, the sample holder is configured (e.g. is sized and shaped) to accommodate a sample having a thickness that is within a range of 0.5-20 mm (e.g., that is within a range of 3-5 mm, 5-10 mm, 7-15 mm, 10-25 mm, 15-30 mm, or 25-35 mm, and/or that is no less than 0.5 mm, no less than 1 mm, no less than 3 mm, or no less than 5 mm).

In certain embodiments, the system includes a mobile cart.

In certain embodiments, the system includes an attachment system for attaching a removable sample holder to the scanning stage.

In certain embodiments, the attachment system comprises a support base mounted on the scanning stage, the support base having a mount with one or more protrusions extending from the mount, wherein the mount is hollow on the inside and the support base has a corresponding opening therein such that an optical chip can scan a sample through the support base.

In another aspect, the disclosed technology includes a system for in-operating-theatre imaging of fresh tissue samples resected during surgery (e.g., cancer surgery) for pathology assessment, the system including: a light source for providing (e.g., laser) an illumination beam that illuminates a fluorescent stained, fresh sample (e.g., a preserved sample—i.e., unsliced thereby preserving the sample for definitive assessment) held by a sample holder in an operating theatre; a beam expander (e.g., collimating lens) for expanding a waist of the illumination beam, thereby providing a collimated illumination beam; a beam splitter (e.g., dichroic mirror/filter, prism, or grating(s)), located between the sample and a detector array, for directing the collimated illumination beam toward a micro optical element array (e.g., using refractive lenses, Fresnel zone plates, micro reflective objectives, and/or GRIN lenses; e.g., a micro lens array); the micro optical element array for focusing the collimated illumination beam from the beam splitter onto the sample, thereby forming an array of tight foci for exciting the fluorescence in the sample to produce back-emitted light, wherein: the micro optical element array collects back-emitted light from the sample, and the collected back-emitted light propagates (e.g., as individual collimated beams) and is directed (e.g., by a set of optics) to a detector array; and a gap (e.g., an airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; a scanning stage for moving a position of the transparent window relative to the micro optical element array and the detector array such that back-emitted light collected by the micro optical element array is detected by the detector array to form a scanned confocal image (e.g., to construct an optical slice of the sample), wherein the position of the micro optical element array relative to the detector array is fixed (e.g., during imaging of the sample by the system); an aperture stop for spatially filtering the back-emitted light (e.g., fluorescent light between 510-520 nm, or light with a wavelength greater than or equal to 490 nm and, in some implementations, less than 530 nm, or between 491 nm and 520 nm), thereby rejecting out-of-focus light (e.g., filtering out collected sample information that is not originating from the foci of the micro optical elements prior to detection by the detector array), wherein the detector array comprises a plurality of detectors, each detector independently detecting a portion of the back-emitted light originating from a micro optical element in the micro optical element array; and a computing device comprising a processor and a memory storing instructions thereon that, when executed by the processor, cause the processor to construct an image representing an optical slice of the fresh tissue sample based on the back-emitted light detected by the detector array.

In certain embodiments, the memory stores instructions thereon that, when executed by the processor, cause the processor to send, via a network, the image to a second computing device such that a pathologist in a remote location (e.g., outside of the operating theatre) can perform the pathology assessment.

In certain embodiments, the micro optical element array comprises a plurality of micro optical elements having curved surfaces facing the sample.

In certain embodiments, the micro optical element array comprises a plurality of micro optical elements having curved surfaces facing the collimated illumination beam.

In certain embodiments, the curved surface of each micro optical element has a conical shaped surface.

In certain embodiments, the curved surface of each micro optical element has a hyperbolic shaped surface.

In certain embodiments, the curved surface of each micro optical element has a conic constant from −1.8 to −2.2 (e.g., −2).

In certain embodiments, each micro optical element has a Strehl ratio greater than or equal to 0.8.

In certain embodiments, each micro optical element has a spot size from 0.2 µm to 5 µm, 0.2 µm to 1 µm, 0.3 µm to 0.6 µm, and 0.4 µm to 0.5 µm.

In certain embodiments, a free working distance (i.e., a distance from the tip of the micro optical elements to a focal plane of the micro optical element array) is from 80 µm to 450 µm, 150 µm to 350 µm, or 250 µm to 300 µm.

In certain embodiments, the micro optical element array has a focal plane from 10 µm to 200 µm, 20 µm to 150 µm, or 50 µm to 100 µm above the transparent window.

In certain embodiments, the system includes a kinematic support structure having at least three feet (e.g., four) of adjustable height, the support structure supporting the scanning stage such that the height and tilt of the transparent window relative to the micro optical element array and the corresponding optical path are adjustable.

In certain embodiments, the system includes a first flat mirror for reflecting the collimated illumination beam onto the beam splitter.

In certain embodiments, the system includes a second flat mirror for reflecting the collimated illumination beam from the beam splitter to the micro optical element array.

In certain embodiments, the second flat mirror reflects the back-emitted light passed through the micro optical element array from the sample through the beam splitter.

In certain embodiments, the system includes a field lens for focusing the back-emitted light prior to spatially filtering the back-emitted light.

In certain embodiments, the beam expander is a collimating lens.

In certain embodiments, the ratio of micro optical elements to detectors is from 1:1 to 1:100, 1:5 to 1:80, 1:20 to 1:70, 1:30 to 1:60, or 1:40 to 1:50 (e.g., about 1:1, 1:2, 1:3, 1:4, 1:6, 1:8, or 1:12, e.g., to the nearest whole number, or within a range of any two of these values).

In certain embodiments, the micro optical element array comprises from 1000 to 100,000 micro optical elements (e.g., 1600 micro optical elements for a 10 mm field of view; 6400 micro optical elements for a 20 mm field of view, etc.).

In certain embodiments, the sample is stained with a fluorescent stain (e.g., proflavine, acridine orange, hematoxylin or eosin).

In certain embodiments, the system is configured for in-operating-theatre imaging of tissue (e.g., fresh) resected during surgery (e.g., cancer surgery) in less than 10 minutes (e.g., less than 5 minutes).

In certain embodiments, the system includes a first computing device for sending information regarding the detected back-emitted light (e.g., an image captured by the camera) to a second computing device (e.g., remote from the first computer device—i.e., outside the operating theatre).

In certain embodiments, the system includes the sample holder is screwed onto the scanning stage.

In certain embodiments, the scanning stage is a three axis positioning stage (e.g., a high precision positioning stage, e.g., with precision equal or better than one micrometer; in other embodiments, the stage is a two-axis positioning stage, e.g., high precision positioning stage).

In certain embodiments, the sample holder comprises the transparent window.

In certain embodiments, the transparent window is a thin transparent window (e.g., 50-100 µm, or 100-500 µm thick; e.g., thin glass with a thickness from 50-100 µm or 100-500 µm).

In certain embodiments, the system includes an optical interface clamp (e.g., ring-shaped) that maintains the transparent window in place.

In certain embodiments, the sample holder comprises a seal at the bottom of the transparent window to protect the system from sample liquid.

In certain embodiments, the transparent window provides an optical interface (e.g., transparent and flat between the sample and the micro optical element array.

In certain embodiments, the scanning stage is configured to bring the transparent window in close proximity to the micro optical element array (e.g., within 100 µm).

In certain embodiments, the sample holder comprises a metallic body.

In certain embodiments, the sample holder comprises an opening window (e.g., 40×20 mm, 10-50 mm by 10-50 mm; e.g., covered/filled by the transparent window).

In certain embodiments, the scanning stage comprises a translation mechanism which is configured for establishing a relative motion between said sample and said micro optical element array.

In certain embodiments, the sample is located in the focus area of the micro optical element array; and each micro optical element is configured to collect and direct sample information from the sample toward the detector.

In certain embodiments, the sample holder is configured (e.g. is sized and shaped) to accommodate a sample having a thickness that is within a range of 0.5-20 mm (e.g., that is within a range of 3-5 mm, 5-10 mm, 7-15 mm, 10-25 mm, 15-30 mm, or 25-35 mm, and/or that is no less than 0.5 mm, no less than 1 mm, no less than 3 mm, or no less than 5 mm).

In certain embodiments, the system includes a mobile cart.

In certain embodiments, the system includes an attachment system for attaching a removable sample holder to the scanning stage.

In certain embodiments, the attachment system comprises a support base mounted on the scanning stage, the support base having a mount with one or more protrusions extending from the mount, wherein the mount is hollow on the inside and the support base has a corresponding opening therein such that an optical chip can scan a sample through the support base.

In another aspect, the disclosed technology includes a method for in-operating-theatre imaging of fresh tissue samples resected during surgery (e.g., cancer surgery) for pathology assessment, the method including: providing, by a light source (e.g., laser or other light source providing light with a wavelength of 488 nm or between 450-490 nm), an illumination beam for illuminating a fluorescent stained, fresh sample (e.g., a fluorescent-stained fresh sample) (e.g., an unsliced sample preserved for definitive assessment in follow-up testing) held by a sample holder located in an operating theatre; directing a collimated light beam via illumination optics onto the fresh sample (e.g., the fresh fluorescent stained sample) held by the sample holder in the operating theatre, wherein the illumination optics comprise: a beam expander expanding a waist of the illumination beam, thereby providing the collimated illumination beam, a beam splitter (e.g., dichroic mirror/filter, prism, or grating(s)), located between the sample and a detector array, directing the collimated illumination beam toward a micro optical element array (e.g., the micro optical element array comprising refractive lenses, Fresnel zone plates, micro reflective objectives, and/or GRIN lenses; e.g., a micro lens array), and the micro optical element array for focusing the collimated illumination beam from the beam splitter onto the sample, thereby forming an array of tight foci for exciting the fluorescence in the sample to produce the back-emitted light, wherein: each micro optical element focuses a portion of the collimated illumination beam onto the sample, and a gap (e.g., airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; directing the back-emitted light from the sample to the detector array via detecting optics, the detecting optics comprising: the micro optical element array, which collects the back-emitted light from the sample, which propagates (e.g., as individual collimated beams) and is directed (e.g., by a set of optics) to the detector array, and an aperture stop spatially filtering the back-emitted light, thereby rejecting out-of-focus light; moving, by a scanning stage, a position of the micro optical element array relative to the transparent window and the detector array such that back-emitted light focused by the micro optical element array is detected by the detector array to form a scanned confocal image (e.g., to construct an optical slice of the sample), wherein: the position of the transparent window relative to the detector array is fixed (e.g., during imaging of the sample by the system), and the scanning stage and micro optical element array are confined (e.g., fully confined) within the system such that the scanning stage and micro optical element array are protected from the sample (e.g., and the outside environment) by the transparent window; detecting, by the detector array, the back-emitted light filtered by the aperture stop, wherein the detector array comprises a plurality of detectors, each detector independently detecting a portion of the back-emitted light originating from a micro optical element in the micro optical element array; and constructing, by a processor of a computing device, an image representing an optical slice of the fresh tissue sample based on the back-emitted light detected by the detector array.

In certain embodiments, the method includes sending, by the processor, via a network, the image to a second computing device such that a pathologist in a remote location (e.g., outside of the operating theatre) can perform the pathology assessment.

In certain embodiments, the micro optical element array comprises a plurality of micro optical elements having curved surfaces facing the sample.

In certain embodiments, the micro optical element array comprises a plurality of micro optical elements having curved surfaces facing the collimated illumination beam.

In certain embodiments, the curved surface of each micro optical element has a conical shaped surface.

In certain embodiments, the curved surface of each micro optical element has a hyperbolic shaped surface.

In certain embodiments, the curved surface of each micro optical element has a conic constant from −1.8 to −2.2 (e.g., −2).

In certain embodiments, each micro optical element has a Strehl ratio greater than or equal to 0.8.

In certain embodiments, each micro optical element has a spot size of 0.1 µm to 2 µm, 0.2 µm to 1 µm, 0.3 µm to 0.6 µm, or 0.4 µm to 0.5 µm.

In certain embodiments, a free working distance (i.e., a distance from the tip of the micro optical elements to a focal plane of the micro optical element array) is from 80 µm to 450 µm, 150 µm to 350 µm, or 250 µm to 300 µm.

In certain embodiments, the micro optical element array has a focal plane from 10 µm to 200 µm, 20 µm to 150 µm, or 50 µm to 100 µm above the transparent window.

In certain embodiments, a kinematic support structure having at least three feet (e.g., four) of adjustable height supports the scanning stage such that the height and tilt of the transparent window relative to the micro optical element array (e.g., and the corresponding optical path) are adjustable.

In certain embodiments, the illumination optics includes: a first flat mirror reflecting the collimated illumination beam onto the beam splitter.

In certain embodiments, the illumination optics includes a second flat mirror reflecting the collimated illumination beam from the beam splitter to the micro optical element array.

In certain embodiments, the second flat mirror reflects the back-emitted light passed through the micro optical element array from the sample through the beam splitter.

In certain embodiments, the detection optics comprises: a field lens focusing the back-emitted light prior to spatially filtering the back-emitted light.

In certain embodiments, the beam expander is a collimating lens.

In certain embodiments, the ratio of detectors to micro optical elements is from 1:1 to 1:100, 1:5 to 1:80, 1:20 to 1:70, 1:30 to 1:60, or 1:40 to 1:50 (e.g., about 1:1, 1:2, 1:3, 1:4, 1:6, 1:8, or 1:12, e.g., to the nearest whole number, or within a range of any two of these values).

In certain embodiments, the micro optical element array comprises from 1000 to 100,000 micro optical elements (e.g., 1600 micro optical elements for a 10 mm field of view; 6400 micro optical elements for a 20 mm field of view, etc.).

In certain embodiments, the sample is stained with a fluorescent stain (e.g., proflavine, acridine orange, hematoxylin or eosin).

In certain embodiments, the method is performed in less than 10 minutes (e.g., less than 5 minutes).

In certain embodiments, the method includes sending, by a processor of a first computing device, to a second computing device (e.g., remote from the first computer device—i.e., outside the operating theatre) information regarding the detected back-emitted light (e.g., an image captured by the camera).

In certain embodiments, the method includes, prior to providing an illumination beam for illuminating the sample: staining the sample with a fluorescent stain; and placing the sample in/on the sampler holder.

In certain embodiments, the sample holder is screwed onto the scanning stage.

In certain embodiments, the scanning stage is a three axis positioning stage (e.g., high precision positioning stage; e.g., in other embodiments, the scanning stage is a two-axis positioning stage, e.g., high precision positioning stage).

In certain embodiments, the sample holder comprises the transparent window.

In certain embodiments, the transparent window is a thin transparent window (e.g., 50-100 µm, or 100-500 µm thick; e.g., thin glass with a thickness from 50-100 µm or 100-500 µm).

In certain embodiments, the sample holder comprises a seal at the bottom of the transparent window to protect the system from sample liquid.

In certain embodiments, the transparent window provides an optical interface (e.g., transparent and flat) between the sample and the micro optical element array.

In certain embodiments, the scanning stage brings the transparent window in close proximity to the micro optical element array (e.g., within 100 µm).

In certain embodiments, the sample holder comprises a metallic body.

In certain embodiments, the sample holder comprises an opening (e.g., 40×20 mm, 10-50 mm by 10-50 mm) covered/filled by the transparent window.

In certain embodiments, the scanning stage comprises a translation system for establishing a relative motion between the sample and the micro optical element array.

In certain embodiments, the sample is located in the focus area of the micro optical element array; and each micro optical element is configured to collect and direct sample information from the sample towards the detector.

In certain embodiments, the sample has a thickness that is within a range of 0.5-20 mm (e.g., that is within a range of 3-5 mm, 5-10 mm, 7-15 mm, 10-25 mm, 15-30 mm, or 25-35 mm, and/or that is no less than 0.5 mm, no less than 1 mm, no less than 3 mm, or no less than 5 mm).

In another aspect, the disclosed technology includes the disclosed technology includes a method for in-operating-theatre imaging of fresh tissue resected during surgery (e.g., cancer surgery) for pathology assessment, the method including: providing, by a light source (e.g., laser or other light source providing light with a wavelength of 488 nm or between 450-490 nm), an illumination beam for illuminating a fluorescent stained, fresh sample (e.g., a preserved sample—i.e., unsliced thereby preserving the sample for definitive assessment) held by a sample holder in an operating theatre; directing a collimated light beam via illumination optics onto a fresh (e.g., fluorescent-stained) sample held by a sample holder in an operating theatre, wherein the illumination optics comprise: a beam expander expanding a waist of the illumination beam, thereby providing the collimated illumination beam, a beam splitter (e.g., dichroic mirror/filter, prism, or grating(s)), located between the sample and a detector array, directing the collimated illumination beam toward a micro optical element array (e.g., the micro optical element array comprising refractive lenses, Fresnel zone plates, micro reflective objectives, and/or GRIN lenses; e.g., a micro lens array), and the micro optical element array focusing the collimated illumination beam from the beam splitter onto the sample, thereby forming an array of tight foci for exciting the fluorescence in the sample to produce the back-emitted light, wherein: each micro optical element in the micro optical element array focuses a portion of the collimated illumination beam onto the sample, and a gap (e.g., airgap) of less than 500 µm (e.g., 50-150 µm, 80-120 µm) is maintained between the micro optical element array and a transparent window (e.g., glass, quartz, sapphire, plastic) onto which (e.g., above which) the sample is placed for imaging; directing the back-emitted light from the sample to the detector array via detecting optics, the detecting optics comprising: the micro optical element array, which collects the back-emitted light that propagates (e.g., as individual collimated beams) and is directed (e.g., by a set of optics) to a detector array, and an aperture stop spatially filtering the back-emitted light, thereby rejecting out-of-focus light; moving, by a scanning stage, a position of the transparent window relative to the micro optical element array and the detector array such that back-emitted light focused by the micro optical element array is detected by the detector array to form a scanned confocal image (e.g., to construct an optical slice of the sample, wherein the position of the micro optical element array relative to the detector array is fixed (e.g., during imaging of the sample by the system); detecting, by the detector array, the back-emitted light filtered by the aperture stop, wherein the detector array comprises a plurality of detectors, each detector independently detecting a portion of the back-emitted light originating from a micro optical element in the micro optical element array; and constructing, by a processor of a computing device, an image representing an optical slice of the fresh tissue sample based on the back-emitted light detected by the detector array.

In certain embodiments, the method includes sending, by the processor, via a network, the image to a second computing device such that a pathologist in a remote location (e.g., outside of the operating theatre) can perform the pathology assessment.

In certain embodiments, the micro optical element array comprises a plurality of micro optical elements having curved surfaces facing the sample.

In certain embodiments, the micro optical element array comprises a plurality of micro optical elements having curved surfaces facing the collimated illumination beam.

In certain embodiments, the curved surface of each micro optical element has a conical shaped surface.

In certain embodiments, the curved surface of each micro optical element has a hyperbolic shaped surface.

In certain embodiments, the curved surface of each micro optical element has a conic constant from −1.8 to −2.2 (e.g., −2).

In certain embodiments, each micro optical element has a Strehl ratio greater than or equal to 0.8.

In certain embodiments, each micro optical element has a spot size of 0.1 µm to 2 µm, 0.2 µm to 1 µm, 0.3 µm to 0.6 µm, or 0.4 µm to 0.5 µm.

In certain embodiments, a free working distance (i.e., a distance from the tip of the micro optical elements to a focal plane of the micro optical element array) is from 80 µm to 450 µm, 150 µm to 350 µm, or 250 µm to 300 µm.

In certain embodiments, the micro optical element array has a focal plane from 10 µm to 200 µm, 20 µm to 150 µm, or 50 µm to 100 µm above the transparent window.

In certain embodiments, a kinematic support structure having at least three feet (e.g., four) of adjustable height supports the scanning stage such that the height and tilt of the transparent window relative to the micro optical element array (e.g., and the corresponding optical path) are adjustable.

In certain embodiments, the illumination optics includes: a first flat mirror reflecting the collimated illumination beam onto the beam splitter.

In certain embodiments, the illumination optics includes a second flat mirror reflecting the collimated illumination beam from the beam splitter to the micro optical element array.

In certain embodiments, the second flat mirror reflects the back-emitted light passed through the micro optical element array from the sample through the beam splitter.

In certain embodiments, the detection optics comprises: a field lens focusing the back-emitted light prior to spatially filtering the back-emitted light.

In certain embodiments, the beam expander is a collimating lens.

In certain embodiments, the ratio of detectors to micro optical elements is from 1:1 to 1:100, 1:5 to 1:80, 1:20 to 1:70, 1:30 to 1:60, or 1:40 to 1:50 (e.g., about 1:1, 1:2, 1:3, 1:4, 1:6, 1:8, or 1:12, e.g., to the nearest whole number, or within a range of any two of these values).

In certain embodiments, the micro optical element array comprises from 1000 to 100,000 micro optical elements (e.g., 1600 micro optical elements for a 10 mm field of view; 6400 micro optical elements for a 20 mm field of view, etc.).

In certain embodiments, the sample is stained with a fluorescent stain (e.g., proflavine, acridine orange, hematoxylin or eosin).

In certain embodiments, the method is performed in less than 10 minutes (e.g., less than 5 minutes).

In certain embodiments, the method includes sending, by a processor of a first computing device, to a second computing device (e.g., remote from the first computer device—i.e., outside the operating theatre) information regarding the detected back-emitted light (e.g., an image captured by the camera).

In certain embodiments, the method includes, prior to providing an illumination beam for illuminating the sample: staining the sample with a fluorescent stain; and placing the sample in/on the sampler holder.

In certain embodiments, the sample holder is screwed onto the scanning stage.

In certain embodiments, the scanning stage is a three axis positioning stage (e.g., high precision positioning stage; e.g., in other embodiments, the scanning stage is a two-axis positioning stage, e.g., high precision positioning stage).

In certain embodiments, the sample holder comprises the transparent window.

In certain embodiments, the transparent window is a thin transparent window (e.g., 50-100 µm, or 100-500 µm thick; e.g., thin glass with a thickness from 50-100 µm or 100-500 µm).

In certain embodiments, the sample holder comprises a seal at the bottom of the transparent window to protect the system from sample liquid.

In certain embodiments, the transparent window provides an optical interface (e.g., transparent and flat) between the sample and the micro optical element array.

In certain embodiments, the scanning stage brings the transparent window in close proximity to the micro optical element array (e.g., within 100 µm).

In certain embodiments, the sample holder comprises a metallic body.

In certain embodiments, the sample holder comprises an opening (e.g., 40×20 mm, 10-50 mm by 10-50 mm) covered/filled by the transparent window.

In certain embodiments, the scanning stage comprises a translation system for establishing a relative motion between the sample and the micro optical element array.

In certain embodiments, the sample is located in the focus area of the micro optical element array; and each micro optical element is configured to collect and direct sample information from the sample towards the detector.

In certain embodiments, the sample has a thickness that is within a range of 0.5-20 mm (e.g., that is within a range of 3-5 mm, 5-10 mm, 7-15 mm, 10-25 mm, 15-30 mm, or 25-35 mm, and/or that is no less than 0.5 mm, no less than 1 mm, no less than 3 mm, or no less than 5 mm).

In another aspect, the disclosed technology includes a method for in-operating-theatre imaging of tissue (e.g., fresh tissue) resected during surgery (e.g., cancer surgery) for pathology assessment, the method including: intraoperatively resecting tissue to obtain a fresh tissue sample;

procuring an image of the fresh tissue sample (e.g., using the system of any one of claims 1 to 39); and sending, by a processor of a first computing device, to a second computing device (e.g., remote from the first computer device—i.e., outside the operating theatre) the image of the fresh tissue sample.

In another aspect, the disclosed technology includes a sample holding device, including: a support base that can be mounted on a pathology system, the support base comprising a mount having one or more protrusions extending from the mount, wherein the mount is hollow on the inside and the support base has a corresponding opening therein such that an optical chip can scan a sample through the support base; and a removable sample holder that is removably attachable to the support base, the removable sample holder comprising: a housing having an opening therethrough with one or more (e.g., two) interior protrusions extending into the opening, wherein the size and shape (e.g., round, cylindrical, circular) of the opening in the housing is such that the removable sample holder can be attached over the support base and twisted such that the one or more interior protrusions of the removable sample holder engage the one or more protrusions of the support base, thereby securing the removable sample holder to the support base; and a transparent window on which the sample can be placed and through which the optical chip can image the sample.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 6A-6J is an illustration of an example sample holder, in accordance with an embodiment of the invention;

FIGS. 11E through 11G are illustrations of an example optical interface mount, in accordance with an embodiment of the invention;

Figure 1A:
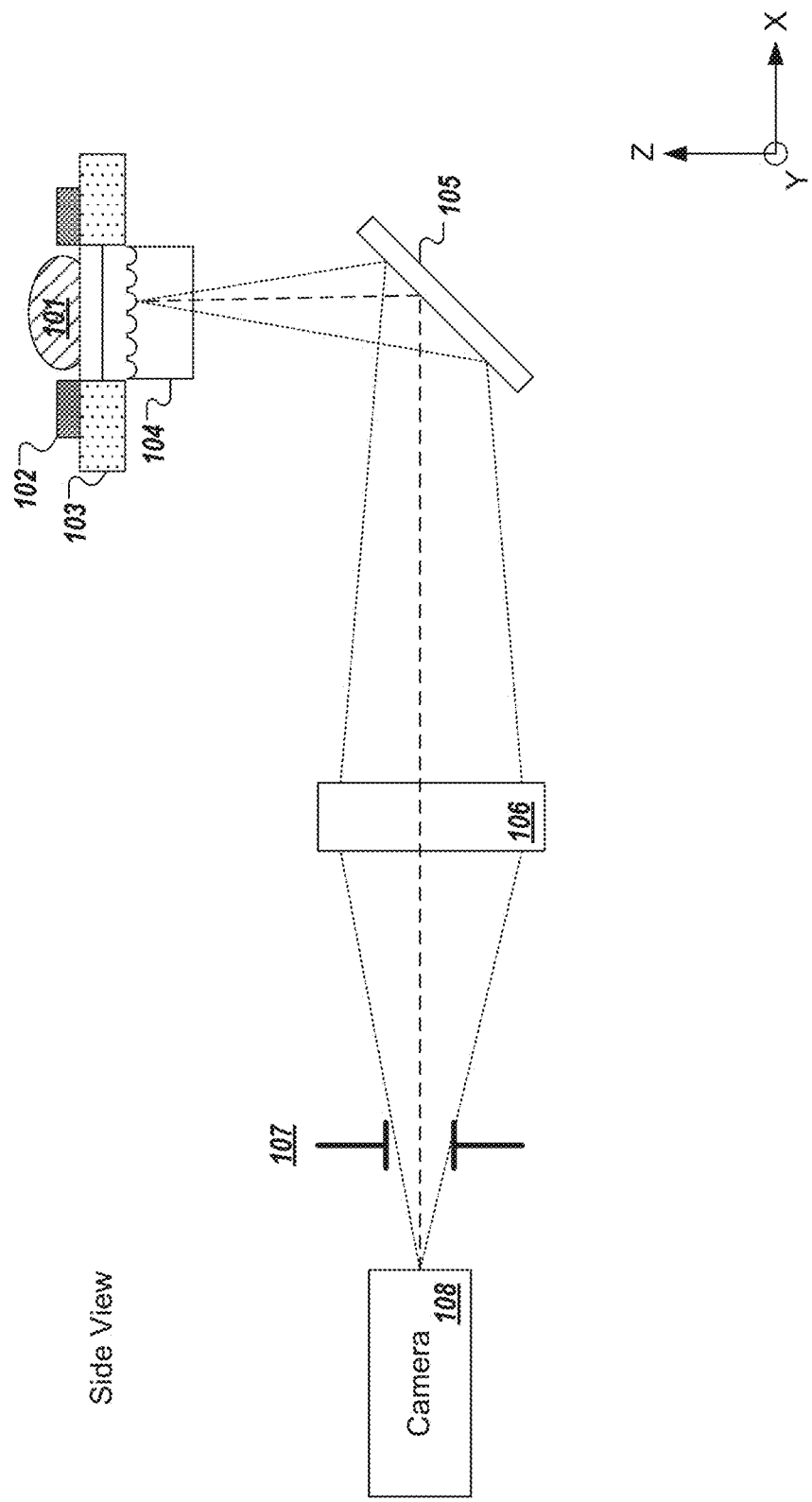
FIG. 1A is a side view of an example system for in-operating-theatre of fresh thick tissue resected during surgery, in accordance with an embodiment of the invention.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

In the present text the expression "micro optical element" is used to describe a miniaturized focusing element with a cross sectional diameter of less than 1 mm (e.g., between 10 micrometers and 500 micrometers) that focuses light. In some implementations, the micro optical element is a micro lens having a paraxial radius of curvature that is in the order of magnitude of its diameter. In some implementations, the micro optical element is a refractive lens, Fresnel zone plate, GRIN lens, or micro reflective objective. The term "micro optical element array" is used to describe a structure composed of a plurality of micro optical elements positioned in a grid which may be, but is not necessarily, periodic. While the description may describe embodiments of the disclosed technology implemented with a micro lens array, similar embodiments may be implemented with micro optical elements.

The expression "fresh tissue" is generally used herein to describe tissue resected or otherwise obtained during surgery that is not fixed tissue. For example, fresh tissue has not been frozen or processed with formalin, paraffin. In some implementations, the fresh tissue sample is in the same or similar state that it was in when it was removed from the patient. Fresh tissue is a living tissue that has not yet been fixed, in the histology terminology understanding. In the fields of histology and pathology, fixation is a critical step in the preparation of histological sections by which biological tissues are preserved from decay, thereby preventing autolysis or putrefaction. The broad objective of tissue fixation is to preserve cells and tissue components and to do this in such a way as to allow for the preparation of thin, stained sections.

Even though the microscopy system described herein may be used to image fixed thin tissue sections, an advantage that is achieved, in certain embodiments, is to provide a solution for fresh tissue imaging that does not necessitate a fixation procedure and thin slicing of the sample. In consequence, embodiments described herein allow microscopic imaging on fresh thick tissue, in contrast to standard preparation of fixed thin tissue in histology.

In the present text the expression "operating theatre" is used to describe a facility within a hospital where surgical operations are carried out in a sterile environment, including an operating room and operating suite. It also refers to an operating room with an on-site laboratory (e.g., adjacent to the operating room). In some implementations, the operating theatre is an operating room.

The disclosed technology may be used for the observation of thick fresh tissue samples (e.g., having a thickness within a range of 0.5-20 mm, 3-5 mm, 5-10 mm, 7-15 mm, 10-25 mm, 15-30 mm, or 25-35 mm or is no less than 0.2 mm, no less than 0.5 mm, no less than 1 mm, no less than 3 mm, or no less than 5 mm)) at a cellular level during surgery in order to provide pathology assistance to ongoing surgery. The sample may be processed using the disclosed technology in less than 10 minutes (e.g., less than 5 mins) because, for example, the sample does not need to be mechanically sliced as the disclosed microscopy may be used directly on fresh thick tissue (e.g., using optical slicing, a non-destructive method). Further, the technical speed of reading the sample is improved, and this approach preserves the sample such that it is available for definitive assessment (contrary of FSA). Additionally, images can be shared electronically which allows direct connection between the pathologist and the surgical team.

Figure 1B:
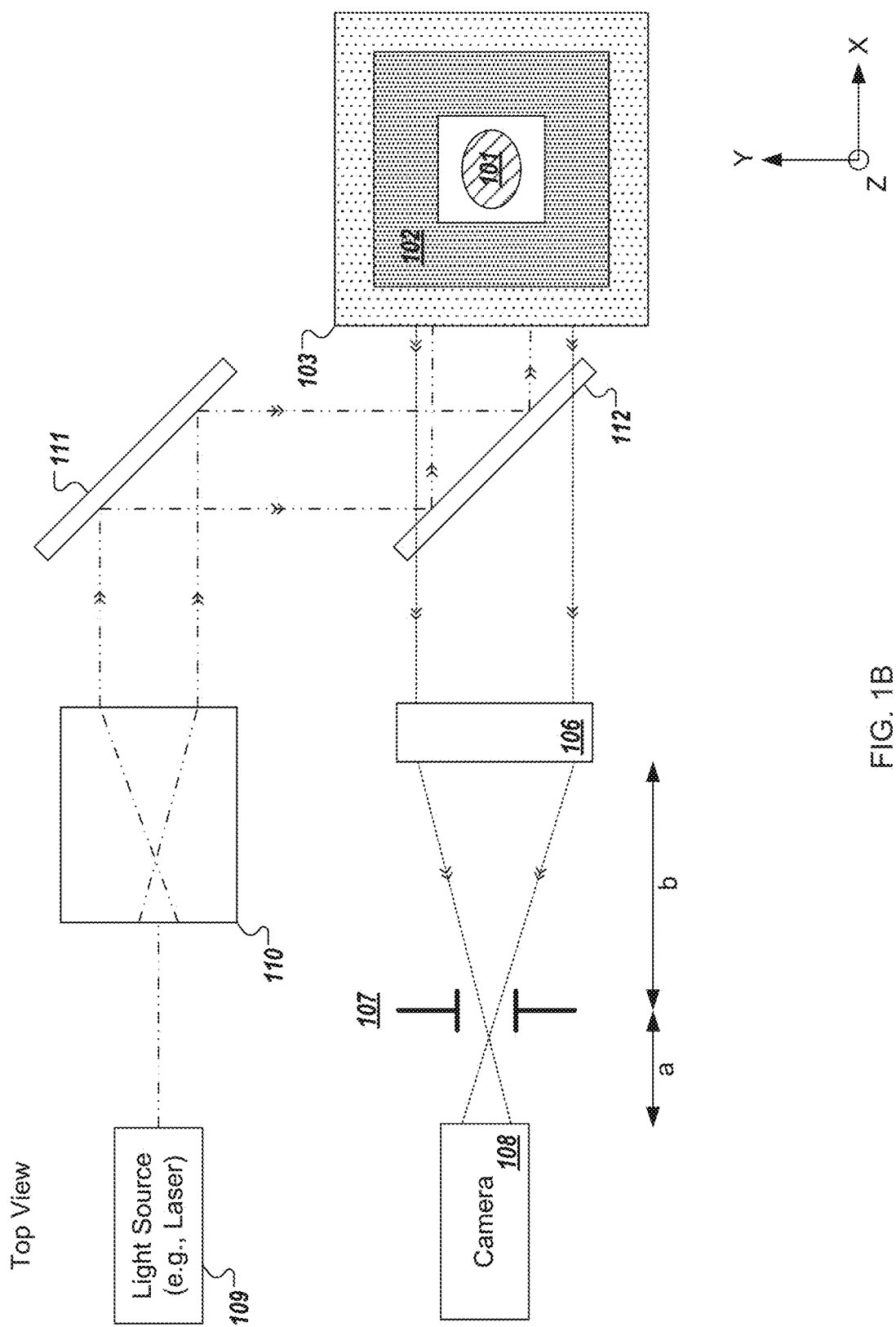
FIG. 1B is a top view of an example system for in-operating-theatre of fresh thick tissue resected during surgery, in accordance with an embodiment of the invention.

FIG. 1A illustrates a top view of an example in-operating-theatre pathology system for imaging fresh, thick tissue. FIG. 1B illustrates a side view of the same example system. The disclosed technology uses a micro lens array 104 for performing large-field high resolution microscopy and/or micro-projection of in-operating-theatre imaging for fresh, thick tissue for pathology assessment. Fresh thick tissue is typically difficult to image as the illumination light is passed through the sample 101, such as a biopsy or a tumor resection, and the collected emission light collected also travels through the sample 101. The disclosed technology overcomes this challenge by using, among other things, transmitting optics to limit the part of the light path that has to propagate into the sample 101, thereby allowing imaging of fresh thick tissue. Examples of transmitting optics that can be used include refractive lens, Fresnel zone plate and the micro reflective objective described in U.S. patent application Ser. No. 14/415106, filed January 2015, entitled Reflective Optical Objective, which is hereby incorporated by reference in its entirety and attached hereto as an Appendix.

The illumination light is provided by a light source 109 and is directed onto a beam splitter 112 that transmits the collected light. In some implementations, the illumination light is projected directly onto the beam splitter 112. In other implementations, a flat mirror 111 redirects the illumination light onto the beam splitter 112.

In some implementations, a beam expander 110 (e.g., collimating lens) expands the waist of the illumination beam prior to the light reaching the beam splitter 112, thereby providing an expanded illumination beam. In some implementations, the expanded illumination beam is projected directly onto the beam splitter 112. In other implementations, a flat mirror 111 redirects the expanded illumination beam onto the beam splitter 112.

The beam splitter 112 reflects the illumination beam (i.e., the unexpanded illumination beam or expanded illumination beam depending on whether a beam expander is used) to a micro lens array 104. In some implementations, the beam splitter 112 transmits the illumination beam to a micro lens array 104 via a flat mirror 105.

In some implementations, the beam splitter 112 separates light (e.g., reflects the illumination beams and allows the back-emitted light to pass therethrough) according to its wavelength, its polarization or without such distinctions. For example, a dichroic mirror or a polarizing cube associated with a quarter-wave, half-wave plate or a partially reflecting mirror can be used to achieve the desired effect.

In some implementations, the system includes a micro lens array 104 that focuses the illumination beam onto a sample 101. The illumination beam is focused by each of the micro lens, producing an array of foci in the sample 101. The micro lens array 104 focuses the collimated light into the sample 101, forming an array of tight foci in which fluorescence will be excited (e.g., fluorescence from the fluorescence stained sample 101).

In some implementations, the micro lens array 104 includes plano-convex spherical lenses that focus the collimated beam of light. The plano-convex spherical lenses, in some implementations, are used with their curved surface facing the collimated beam in order to minimize aberrations (e.g., spherical aberrations).

The same micro lens array 104 allows the light emitted from the sample 101 (i.e., back-emitted light) as a result of the illumination to pass ultimately towards a detector array 108. The light emitted by the sample 101 in response to the illumination, in some implementations, is collected by each of the micro lens. In this example, the collected light then propagates as individual collimated beams. In some implementations, the flat mirror 105 reflects the back-emitted light to the beam splitter 112. In contrast to the illumination beam which the beam splitter 112 reflects, the beam splitter 112 transmits the back-emitted light.

After the back-emitted light passes through the beam splitter 112, imaging optics 106 (e.g., field lens) focus the back-emitted light from the beam splitter 112 onto the detector 108, thereby imaging the micro lens plane onto the detector plane. In some implementations, the back-emitted light from the beam splitter 112 is focused onto the detector 108 via an aperture stop 107 (e.g., pinhole). The aperture stop 107 spatially filters the light, thereby rejecting out-of-focus light.

In some implementations, the light originating from each individual micro lens is independently detected by dedicated sensors element of the detector array 108. The sensitive elements of the detector array 108 can be any type of sensor sensitive to the light collected by the micromirrors, such as CMOS or CCD photodetectors, photodiodes, phototransistors, avalanche photodiodes, photoresistors, Golay cells, bolometer thermopiles or pyroelectric detectors.

Distances a and b as shown in FIG. 1B and the focal length of the relay optics can be chosen to arrange the magnification, therefore adapting the field of view such that the micro lens array 104 area maps onto the detector array 108 surface appropriately. This optical relay simultaneously allows spatial filtering for confocal detection when an aperture stop 107 is positioned in the Fourier plane of imaging optics 106. In the example shown in FIG. 2B, the focal length of the relay optics is 100 mm, distance a is 32 mm, and distance b is 100 mm. Other focal lengths and distances may be used as well. For example, the focal length may be between 70-130 mm, distance a may be between 20-50 mm and distance b may be between 80-102 mm.

The relative motion between the sample 101 and the micro lens array 104 is achieved, in some implementations, with a scanning stage 103 that translates either the glass window on which the sample 101 sits or the micro lens array 104 (or both) in order to record variations of the sample signal with the changing position and to reconstruct an image therefrom. The camera 108 is recording the image plane situated at the back side of the micro lens array 104. Therefore, every single micro lens signal is recorded simultaneously for a given position of the stage 103. At a given position during the scanning process, multi-point information is recorded from the sample 101 and the relative position of all these point on the sample 101 is precisely known. By repeating this multi-point acquisition along the controlled scan pattern, the relative intensity variations recorded from each micromirror in the array in relation with their respective position on the sample 101 can be reconstructed by a computing device (e.g., a computing device integrated in the reader or separate from the reader). This provides the image of the sample 101 situated in the focal plane of the micro lens array 104.

If the sample 101 is situated partially outside of the focal plane of the micro lens array 104, the signal intensity will drop in the corresponding region of the array. It gives topographic information of the distance separating the sample 101 from the focal plane of the micro lens array 104. A particularly valuable use of this topographic information is the compensation of a tilt angle between the sample plane and the micro lens plane. A computer may be used to control the reading instrument, including image reconstruction and/or displaying the image. In some implementations, control and reconstruction is embedded in the reading device.

In some implementations, the sample 101 is stained prior to processing using colored or fluorescent stains. For example, Proflavine, Acridine Orange, or other stains may be used. The staining procedure should remain simple to be executed in OR. For example, the staining procedure may comprise the steps: dip the tissue in a staining liquid, dip in a rinsing liquid, and then place the sample 101 on the glass above the micro lens array 104 for imaging. In certain embodiments, the sample 101 is placed in a sample holder 102 positioned above the micro lens array 104.

Figure 2A:
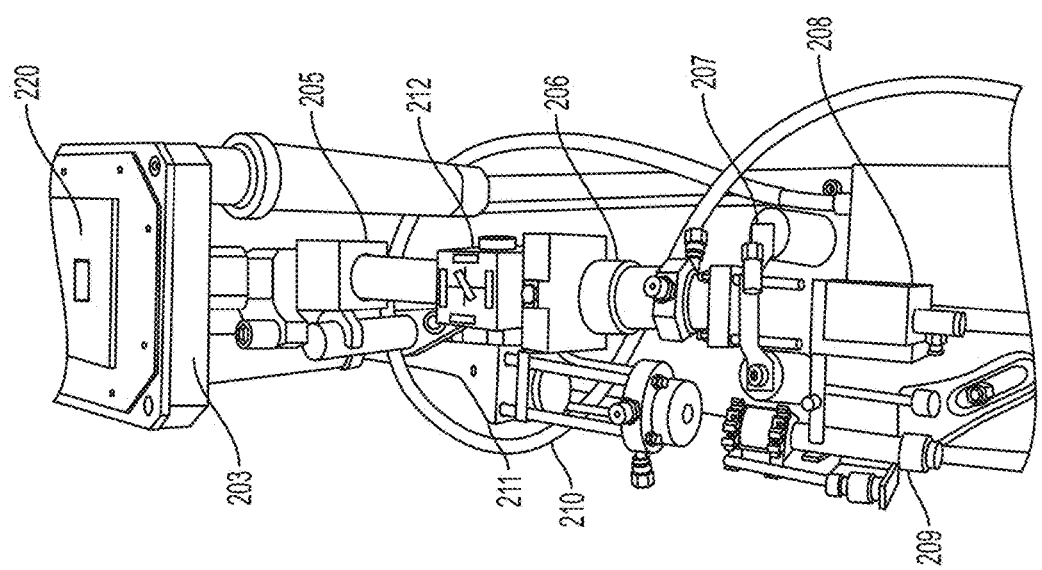
FIGS. 2A and 2B are illustrations and FIG. 2C is a photograph of an example system for in-operating-theatre of fresh thick tissue resected during surgery, in accordance with an embodiment of the invention.
Figure 2B:
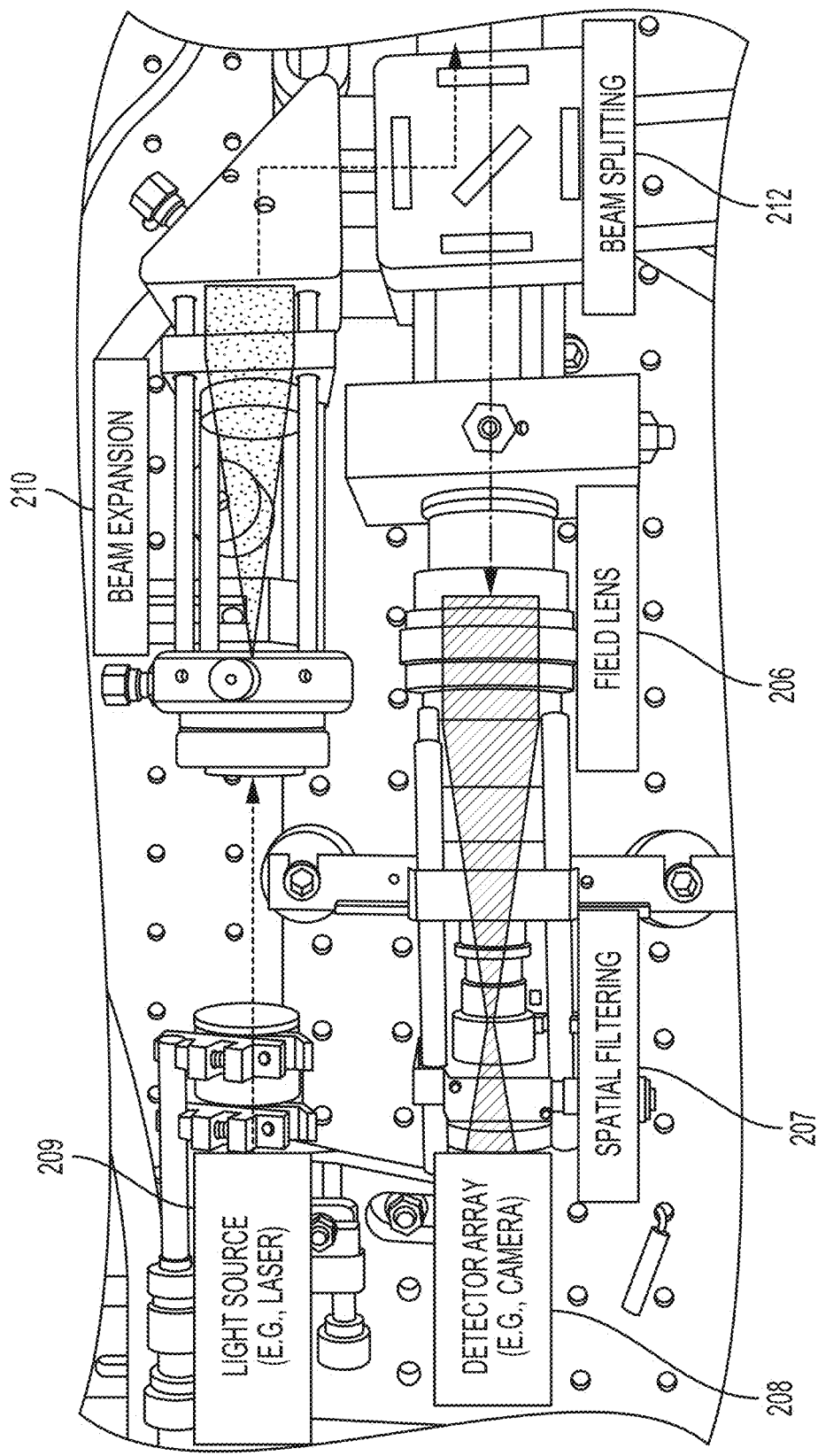
Figure 2C:
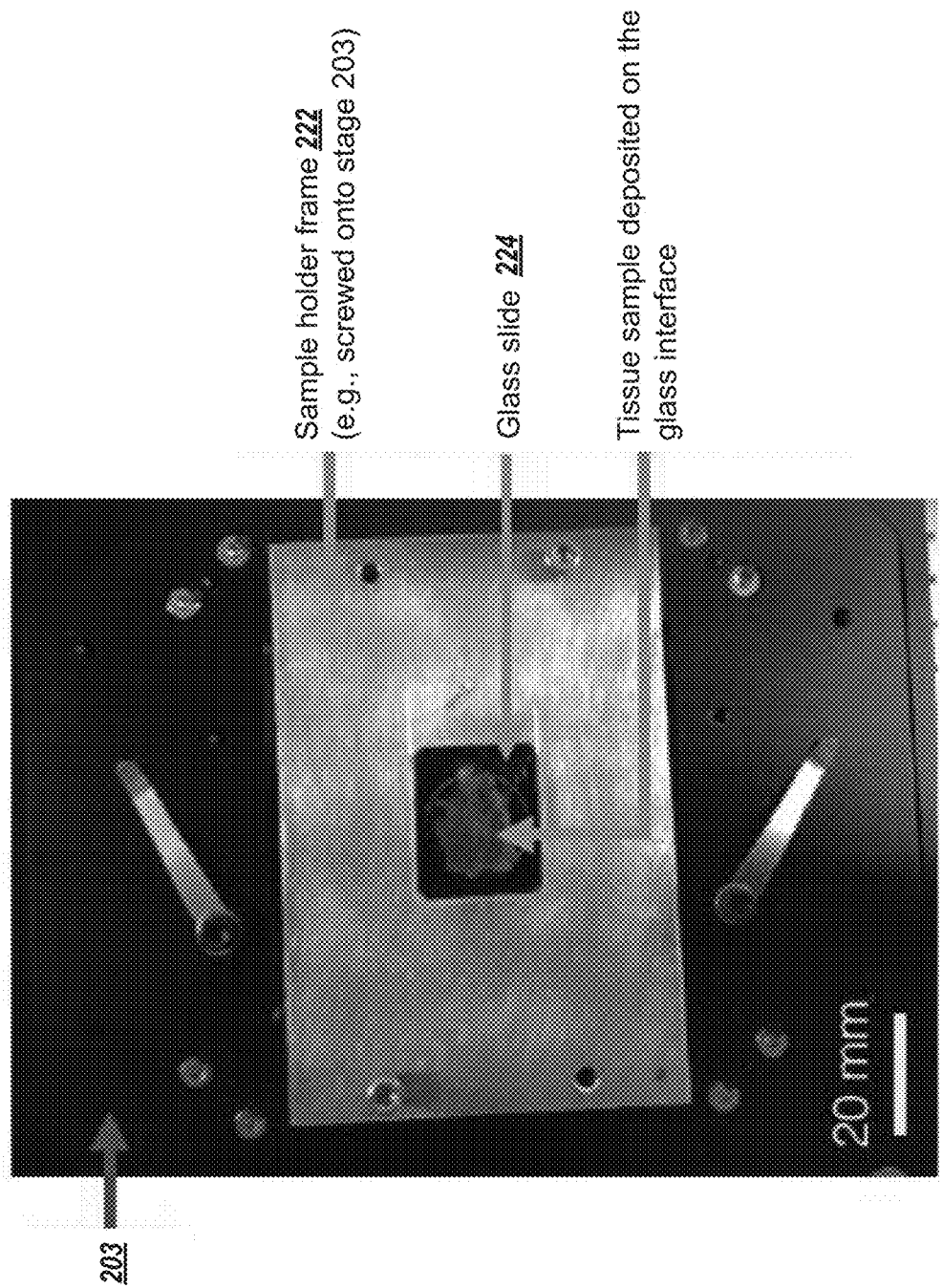

FIGS. 2A and 2B are illustrations and FIG. 2C is a photograph of an example in-operating-theatre pathology system in accordance with an embodiment of the disclosed technology. This example system uses a micro lens array to perform large-field high resolution microscopy and/or micro-projection of fresh, thick tissue in an operating theatre for pathology assessment. The illumination light is provided by a light source 209 (e.g., laser) and expanded by a collimating lens 210 (e.g., a beam expander). The collimated light is then directed onto a beam splitter 212 by a flat mirror 211.

The beam splitter 212 reflects the illumination beam (i.e., the unexpanded illumination beam or expanded illumination beam depending on whether a beam expander is used) to a micro lens array via a flat mirror 205. In this example, the beam splitter 212 is a dichroic mirror that separates light according to its wavelength (e.g., reflects the illumination beams and allows the collected fluorescence light to pass therethrough).

A micro lens array (underneath the scanning stage 203 in this example) focuses the illumination beam onto a sample (not shown) on the sample holder 220. The illumination beam is focused by each of the micro lens, producing an array of foci in the sample. The same micro lens array allows the light emitted from the sample (i.e., back-emitted light) as a result of the illumination to pass ultimately towards a detector array 208 (e.g., camera). The light emitted by the sample in response to the illumination is collected by each of the micro lens. In this example, the collected light then propagates as individual collimated beams.

In some implementations, the flat mirror 205 reflects the back-emitted light to the beam splitter 212. In contrast to the illumination beam which the beam splitter 212 reflects, the beam splitter 212 transmits the back-emitted light. After the back-emitted light passes through the beam splitter 212, a field lens 206 focuses the back-emitted light from the beam splitter 212 onto the detector 208 via an aperture stop 207, thereby imaging the micro lens plane onto the detector plane. The aperture stop 207 spatially filters the light, thereby rejecting out-of-focus light.

In this example, the relative motion between the sample and the micro lens array is achieved with a scanning stage 203 (e.g., 3×20×20 cm) that translates in order to record variations of the sample signal with the changing position and to reconstruct an image therefrom. At a given position during the scanning process, the global surface topography of the sample can be reconstructed by comparing the relative intensity variations recorded from each micromirror in array. A particularly valuable use of this topographic information is the compensation of a tilt angle between the sample plane and the micromirror plane. In this example, a computer (not shown) is used to control the reading instrument, including image reconstruction and/or displaying the image.

The system described in this example may be used for the observation of thick fresh tissue at a cellular level during surgery in order to provide pathology assistance to ongoing surgery. The sample may be processed using the disclosed technology in less than 10 minutes (e.g., less than 5 mins) using the system shown in FIGS. 2A-C in part because the sample does not need to be mechanically sliced as the disclosed microscopy may be used directly on fresh thick tissue (e.g., using optical slicing, a non-destructive method). Further, the pure technical speed of reading is improved and this approach preserves the sample such that it is available for definitive assessment (contrary of FSA). Additionally, images can be shared electronically which allows direct connection between the pathology and the surgery.

In this example, the sample holder 220 includes a sample holder frame 222 that is attached to the scanning stage 203. Specifically, in this example, the sample holder frame 222 is screwed to the scanning stage 203, although other attachment systems may be used. The sample holder frame 222 has a this transparent window 224 onto which the tissue sample is deposited for imaging. In this example, the transparent window 224 is glass.

Figure 3:
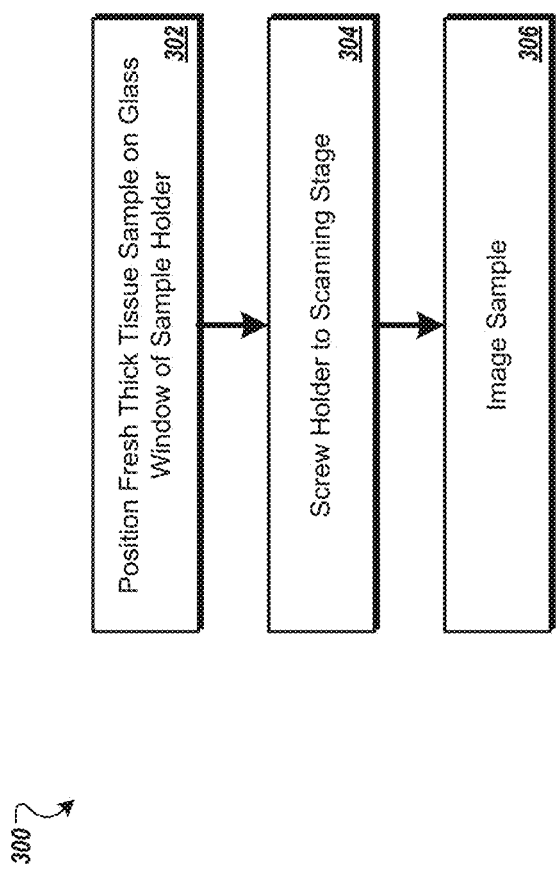
FIG. 3 is a flowchart of an example method for imaging a sample, in accordance with an embodiment of the invention.
Figure 4A:
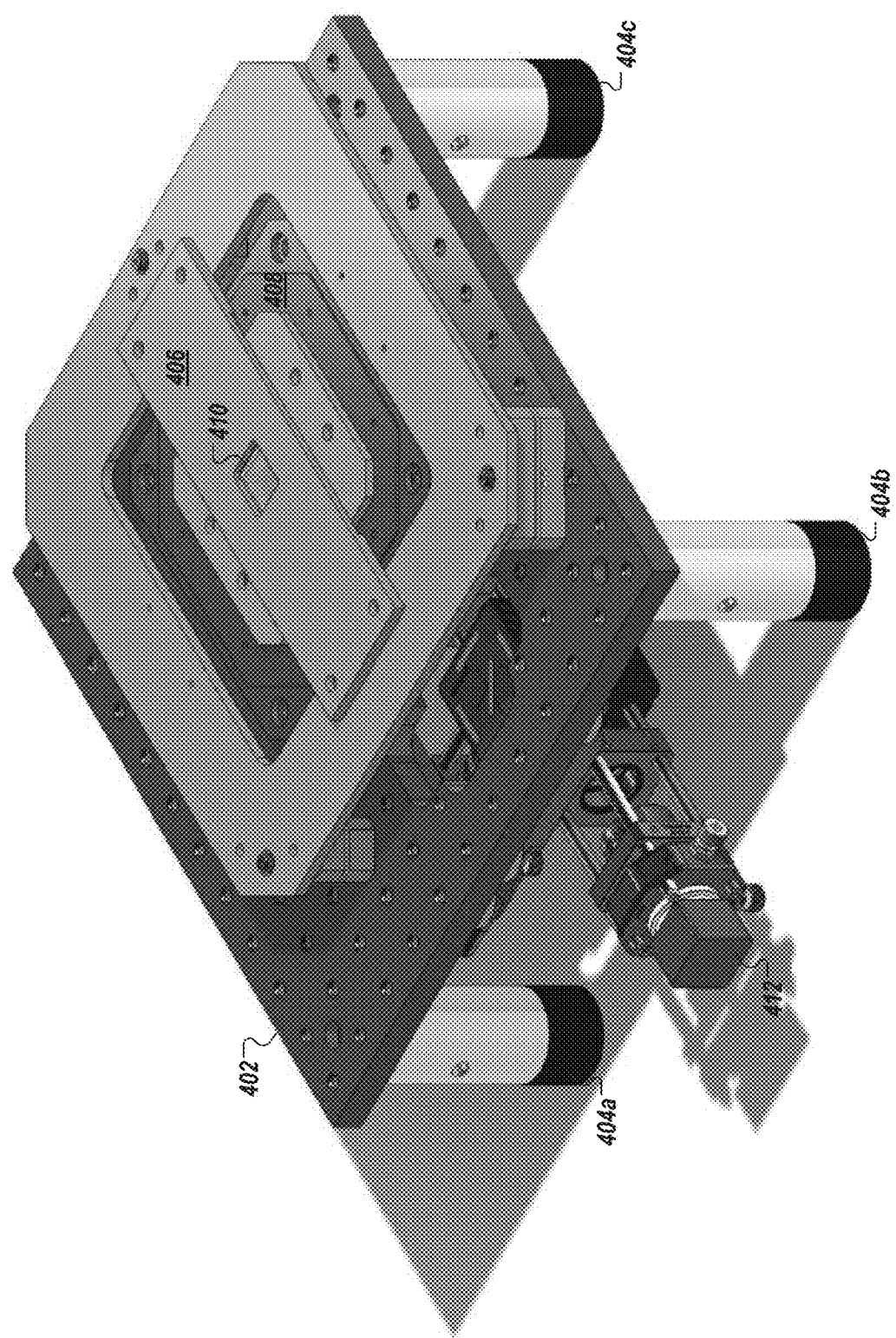
FIGS. 4A-G are illustrations of an example system for in-operating-theatre of fresh thick tissue resected during surgery, in accordance with an embodiment of the invention.
Figure 4B:
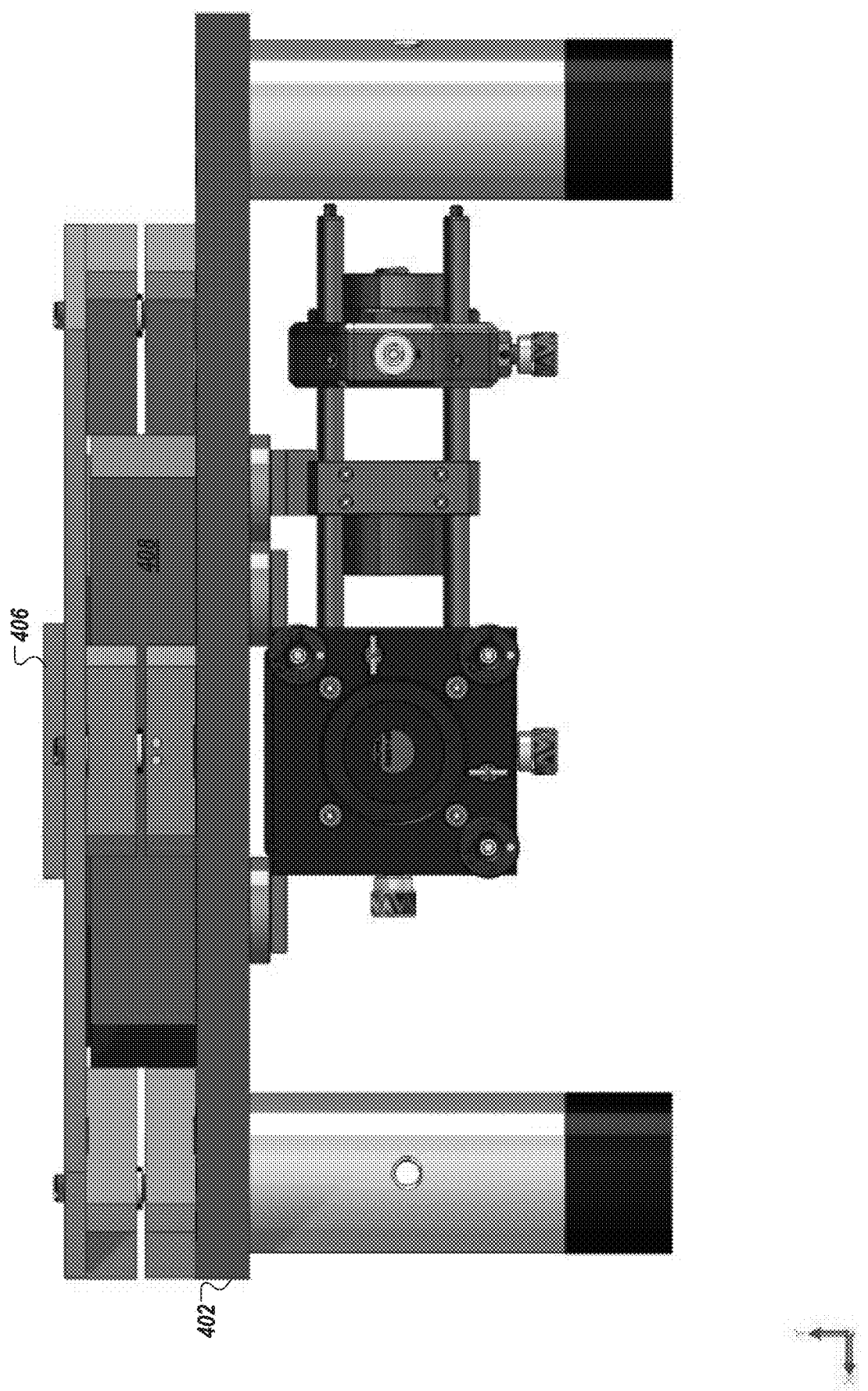
Figure 4C:
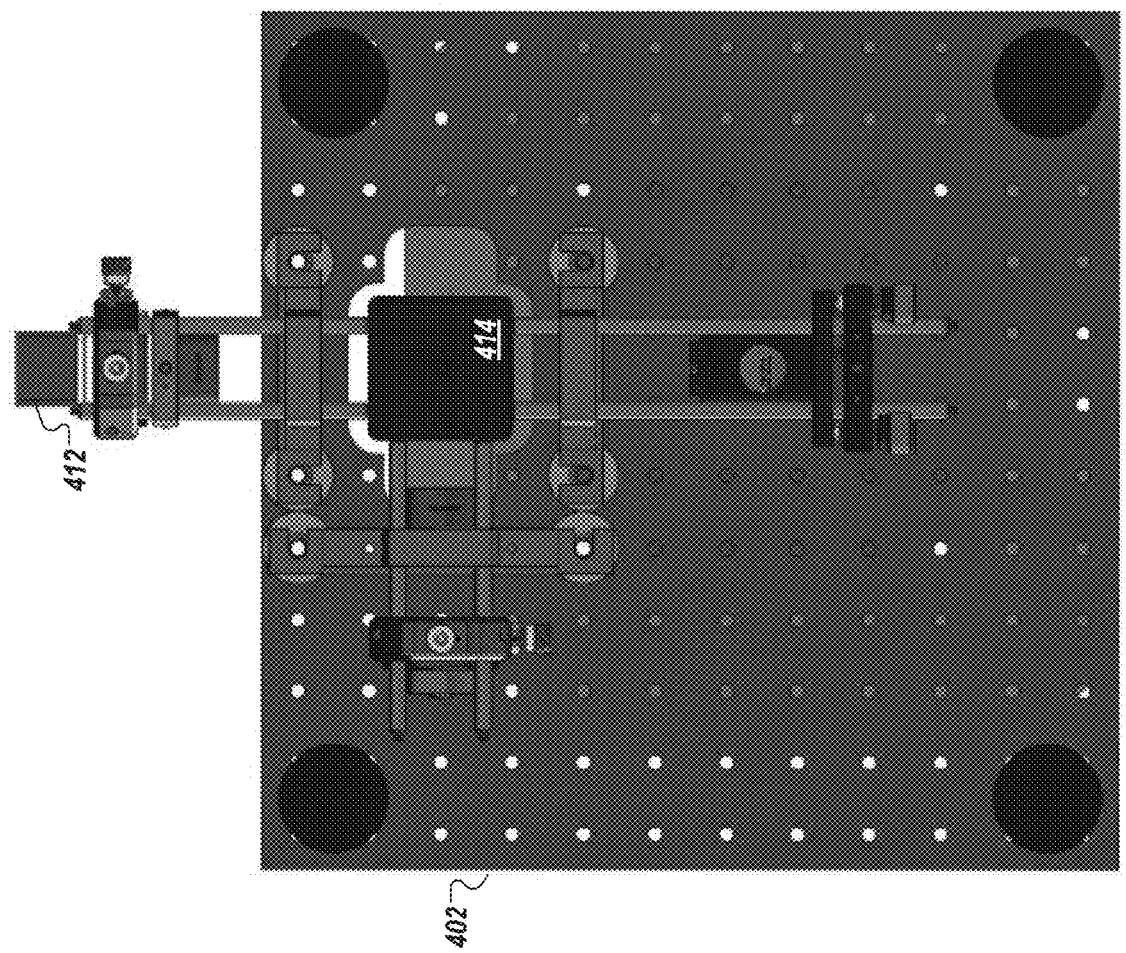
Figure 4D:
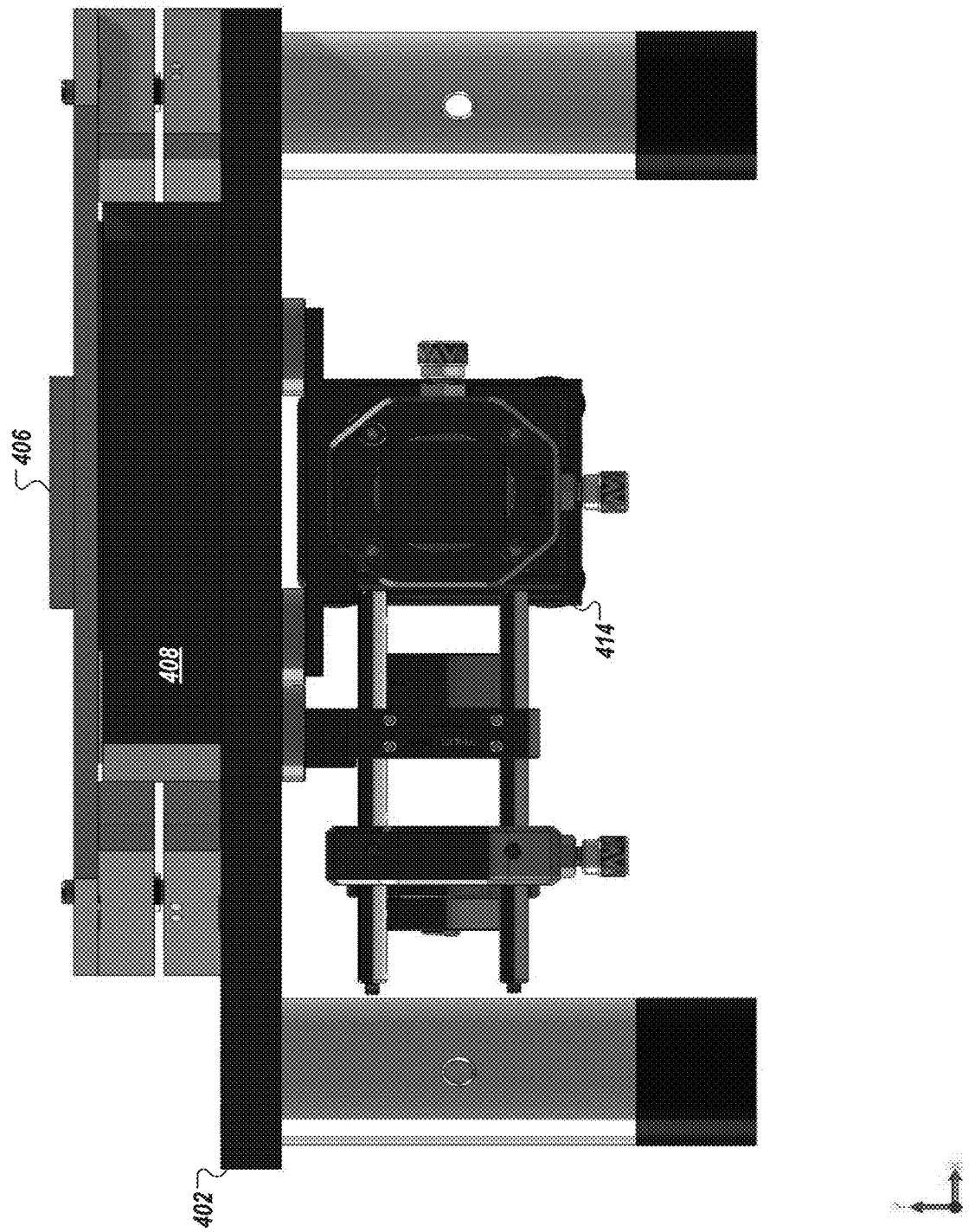
Figure 4E:
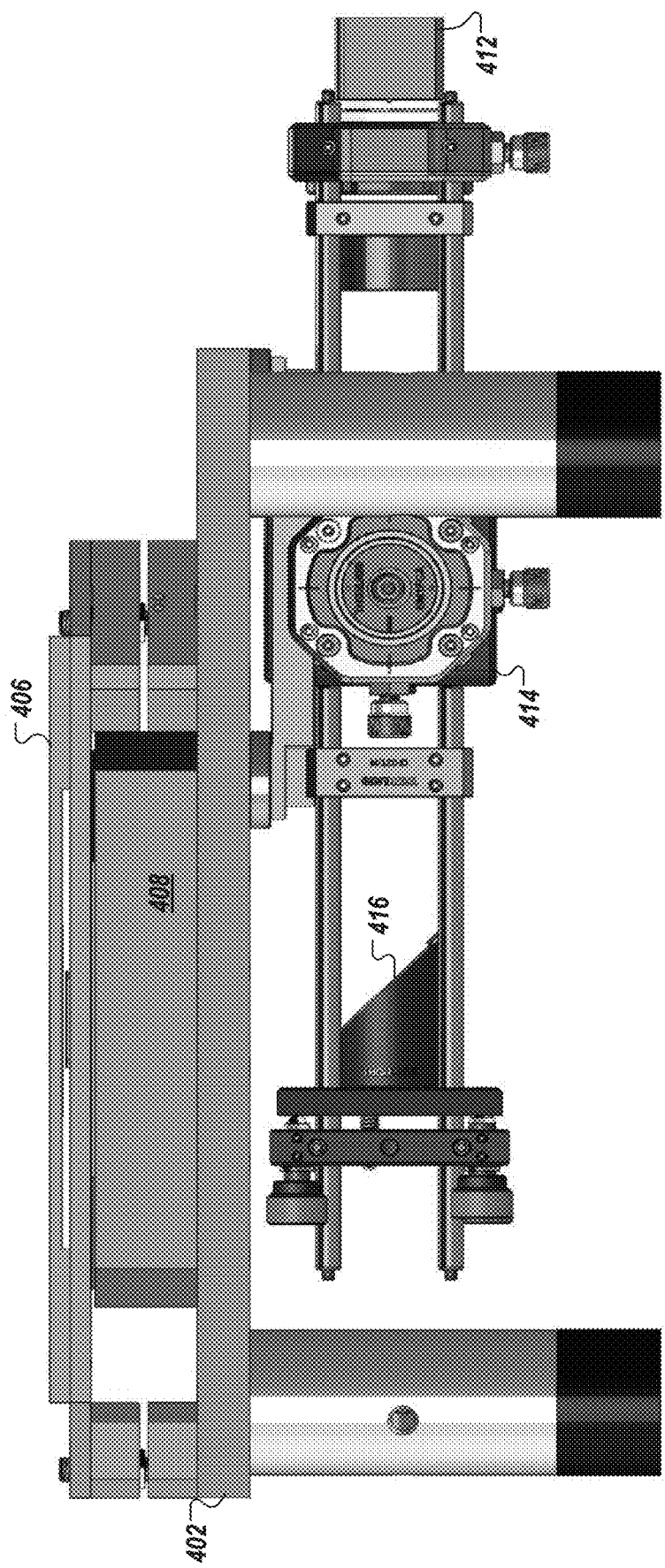
Figure 4F:
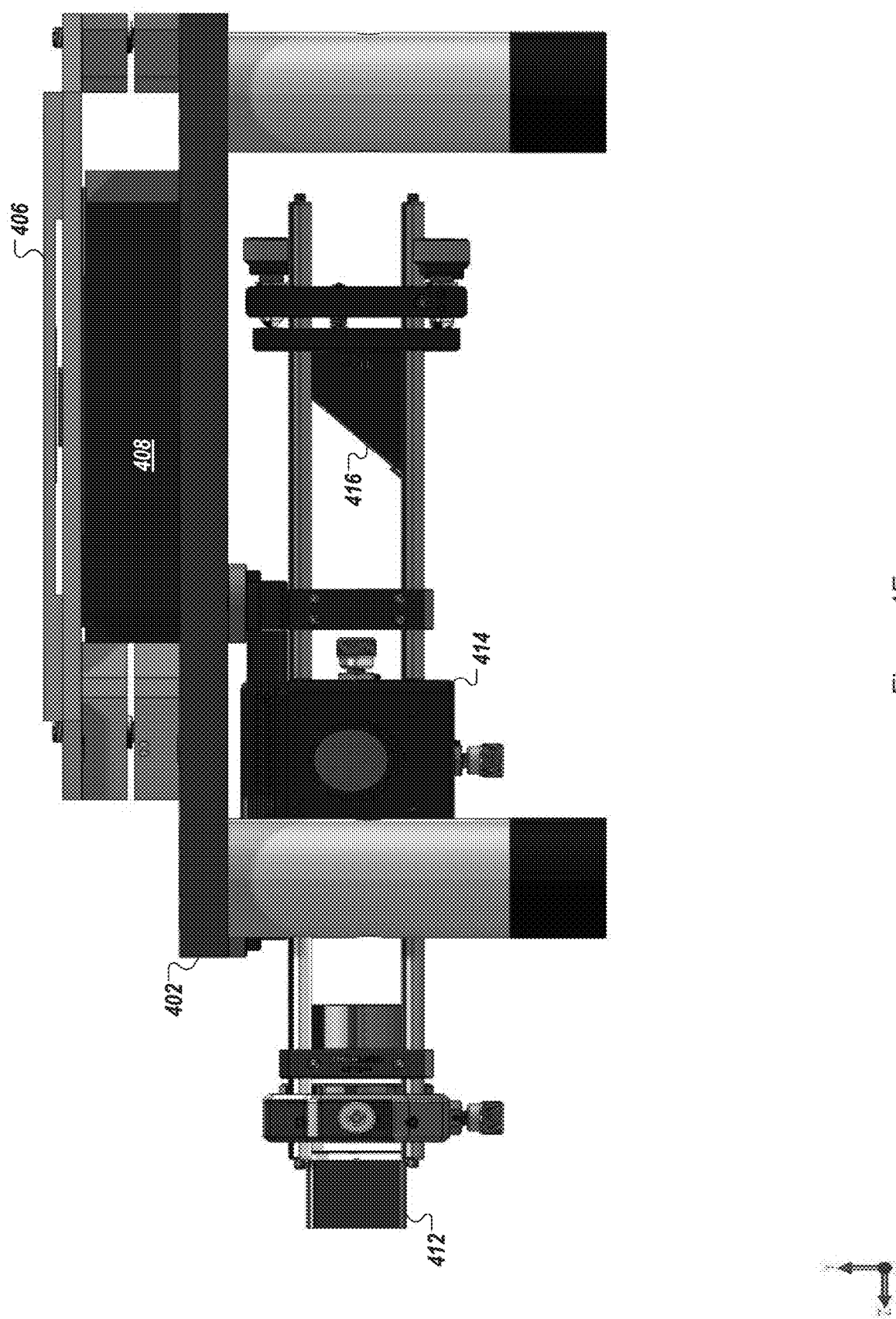
Figure 4G:
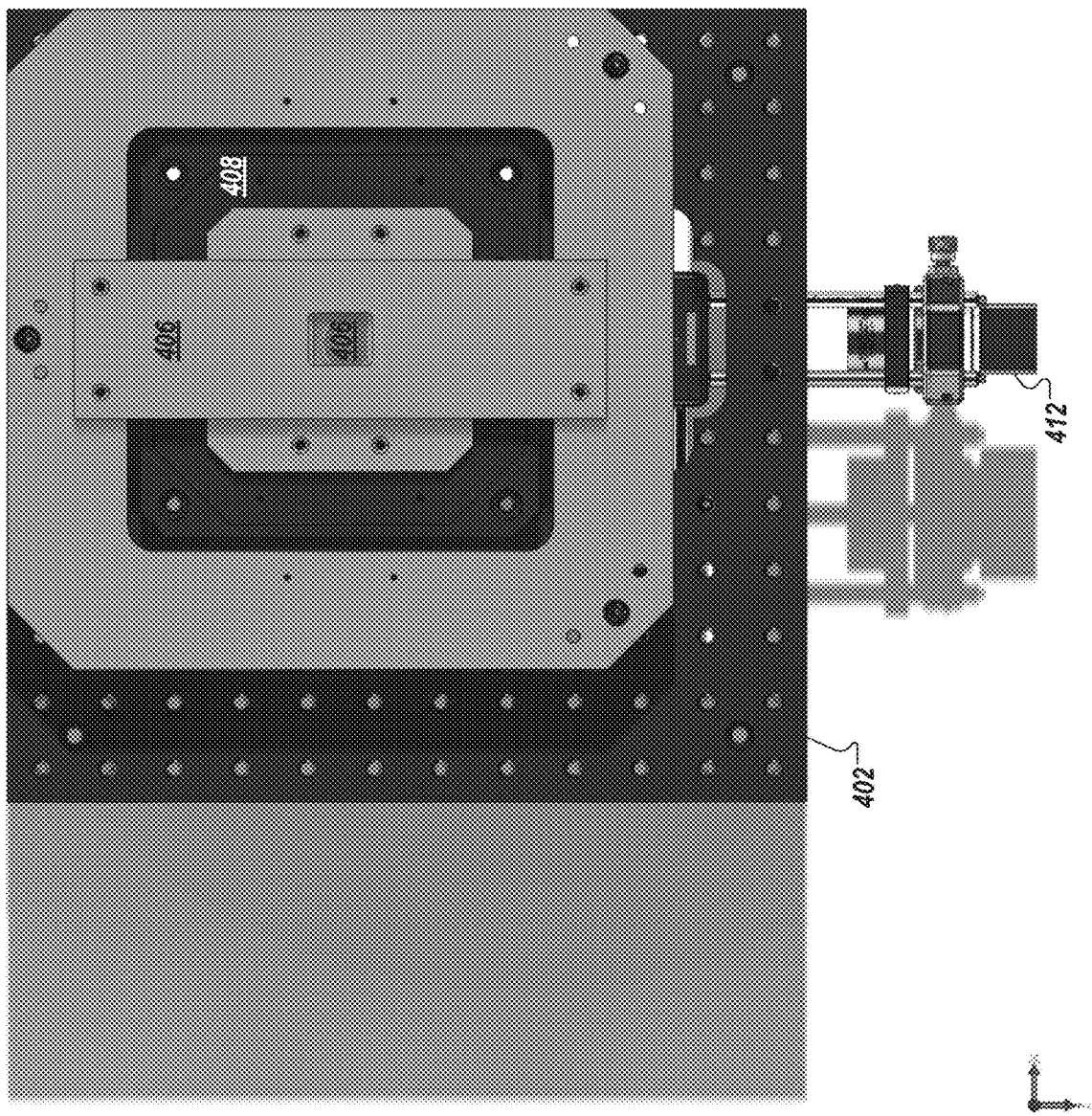

FIG. 3 is an illustration of a method 300 for imaging thick fresh tissue in the operating theatre. A fresh tissue sample (e.g., 101) is positioned on the glass window from the sample holder (e.g., 102) (e.g., after fluorescent labeling process is applied to the sample 101) (302). In some implementations, the holder (e.g., 102) is a metallic body (for cleaning or disinfection) with an opening window (e.g., 40×20 mm). The holder may be sealed at the bottom by a glass window for the instrument to be protected from liquid. In some implementations, the thin glass window secures an optical interface (transparent and flat) between the sample and the micro-optics chip. An example holder 220, window, and scanning stage 203 is shown in FIG. 2C.

The holder, in some implementations, is designed specifically for this application. The tissue may be put in contact with a thin glass slide (e.g., 50-100 μm thick) and gently pressed against the glass slide to secure the contact over the area to be imaged. In some implementations, the holder is sealed for specific cases where the tissue needs to be immersed in a liquid for clinical reasons. In some implementations, the holder is used for the staining procedure. In other implementations, the holder is a metallic plate with a hole in its center and a glued thin glass slide on the bottom.

In some implementations, the holder (e.g., 102) is screwed on the scanning stage (e.g., 103) (304). The stage, in some implementations, is a three-axis high precision positioning stage. The stage is used to bring the glass window in close proximity (e.g., <100 um) to the chip (e.g., 104). Then, the sample scan be imaged using the disclosed technology (306).

The disclosed scanning microscopy allows for fast confocal imaging over large area. For example, the disclosed scanning microscopy can be designed with a larger micro lens array to increase the field of view. In comparison, confocal microscope traditionally uses a configuration with a microscope objective and beam scanning. The field of view is limited (500 µm-1 mm) by the objective and highly dependent on the chosen magnification. The beam scanning increases the acquisition time for each image compare to standard microscopy. Consequently, to cover a 20 mm field of view for instance, a standard motorized confocal microscope would need to aggregate 400 to 1600 images in this example. The disclosed technology increases the speed, flexibility of use, robustness, ergonomics and compactness thereby achieving an in-operating—room scanning microscopy for imaging thick fresh tissue. The parallel approach described herein allows the disclosed technology to cover the field of view (e.g., of 20 mm) with a scan range corresponding to the pitch of the array (e.g., of 0.25 mm) while a sequential approach forces the scan to cover the entire field of view (2 orders of magnitude larger) which limits the speed, flexibility of use robustness, ergonomics and compactness.

In some implementations, the position of components in the system are fixed while only the sample is displaced (e.g., and in some implementations the scanning stage 103) by a translation fixture such that the sample may be scanned. In other implementations, the position of the sample relative to the system is fixed during scanning and the optical chip (e.g., micro lens array) is moved such that the sample is scanned. In this implementation, the image onto the detector will be moving, therefore the detected signal is processed to compensate for this movement. Further, in some implementations, the movement of the system during scanning is monitored to adjust the detected signal appropriately. Utilizing a moving optical chip rather than moving the sample itself while scanning eliminates any mobile component for the user to interact with and allows for a more robust external casing for cleaning and sterilization.

FIGS. 4A-G are illustrations of an example system for holding a sample. In this implementation, the sample holder is fixed and a mechanical translation stage moves the optical chip (e.g., micro lens array) relative to the rest of the system. In the example shown in FIGS. 4A-G, the main structure is supported by a base 402 (e.g., 300 mm×300 mm) and additional pillars 404a-c (collectively 404, post 404d not shown) (e.g., 100 mm tall). The global volume in this example is therefore 300 mm×300 mm×100 mm. Height may vary considering the height of the holding structure 406 for the sample (in purple here). Length may be increased (e.g., such that the camera is within the dimensions of the translation stage). Various dimensions may be used for the base 402 (e.g., width of 50 mm, 100 mm, 150 mm, 200 mm, or 250 mm, and lengths of 50 mm, 100 mm, 150 mm, 200 mm, or 250 mm, all values +/−50 mm) and the pillars 404 (e.g., 25 mm, 50 mm, or 75 mm, all values +/−25 mm).

The optical path is below the base 402, the scanning stage 408 is fixed on top of the base 402. The mechanical structure (e.g., 408 and 406) to hold the sample allows adjusting height and tilt of the sample relative to the stage and optical path. An optical window 410 (e.g., glass window) is located in the holding structure 406 such that a sample may be placed on the optical window 410 and a micro lens array positioned below the optical window 410 can focus light onto the sample and collect back-emitted light (e.g., fluorescence excited by the focused light) as described above. In some implementations, metal bars as shown in FIGS. 4A-G are provided such that the components of the system may be adjusted. In some implementations, the components are adjusted during manufacturing such that no further adjustments are necessary in the field. In other implementation, most of the adjustments are set during manufacturing, however, select fine adjustments may be made in the field.

This example system uses a micro lens arrays to perform large-field high resolution microscopy and/or micro-projection of fresh, thick tissue in an operating theatre for pathology assessment. The illumination light is provided by a light source and expanded by a collimating lens (e.g., a beam expander).

The beam splitter 414 reflects the illumination beam (i.e., the unexpanded illumination beam or expanded illumination beam depending on whether a beam expander is used) to a micro lens array via a flat mirror 416. In this example, the beam splitter 414 is dichroic mirror that separates light according to its wavelength (e.g., reflects the illumination beams and allows the collected fluorescence light to pass therethrough).

A micro lens array focuses the illumination beam onto a sample (not shown) on the sample holder. The illumination beam is focused by each of the micro lens, producing an array of foci in the sample. The same micro lens array allows the light emitted from the sample (i.e., back-emitted light) as a result of the illumination to pass ultimately towards a detector array 412. The light emitted by the sample in response to the illumination is collected by each of the micro lens. In this example, the collected light then propagates as individual collimated beams.

In some implementations, the flat mirror 416 reflects the back-emitted light to the beam splitter 414. In contrast to the illumination beam which the beam splitter 414 reflects, the beam splitter 414 transmits the back-emitted light. After the back-emitted light passes through the beam splitter 414, a field lens focuses the back-emitted light from the beam splitter 414 onto the detector 412 via an aperture stop, thereby imaging the micro lens plane onto the detector plane. The aperture stop spatially filters the light, thereby rejecting out-of-focus light.

Figure 5:
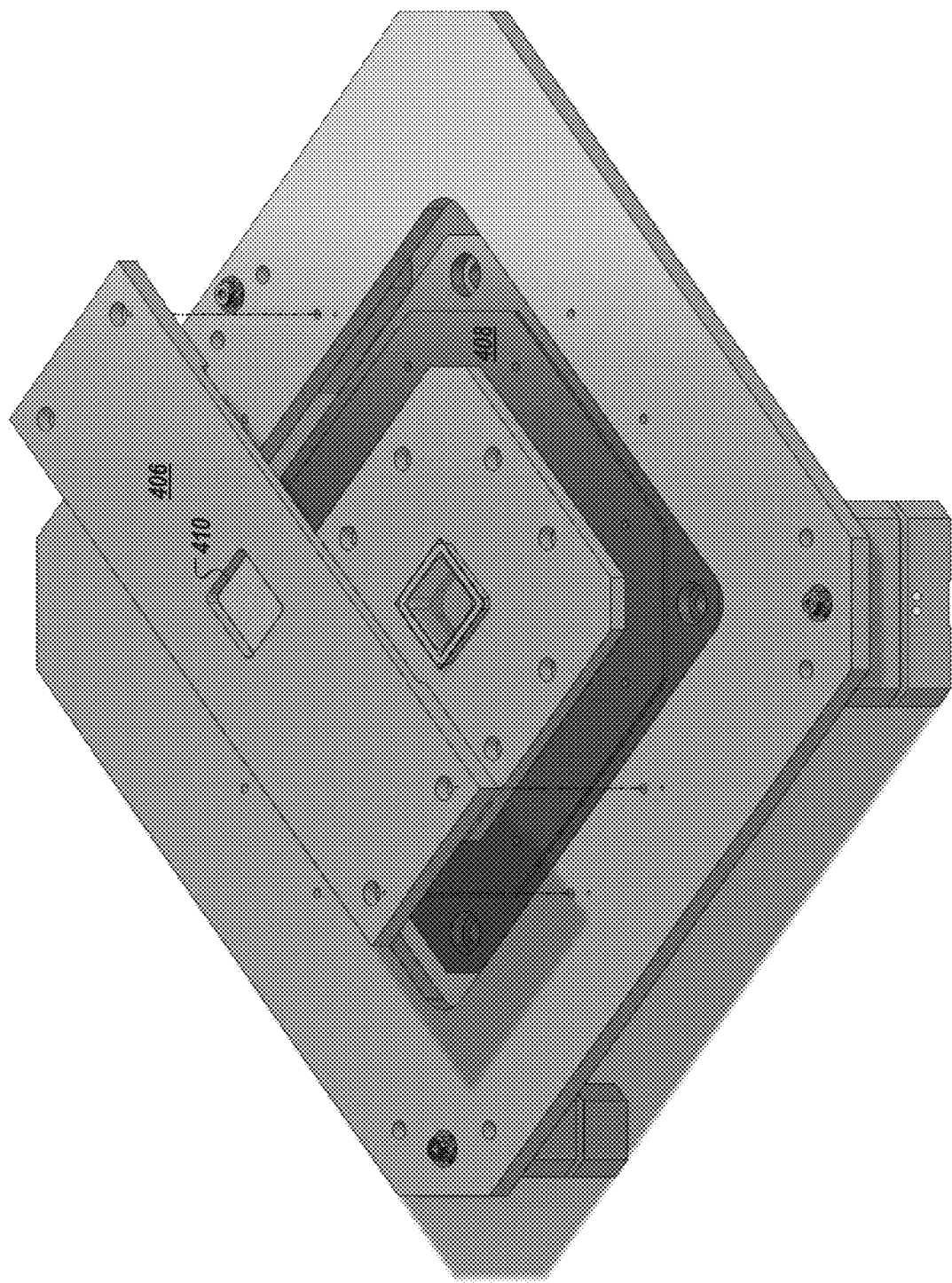
FIG. 5 is an illustration of an example sample holder, in accordance with an embodiment of the invention.

FIG. 5 is an illustration of an example sample holder system 500. In this example, the sample holder 406 is a metallic part including a thin optical window 410, which can be fixed on the system 500. This illustrates an "all combined" solution where the glass window tilt and height relative to the scanning stage/optical chip (not shown) can be adjusted as a manufacturing setup, assuring that any sample deposited on the optical window 410 will be correctly positioned regarding the microscopy system to be imaged.

Figure 6A:
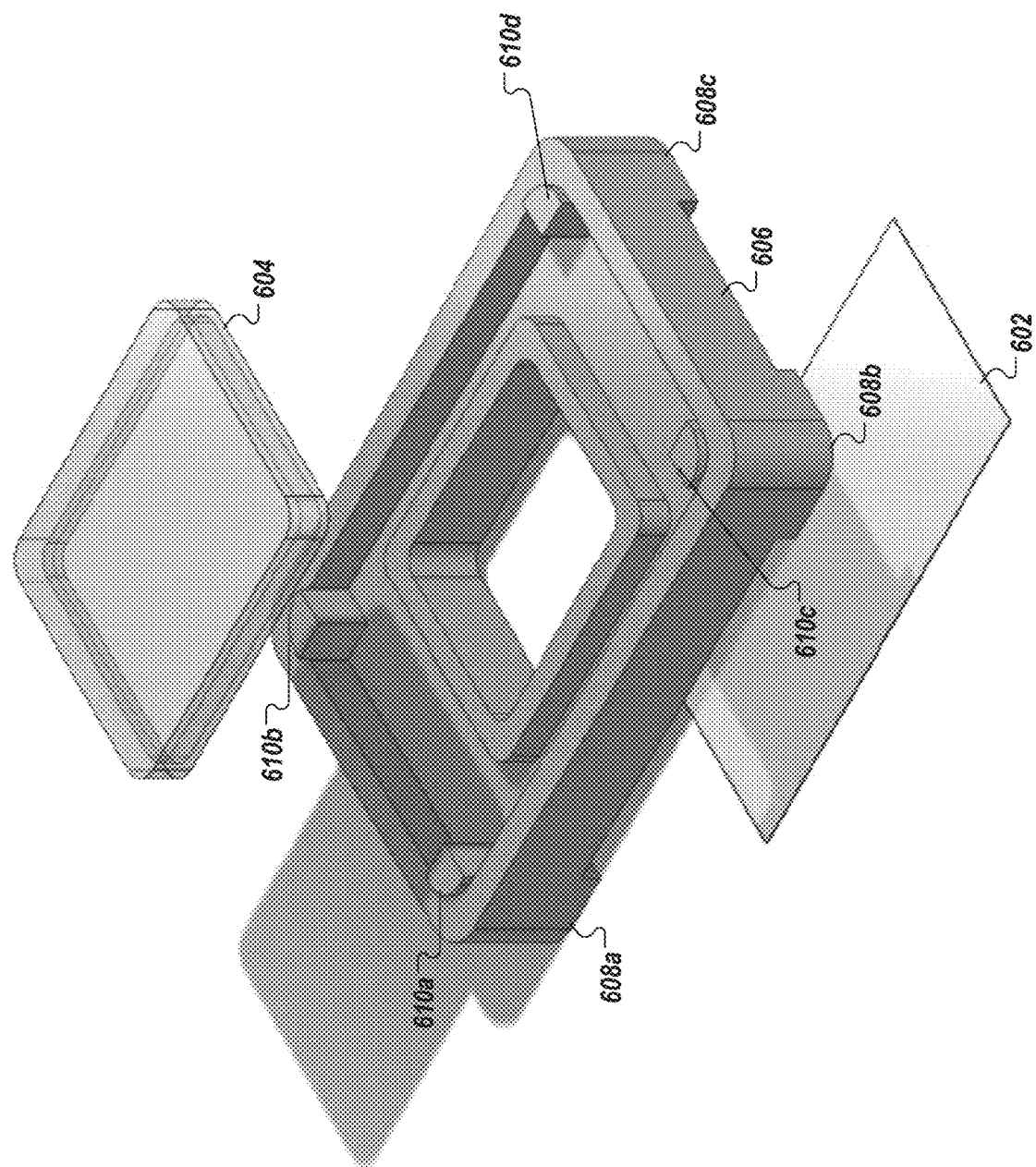

For sterility constraints due to dedicated application in clinical use (e.g., operating theater), it may be preferable to include a single use element (e.g., a disposable element). FIG. 6A shows an example of such a single use element 600 that can be inserted in the system for each use. The sample holder may be used as an adaptive element to secure the single use element 600 on the system at the right position for imaging. The single use element 600, in some implementations, includes a thin glass window 602 through which the imaging takes place. In some implementations, the element 600 includes a cover/lid 604 to protect the glass window 402 and enclose the sample once inserted into the body 606. The element 600 provides axial positioning repeatability (e.g., mechanical tolerancing, in some implementations, is better than 10 µm (e.g., 1 to 10 µm)). In some implementations, the element 600 is stackable with other similar elements. For example, the body 606 can include feet 608a-c (foot 608d not shown). Additionally, the body 606 can include storage guides 610a-d that allow elements 600 to stack on top of each other easily. The storage guides 610a-d are spaced inside of corresponding feet 608a-d from another element 600 such that the guides 610a-d laterally secure elements 600 when they are stacked on one another. In some implementations, the element 600 includes prominent feet 608a-c (foot 608d not shown) to preserve optical interface when, for example, putting the element 600 on a dirty or damaging surface.

Figure 6B:
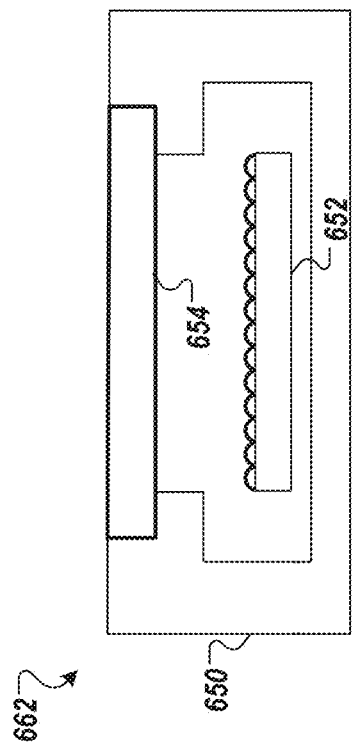
Figure 6C:
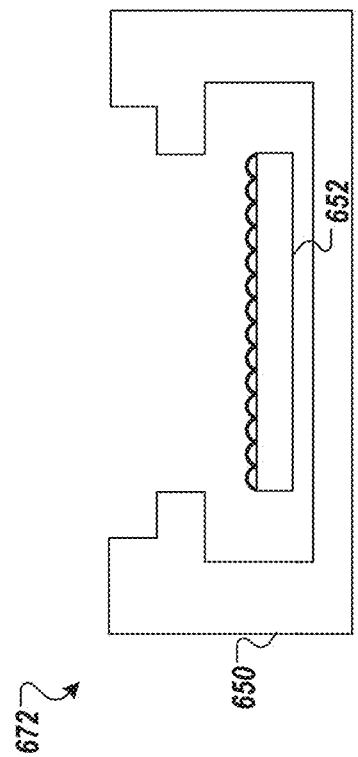

FIGS. 6B and 6C illustrate an additional sample holder 660 that can be used with an in-operating-theatre pathology system 662 (e.g., such as a system described herein). This example shows a system protected from environment (dust, liquid) by an external enclosure offering an opening window for imaging protected by a transparent material (such as glass). Such a system can be used for imaging without the sample holder 660 (e.g., disposable part), by directly placing the sample on the transparent window 654.

In the example shown in FIGS. 6B and 6C, the system 662 is a closed system and the sample holder 660 rests/sits on top of a plate 654 (e.g., transparent; e.g., made of glass or a polymer) that itself is attached to the body 650 of the system. The optical array 652 is housed within the body 650. For the purpose of this illustration, the entire body and system is not shown. As shown in FIG. 6C, even when the sample holder 660 is removed the system 662 is closed and the optical array 652 is protected from the environment. However, such a system requires multiple, stacked up interfaces (e.g., 654 and 660) and thus these interfaces must be thin and/or be optically transparent. In certain embodiments, the sample holder 660 is rigid, such as a polymer or glass. In other embodiments, the sample holder is flexible, such as a pellicle or film.

Figure 6D:
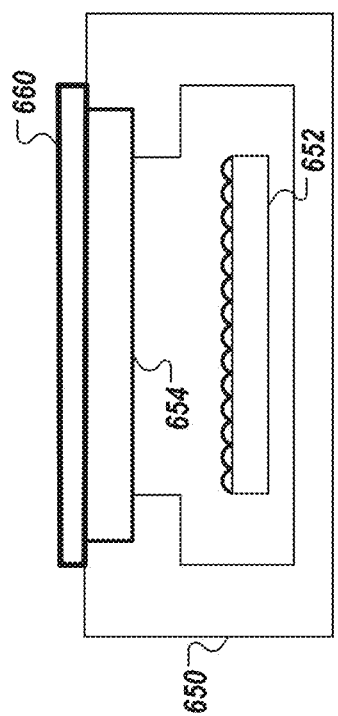
Figure 6E:
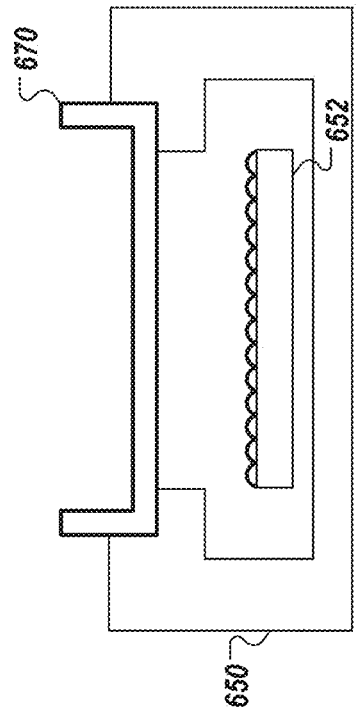
Figure 6G:
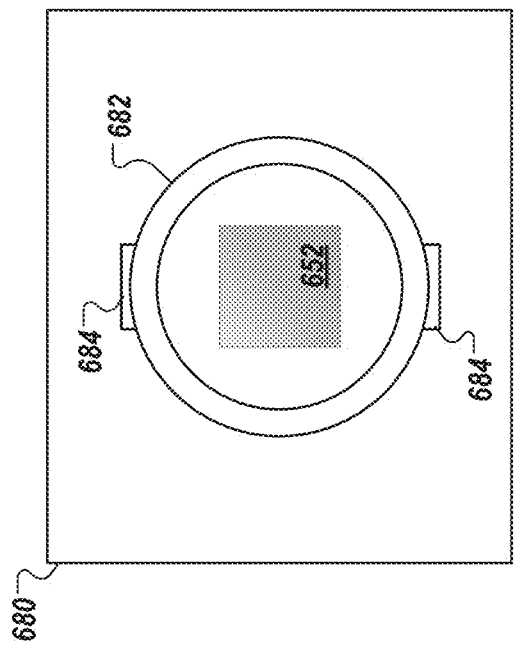
Figure 6F:
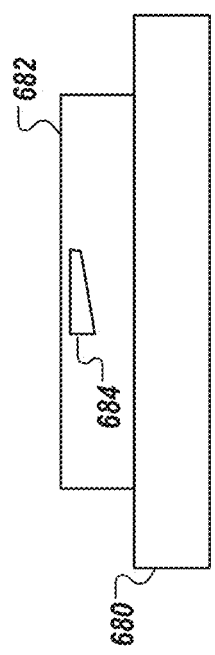

FIGS. 6D and 6E illustrate an additional sample holder 670 that can be use with an in-operating-theatre pathology system 672 (e.g., such as a system described herein). In this example, the system 672 is an open system as shown in FIG. 6E and the sample holder 670 (e.g., holder) rests, sits, or is attached to the body 650 of the system. The system is closed by a removable part 670. The optical array 652 is housed within the body 650. For the purpose of this illustration, the entire body and system is not shown. As shown in FIG. 6E, even when the sample holder 670 is removed the system 672 is open and the optical array 652 is not protected from the environment. However, the optical interface is thinner and/or has improved optical transparency as the only interface is on the removable part 670—there is no additional plate 654 as shown in FIGS. 6B and 6C.

The system shown in FIGS. 6D and 6E can includes a mounting system suited to accommodate the sample holder 670 (e.g., disposable sample holder) during an operation. In a surgical operation, for example, the tissue sample is placed on the sample holder 670 remotely from the system and then is brought to the system using the sample holder. In this example, the sample holder act as sample handler as well. The mounting system, in certain embodiments, has its own optical interface which is rigid to support tissue sample/specimen.

The mounting system for the sample holder (e.g., such as the sample holder shown in FIGS. 6A through 6E) can be one of a variety of systems. For example, the mounting system for the sample holder can require no fixation—instead, the sample holder is simply deposited (e.g., placed) on the top side of the instrument in the appropriate position such that the sample holder sits or rests on top of the instrument. In other embodiments, the sample holder can be secured using an adhesive, mechanical fixation (e.g., screws, clamp or any locking device), or one or more magnets to hold the disposable in position.

FIGS. 6F through 6J illustrates one example for mounting a sample holder 690 to a pathology system. In this example, only the optical chip 652 portion of the pathology system is shown. In certain embodiments, a support base 680 can be mounted on the pathology system. The support base can include a mount 682 with one or more protrusions 684 extending from the mount 682. In the example shown in FIG. 6F, the support base 680 includes two protrusions 684. The mount 682 is hollow on the inside and the support base 680 has a corresponding opening therein such that an optical chip 652 can scan a sample through the support base 680. This embodiment includes a second piece, referred to as a removable sample holder 690. The removable sample holder 690 includes a transparent window 692 through which the optical chip 652 can image a sample (e.g., the optical sensor is on one side of the transparent window 692 and the sample is on the opposite side of the transparent window 692). The removable sample holder 690 includes one or more interior protrusions 694. In this example, the removable sample holder 690 includes two interior protrusions 694. The width (labeled as 696 in FIG. 6I) of the vertical walls of the removable sample holder (excluding the interior protrusion(s) 694) is such that it can slide over the mount 682 when the protrusion(s) 684 and interior protrusion (694) are not aligned. Once the removable sample holder 694 is fully applied to the mount 682, the removable sample holder 694 can be twisted (e.g., clockwise in this example) such that the protrusion(s) 684 and the interior protrusion(s) 694 are engaged with each other. This securely mates the removable sample holder 694 to the support base 680 such that the optical sensor 652 can image a sample placed on the transparent window 692 in the removable sample holder 694.

Figure 7:
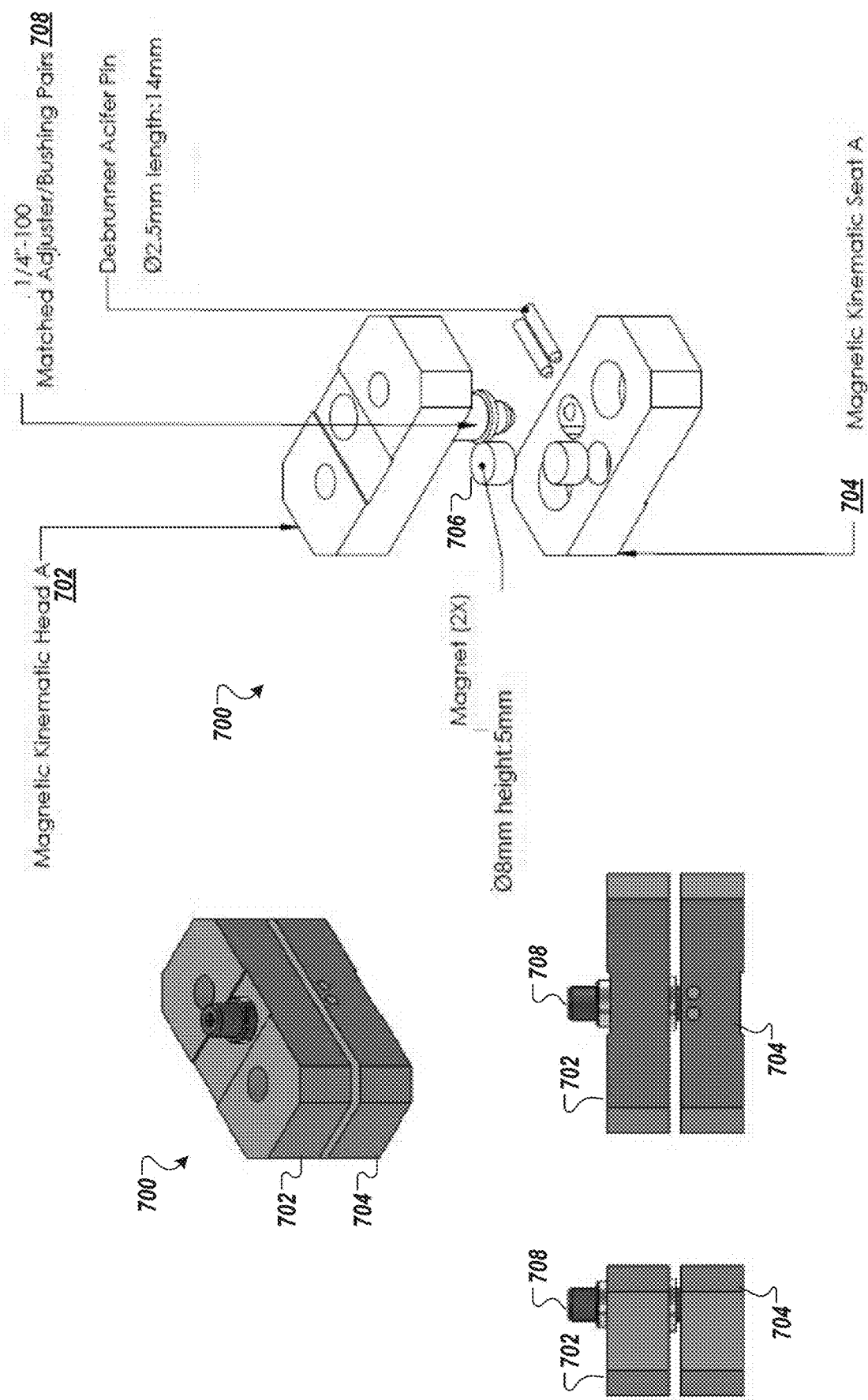
FIG. 7 is an illustration of an example structure for adjusting both height and tilt of the glass window (e.g., by moving the scanning stage) relative to the optical chip and corresponding optical path with an embodiment of the invention.

FIG. 7 is an illustration of an example kinematic structure that is used, in some implementations, for adjusting both height and tilt of the glass window (e.g., by moving the scanning stage) relative to the optical chip and corresponding optical path. In certain embodiments, the kinematic structure has three feet (although different numbers of feet may be used such as 2, 4, or 5) with adjustable height (micrometric screw—see FIG. 7 kinematic base 700 holding the frame on which can be screwed the sample holder). The purpose of this kinematic base 700 is to adjust both height and tilt of the glass window (e.g., glass window 604 in FIG. 6 or optical window 410 in FIG. 4A) relative to the optical chip (e.g., optical chip 902 in FIG. 9 or micro lens array 104 in FIG. 1A) and corresponding optical path. The two surfaces (e.g., the glass window and the optical chip), in some implementations, have an area of about 20 mm by 20 mm (other dimensions may be used, such as a width of 10-60 mm and a length of 10-60 mm) and will be positioned at a close distance less than 500 µm (e.g., less than 400 µm, less than 300 µm, less than 200 µm, and/or greater than 100 µm, greater than 200, and/or between 100-200 µm, 200-300 µm, 300-400 µm, or 400-500 µm), which may require adjustment of these settings (e.g., during manufacturing). Additionally, the microscope performances are increased when all surfaces are positioned normal to the optical axis of the system. In the example shown in FIG. 7, the kinematic base 700 includes a magnet 706 (e.g., a pair of magnets may be used—a magnet in the seat 704 that is magnetically attracted to a magnet in the head 702) that exerts a force that aligns and maintains the head 702 in position on the seat 704. The height and tilt is defined by the distance between head 702 and seat 704, which is controlled with the adjuster screw 708 (e.g., ¼"-100). In an example that uses three kinematic feet, one kinematic foot may be screwed in to increase the distance between the respective seat 704 and head 702 and modify the global tilt and height of the platform standing on these feet. In this example, if all three kinematic feet are screwed with the same number of rotations, all feet height change the same way, which gives a pure platform height change. Otherwise, if the kinematic feet are not all screwed with the same number of rotations, the tilt is modified.

Figure 8:
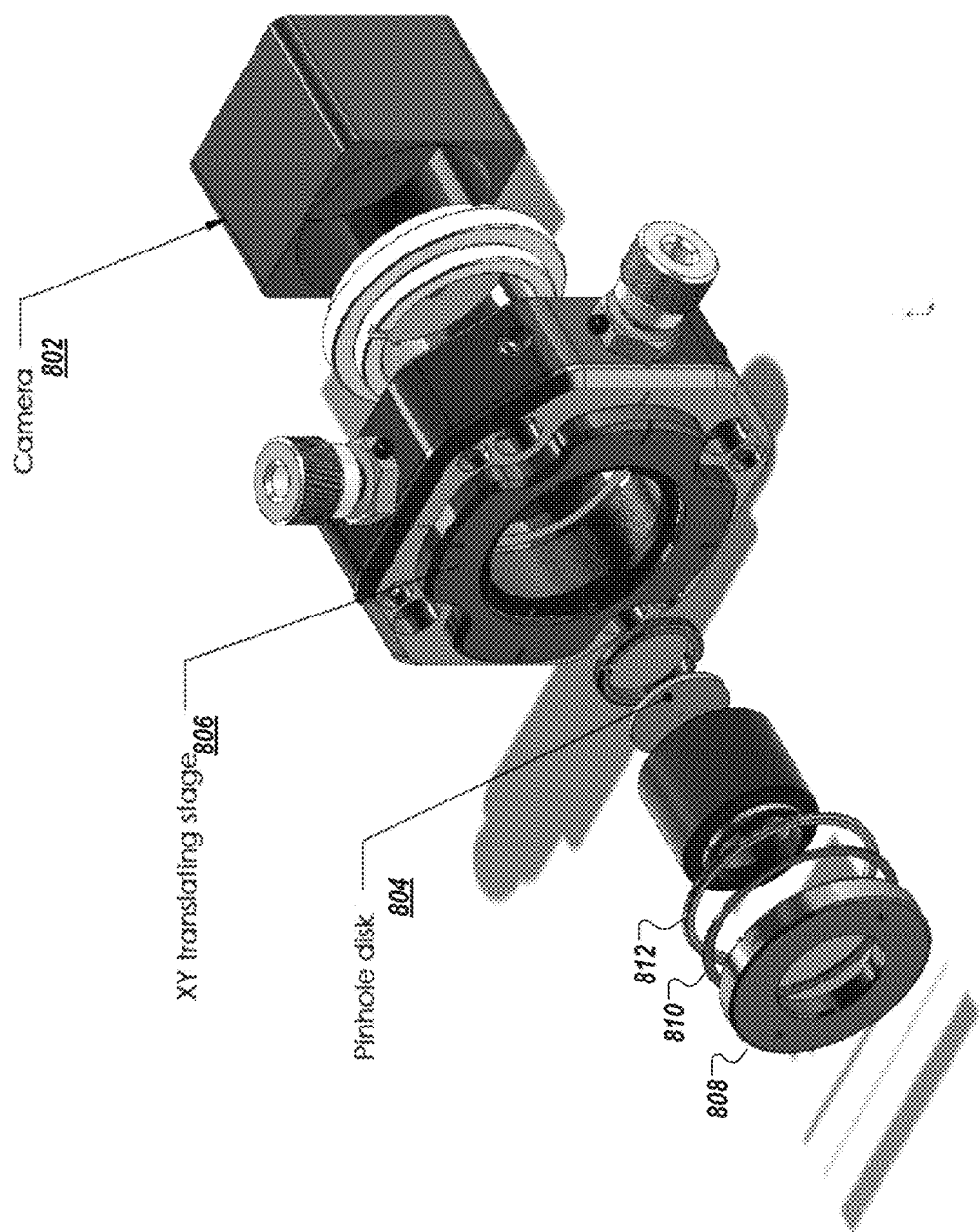
FIG. 8 is an illustration of an example camera and pinhole assembly, in accordance with an embodiment of the invention.

FIG. 8 is an illustration of a camera 802 and pinhole 804 (e.g., aperture) assembly. The axial distance between the pinhole disk 804 (i.e., aperture stop) and the detector 802 (e.g., camera sensor) is determined from optics equations and is not extremely sensitive in terms of tolerances so it can be determined and mechanically set without the need for fine adjustment. Fine position, however, in certain embodiments, is required for the lateral position of the pinhole in the disk 804. In certain embodiments, this requirement is provided using the system shown in FIG. 8. In FIG. 8, the position of the aperture stop relative to the optical axis is adjusted with an XY translating stage 806, while the camera 802 has a fixed position relative to the optical axis. The aperture stop 804 (pinhole) is used to filter the collected light on a confocal manner before the light signal reaches the camera 802 sensor. The position of this aperture 804 is of importance as it selects the points of origin of the light collected in the sample. Adjusting this pinhole (i.e., small hole in the disk 804) position corresponds to adjusting the position of the grid of collected focal points in the sample. For maximizing the performance of the confocal microscope this collection grid must be aligned (match) with the illumination grid. This aperture 804 positioning is critical for correctly setting up the system.

Figure 11A:
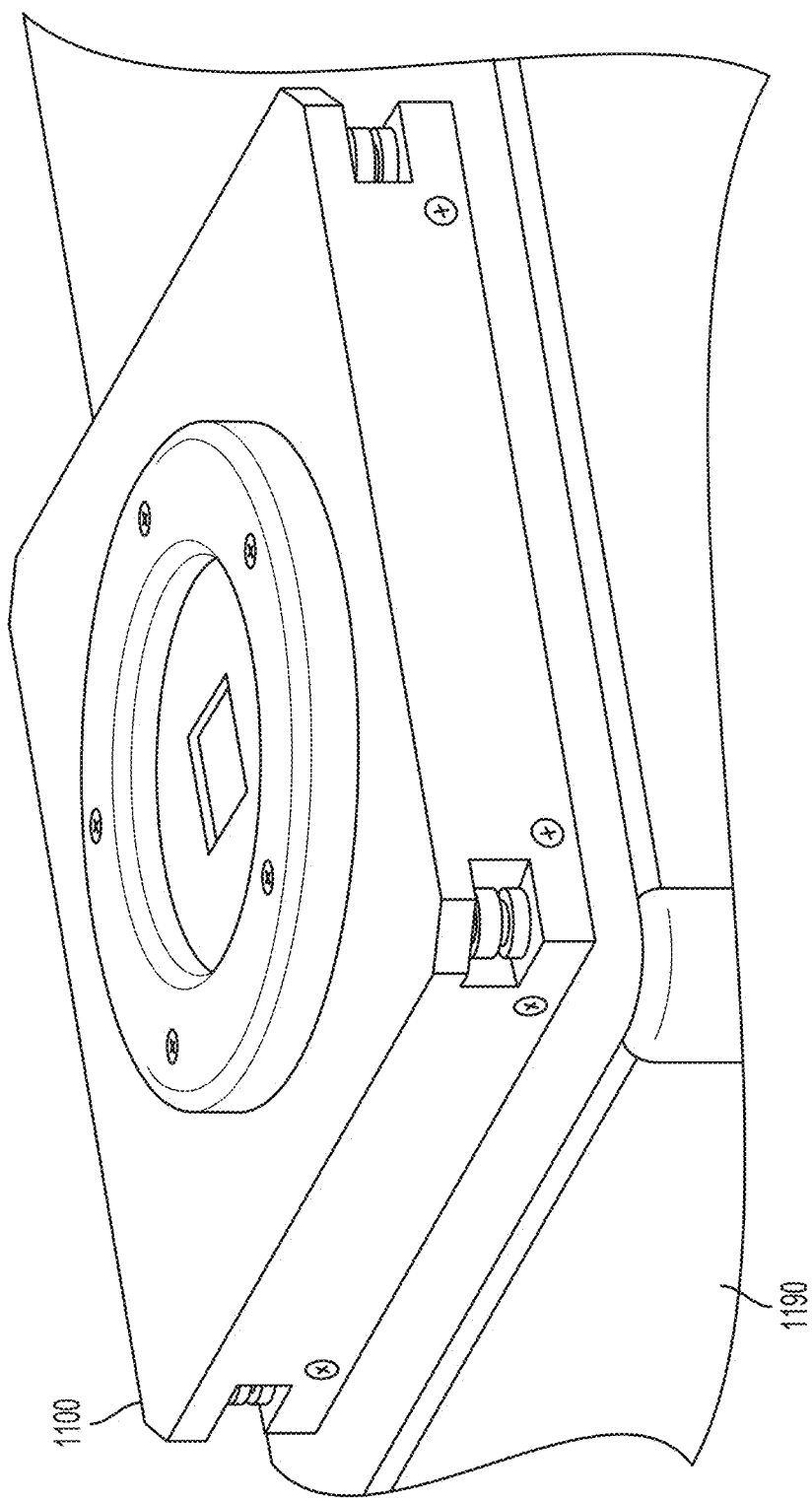
FIGS. 11A through 11C illustrate an example implementation of a specimen imaging area, in accordance with an embodiment of the invention.
Figure 11B:
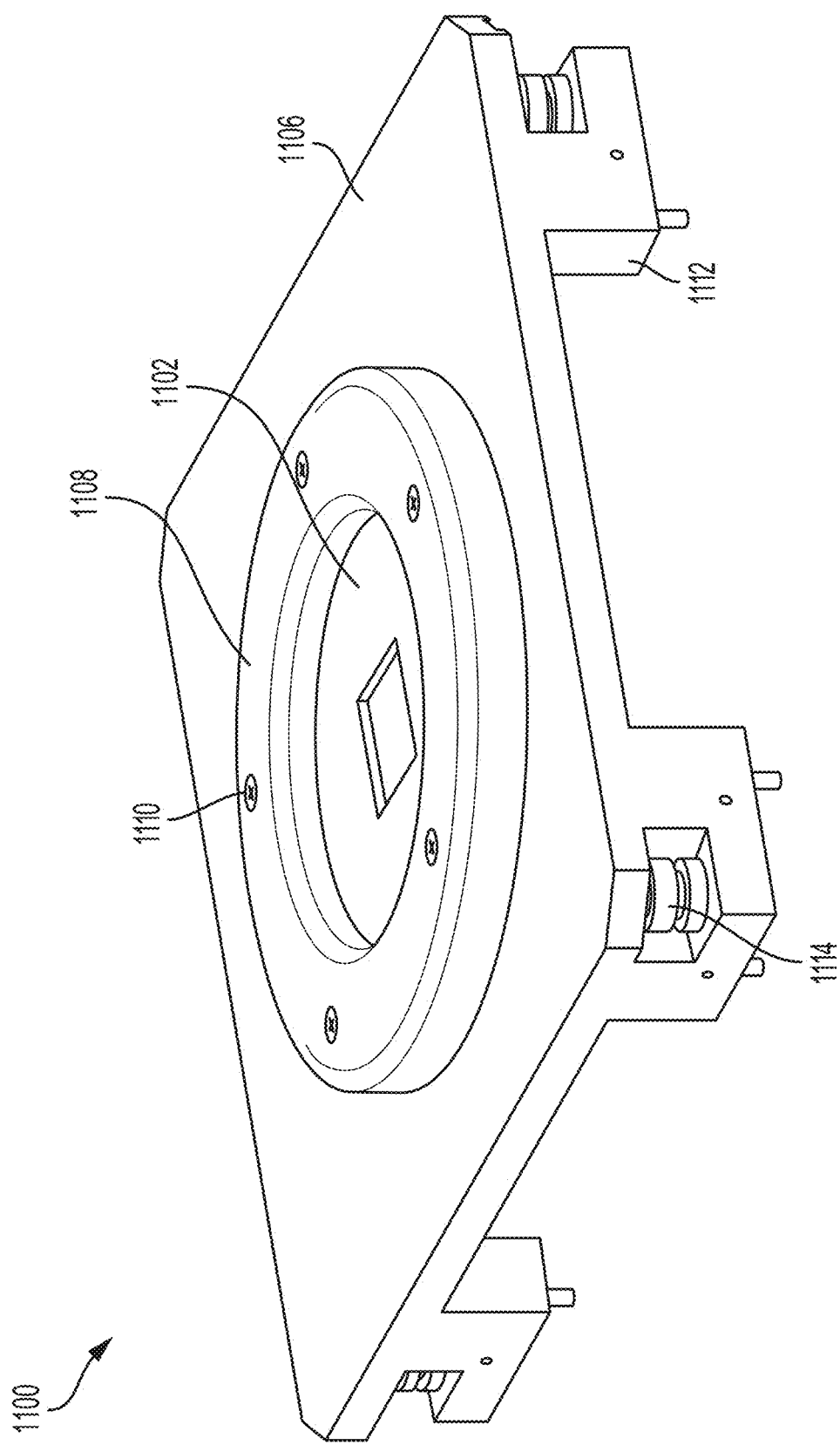
Figure 11C:
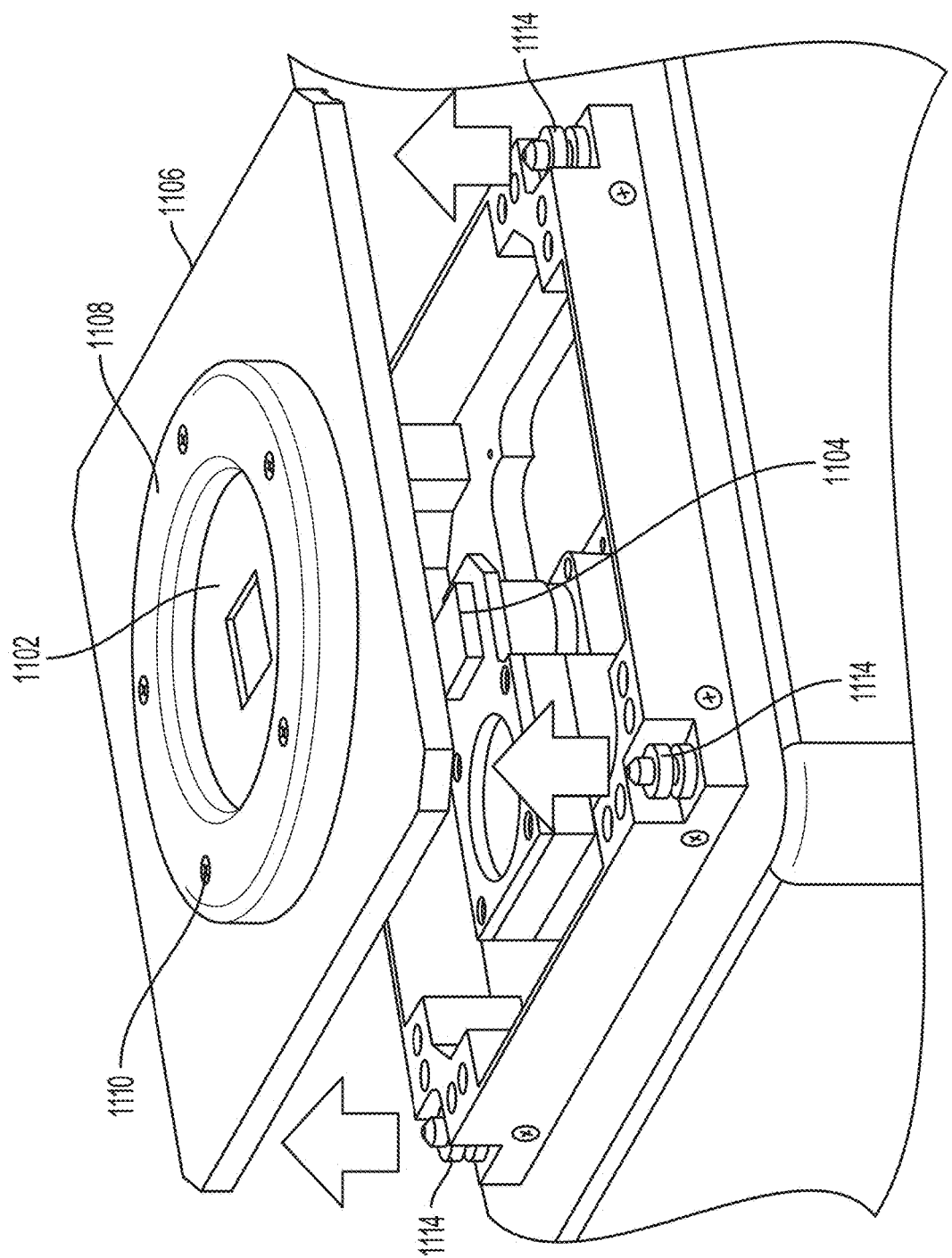
Figure 11D:
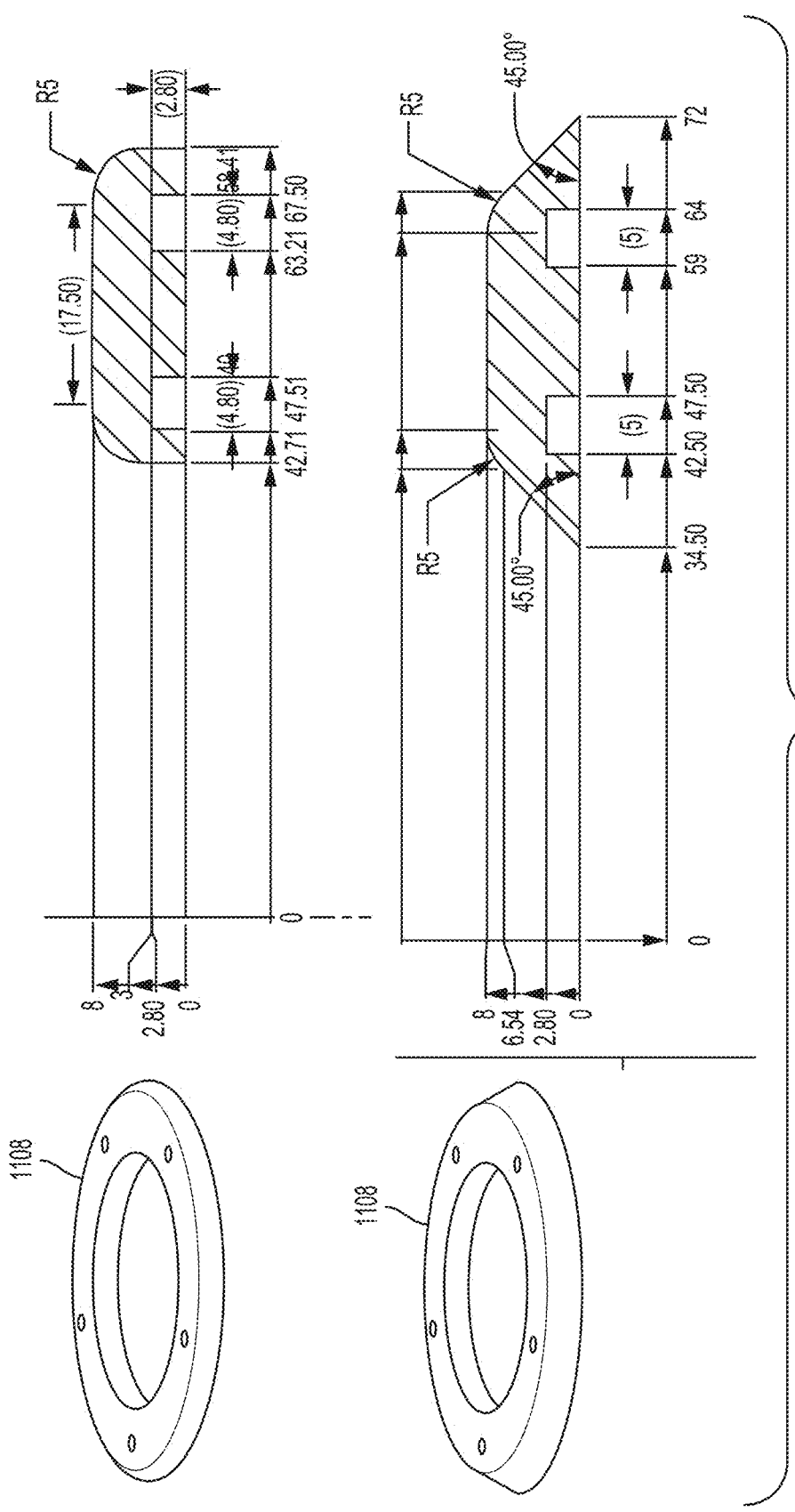
FIG. 11D is an illustration of example optical interface clamps, in accordance with embodiments of the invention.

Also illustrated in FIG. 8 is the optical interface clamp 808 (e.g., 1108 shown in FIG. 11D). The optical interface clamp 808 is a ring-shaped part (although other shapes can be used) that maintains the optical interface 810 (e.g., transparent window) in place against the optical interface mount (e.g., 1106 in FIG. 11B) and that seals the device with O-ring gaskets 812. In certain embodiments, the optical interface clamp 1108 is designed to be in contact with the specimen while preventing the optical interface mount 1106 from contacting the specimen during use.

Figure 9:
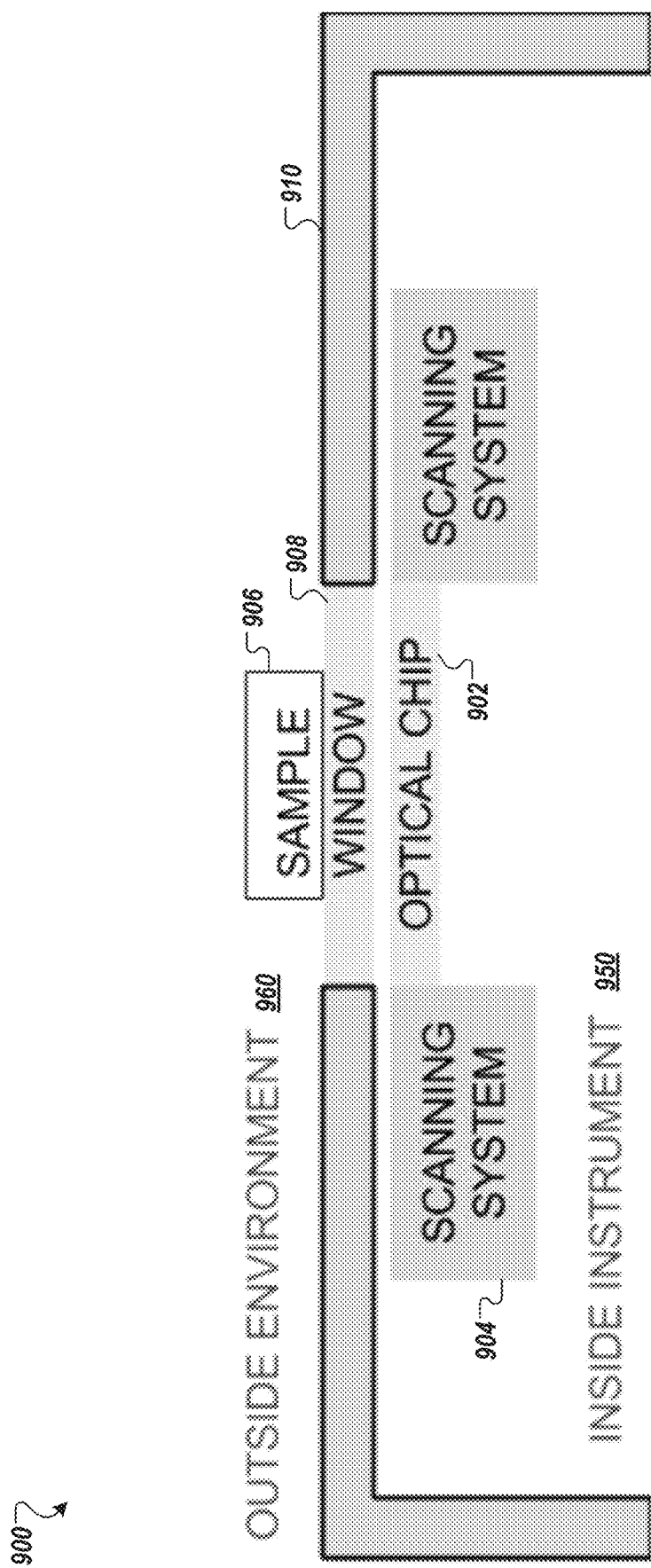
FIG. 9 is an illustration of an example optical chip scanning system, in accordance with an embodiment of the invention.

FIG. 9 is an illustration of an example optical chip scanning system 900 that may be used with the optical system described above. In this example, the optical chip 902 is moved by a scanning system 904. In the example shown in FIG. 9, the scanning system 904 and optical chip 902 are in an interior environment 950 of the instrument (e.g., fully or partially enclosed in the instrument) such that the optical chip 902 is protected from both the sample 906 and, in some implementations, outside environment 960 (i.e., outside of housing 910) by an optical (e.g., glass) window 908. In some implementations, this allows for faster scan rates since the mass in motion is very small—in some implementations, the optical chip 902 weights from 0.5 to 2 grams (e.g., 0.9 to 1.1 grams, or 1 gram).

FIGS. 10A-D illustrate of an example system 1000 for in-operating-theatre imaging of fresh thick tissue resected during surgery for pathology assessment. In this example, a laser fiber 1002 (e.g., single mode optical fiber) provides laser light via a laser fiber output 1004. The laser light is collimated by a collimating lens 1006 and then reflected off a dichroic beam splitter 1008 toward a beam steering mirror 1010 (e.g., at 45 degrees relative to the path of the collimated light). The beam steering mirror 1010 reflects the collimated laser beam upwards towards the optical chip 1012. The optical chip (e.g., micro lens array) focuses the collimated light into the sample, forming an array of tight foci in which fluorescence will be excited (e.g., fluorescence from the fluorescence stained sample).

Figure 10A:
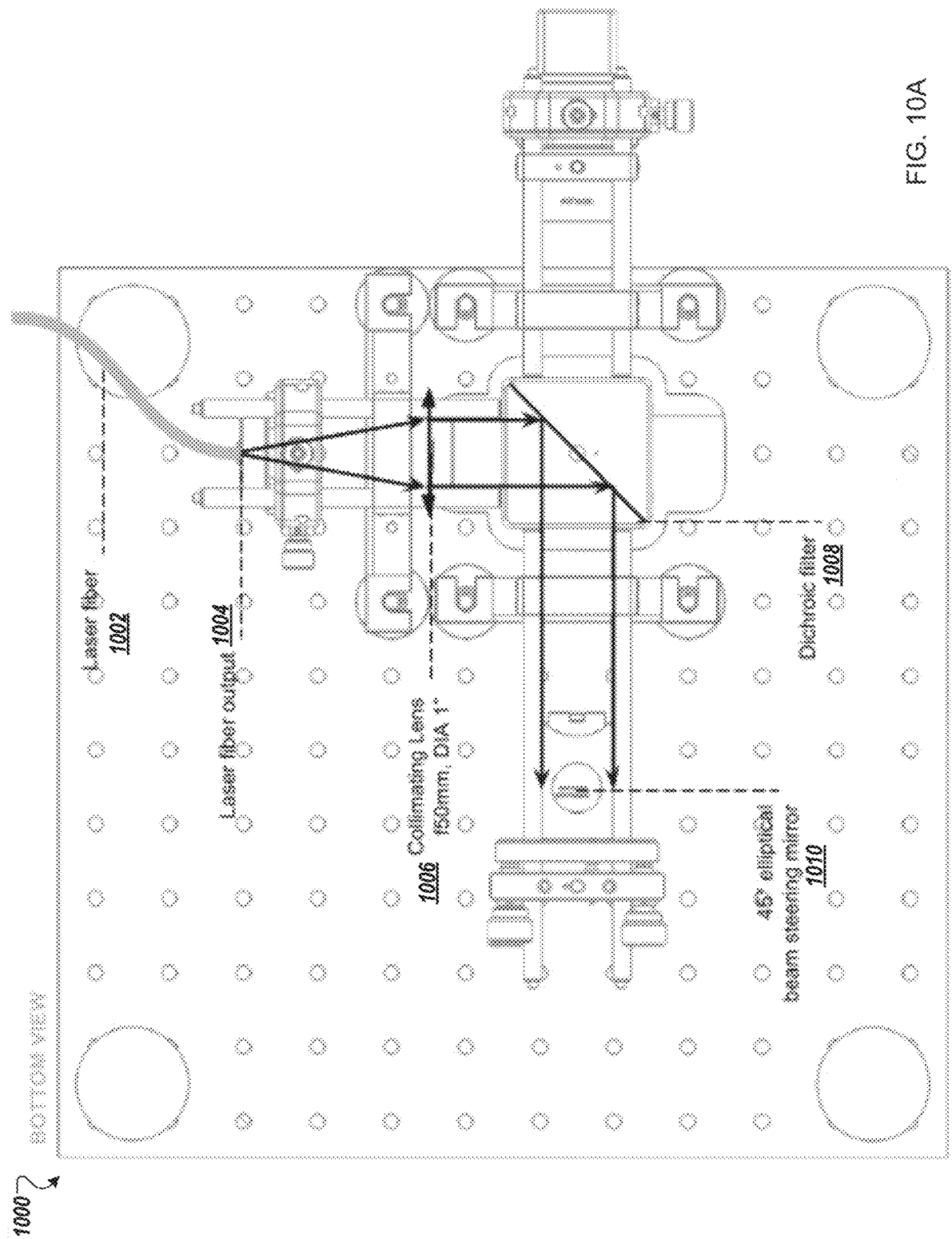
FIGS. 10A-G are illustrations of example systems for in-operating-theatre imaging of fresh thick tissue resected during surgery for pathology assessment, in accordance with embodiments of the invention.
Figure 10B:
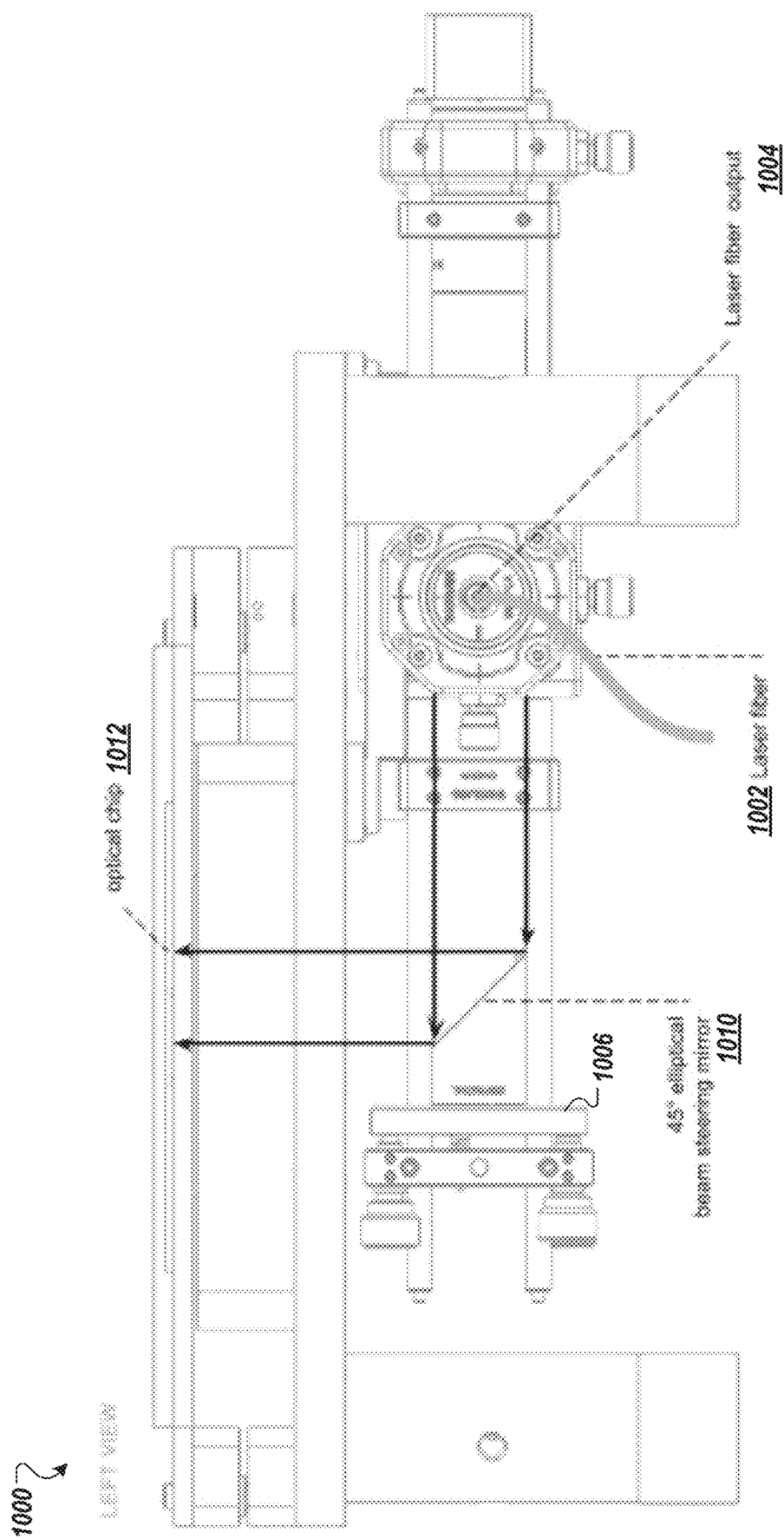
Figure 10C:
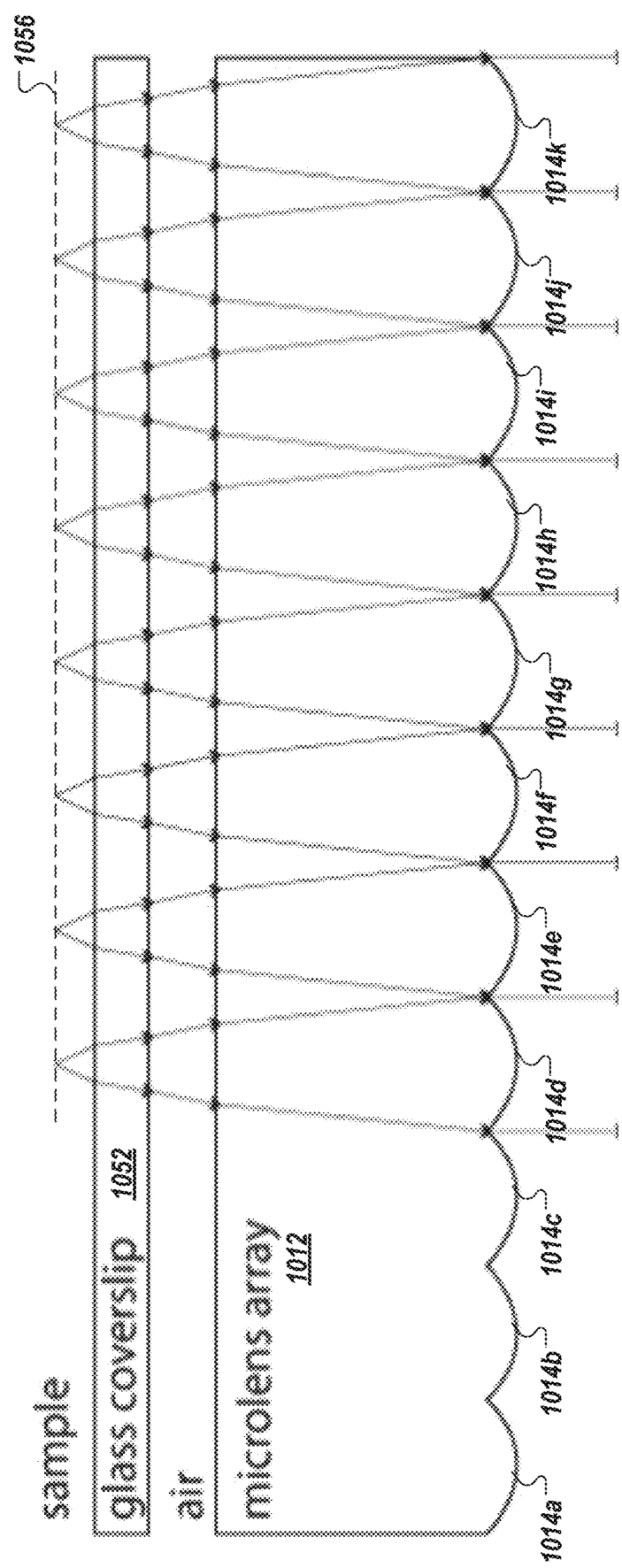
Figure 10D:
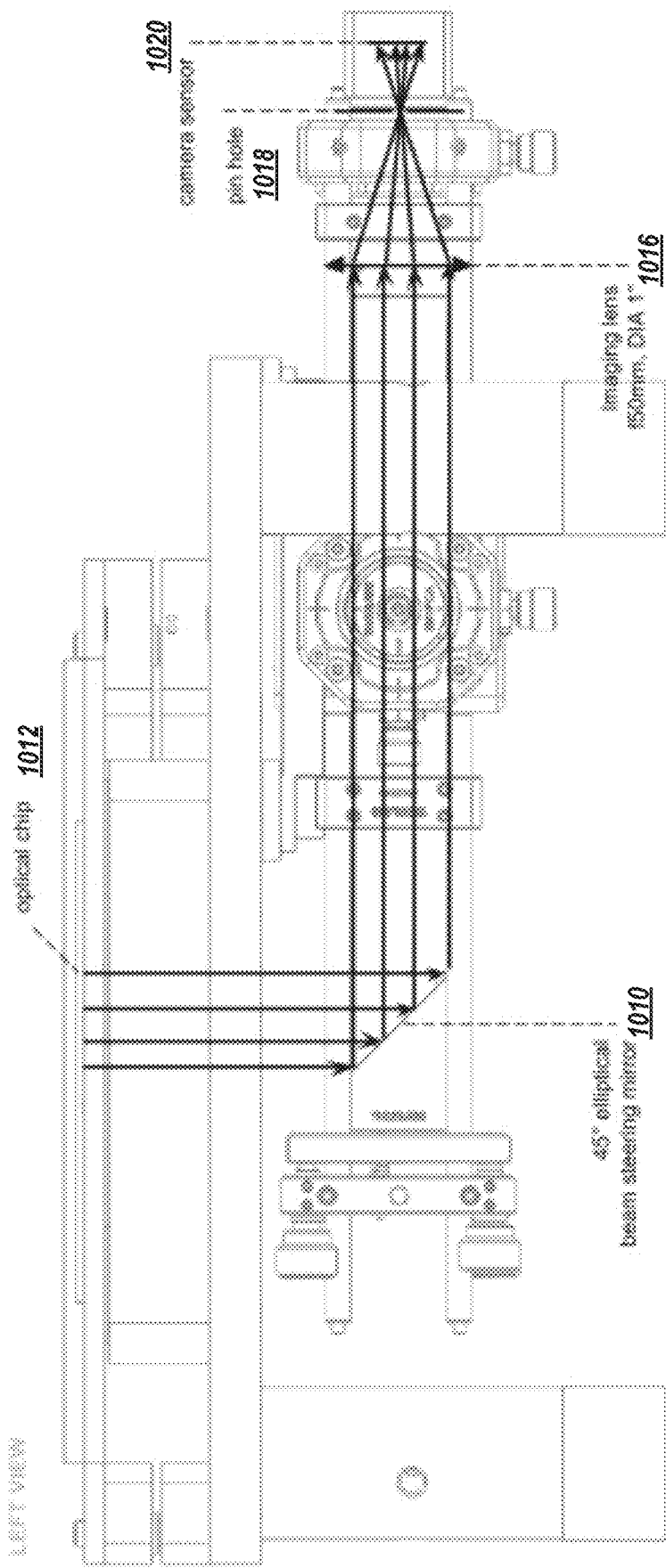

In some implementations, as illustrated in FIG. 10C, the micro lens array includes plano-convex spherical lenses that focus the collimated beam of light. The plano-convex spherical lenses, in some implementations, are used with their curved surface facing the collimated beam in order to minimize aberrations (e.g., spherical aberrations). However, in this implementation, the focal plane may not penetrate deep into the sample (e.g., only a 10-40 microns) since the focused light goes through the entire micro lens array substrate thickness, the separating medium (e.g., air), and the coverslip 1052 (e.g., glass).

Figure 10E:
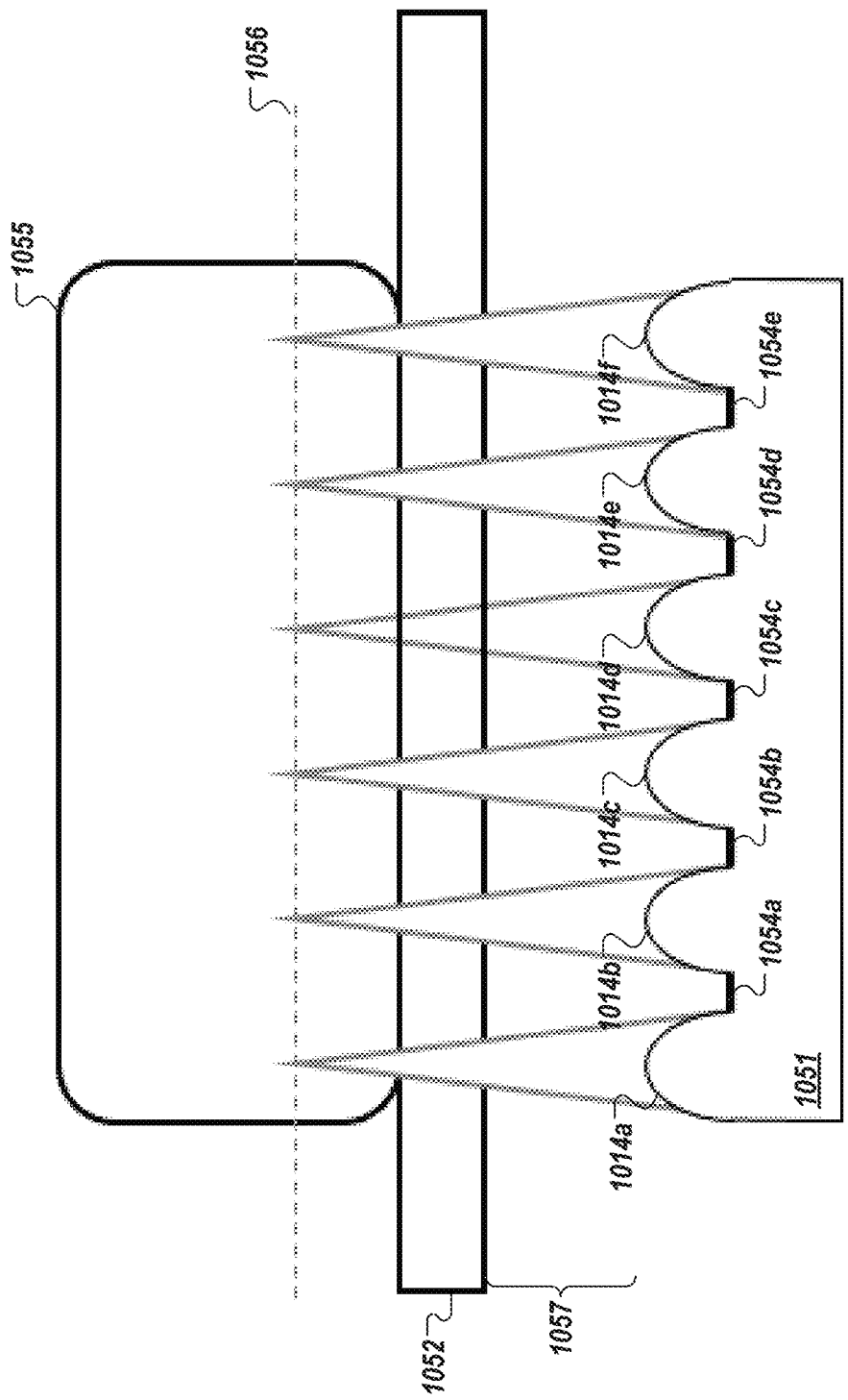

In some implementations, the plano-convex spherical lenses are used with their curved surface facing the sample as shown in FIG. 10E. This allows the focal plane 1056 to penetrate much deeper into the sample (e.g., 100-500 microns). The optical elements (e.g., micro lenses 1014*a*-1014*k*) also collect and collimate fluorescence emission from the sample. The beam steering mirror 1010 reflects the collimated fluorescence emission horizontally toward the imaging lens 1016. The imaging lens 1016 focuses the collimated fluorescence emission from each micro lens in the micro lens array 1012 through the common pinhole 1018 and forms an image of the micro lens array on the camera sensor 1020. In terms of imaging, the camera sensor 1020 and the micro lens array 1012 form a pair of conjugate planes—the micro lens array 1012 is imaged on the camera sensor 1020 by the imaging lens 1016.

Figure 10F:
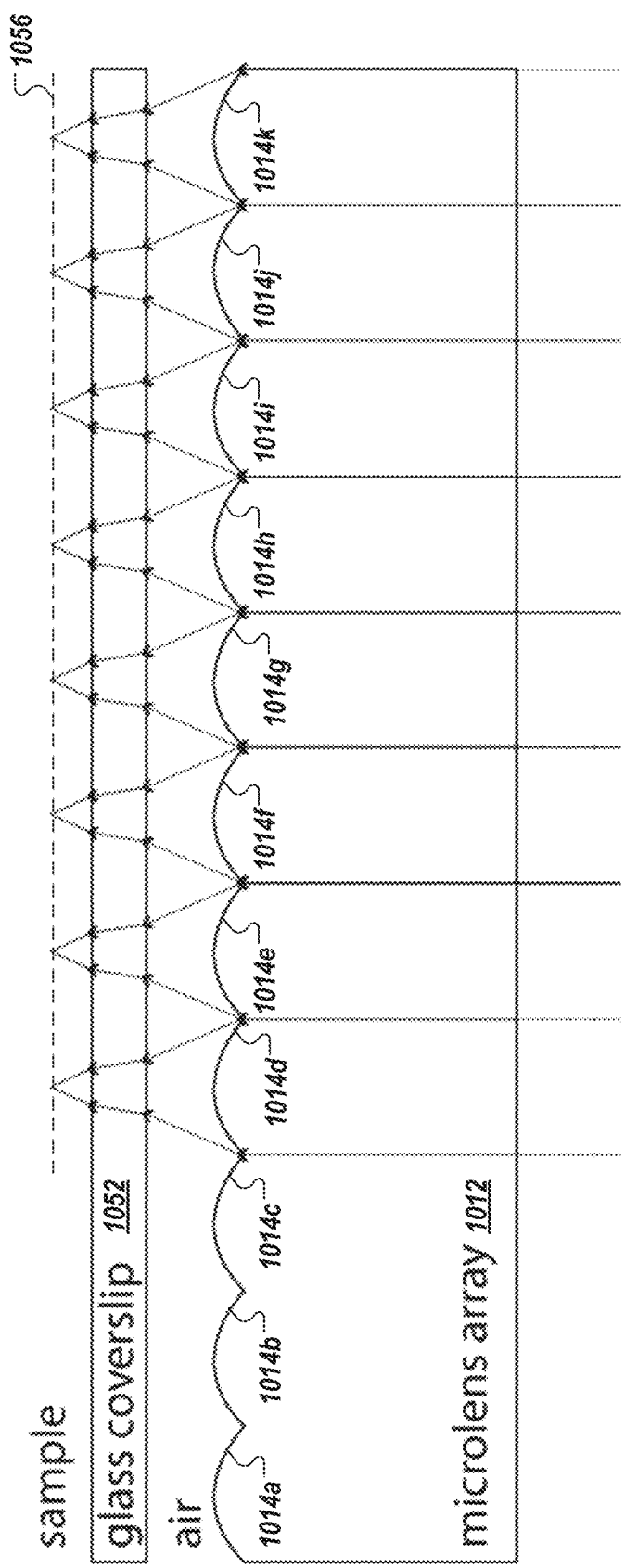
Figure 10G:
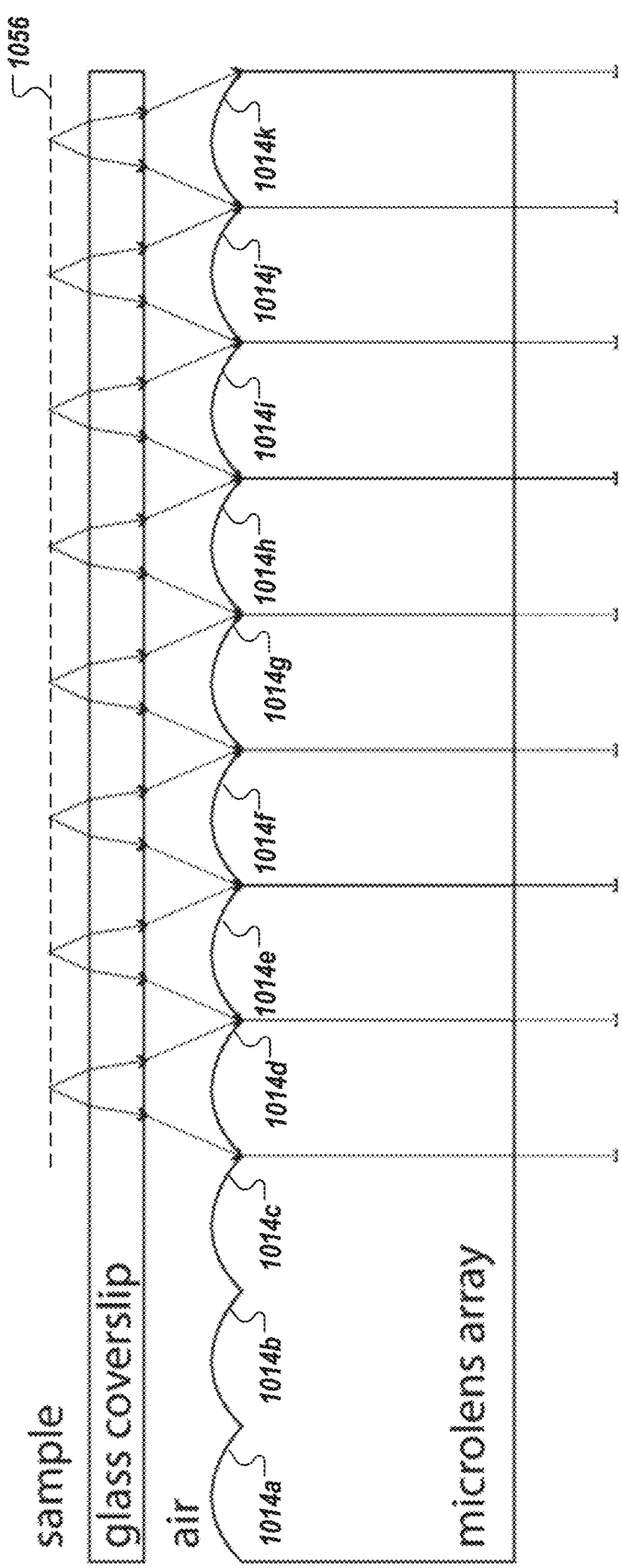

FIG. 10E illustrates an example hyperbolic shape of the micro lenses 1014. FIG. 10F illustrates an example system exciting the fluorescence in the sample with lens 1014*a-k* facing the sample. FIG. 10G illustrates the back-emitted light emitted by the excited fluorescence.

FIG. 10E illustrates an inverted configuration compared to FIG. 10C. This configuration can provide a longer working distance at a cost of poorer optical performance. This drawback can be overcome by using optical elements with non-spherical curvature, such as conical curvature. In certain embodiments, the curvature of the optical elements is conical, hyperbolic, or parabolic, rather than spherical. The curvature can be described by the factor of conic constant k.

In geometry, the conic constant k is a quantity describing conic sections. For negative k, the conic constant is given by the following equation:

$$k = -e^2,$$

where e is the eccentricity of the conic section. The equation for a conic section with apex at the origin and tangent to the y axis is:

$$y^2 - 2Rx + (k+1)x^2 = 0$$

where k is the conic constant and R is the radius of curvature at x=0. This formulation is used in geometric optics to specify oblate elliptical (k>0), spherical (k=0), prolate elliptical (0>k>−1), parabolic (k=−1), and hyperbolic (k<−1) lens and mirror surfaces. When the paraxial approximation is valid, the optical surface can be treated as a spherical surface with the same radius.

In certain embodiments, the conic constant k is a negative value with absolute value greater or equal to 0.5. A typical range fork is −10<k<−0.8. In certain embodiments, the range fork is −3<k<−0.9.

For example, an optical elements having radius of curvature of 195 um plus or minus 5 μm can be used. For example, optical elements having a radius of curvature from 190 μm to 200 μm, with a conicity k=−2.0 provides the following desired range of property values: Strehl ratio: 0.9<S<1, glass thickness for the sample interface 1052: 300 um+/−100 um; air gap 1057 between optical chip 1051 and glass interface 1052 from 150+/−50 um; and/or depth of imaging plane 1056 inside the sample 1055 of 50 um+/−50 um. Other combinations of radius of curvature and/or conicities can be chosen to produce optical elements providing properties within these desired ranges for performing the functions described herein.

The shape of the optical elements may vary. For example, in certain embodiments, each micro optical element has a conical shaped surface. In certain embodiments, each micro optical element has a hyperbolic shaped surface. In certain embodiments, the curved surface of each micro optical element has a conic constant k from −1.8 to −2.2 (e.g., −2). In certain embodiments, each micro optical element has a Strehl ratio greater than or equal to 0.8. Furthermore, in certain embodiments, each micro optical element has a spot size from 0.2 μm to 5 μm, 0.2 μm to 1 μm, 0.3 μm to 0.6 μm, 0.4 μm to 0.5 μm, greater than or equal to 0.2, and less than or equal to 5 μm. The system can have a free working distance (i.e., a distance from the tip of the micro optical elements to a focal plane of the micro optical element array) from 80 μm to 450 μm, 150 μm to 350 μm, or 250 μm to 300 μm. Additionally, the resulting focal plane of the micro optical element array can be from 10 μm to 200 μm, 20 μm to 150 μm, or 50 μm to 100 μm above the transparent window (i.e., the depth of the focal plane into a sample being imaged).

As shown in FIG. 10E, the curved surfaces of the lenses 1014 are facing the glass interface 1052 with the sample 1055 thereon. The curvature is chosen to optimize optical performance and working distance. The quality criteria for optical performance is to minimize optical aberration at the focal plane. A way of evaluating this quality is the Strehl ratio. The Strehl ration has a value between zero and one, an unaberrated optical system attaining the value of unity. Compared to FIG. 10C, the inverted configuration of FIG. 10E increases the working distance which allows the use of a thicker glass interface 1052 and improves safety in the operating room.

In certain embodiments, as shown in FIG. 10E, the areas (e.g., flat areas) in between micro-lenses 1014 are covered by an absorptive and/or reflective layer 1054. This layer 1054 can be, for example, a chromium layer, aluminum layer, or dielectric mirror layer. The purpose of this layer is to prevent or minimize the amount of illumination light transmitted by the optical chip that would travel outside of the system and possibly reach the eye of the operator. This can improve the safety of the system. The flat surface is covered because the illumination beam is collimated and therefore can travel long distance if not deviated by the curved surface. For the part of the beam focused by the curved surface, the beam is highly diverging at the distance of operator eyes which, when correctly designed, drastically diminishes the power received to a safe level.

The system disclosed herein provides several benefits. For example, alignment of the micro lens array axis with the scanning stage axis is robust. The micro lens array may be aligned by hand within approximately 5 degrees and a small rotation can be compensated for by software with a proper calibration routine for allocation of camera pixels to the optical element, offsetting, and/or rotating tiles during image reconstruction.

Misalignment between the micro lens array axis with camera axis can be compensated for by software, with a pixel allocation layer for arbitrary attribution of the camera pixels to the optical element. Similarly, alignment of the scanning stage axis with the camera axis in the embodiment in which the micro lens array is moved for scanning can be compensated for by software with a proper calibration routine and subsequent allocation of camera pixels to optical element.

Lateral alignment of confocal pinhole with the imaging lens must be precise. The pinhole will be relatively small (e.g., 75-400 μm) and must be precisely aligned in the imaging lens focal plane. This may be accomplished, for example, using an XY micrometer. The axial alignment of the confocal pinhole with the imaging lens is also important. For relatively long focal length of the imaging lens (e.g., f>50 mm), alignment in Z direction is not as critical and can be accomplished within 1 mm or better without precise positioning system.

The axial positioning of the imaging lens from the micro lens array plane determines the magnification of the imaging system. In some implementations, this does not need to be precisely adjusted.

The axial positioning of the imaging lens from the camera sensor plane determines how well focused the image of the micro lens array is on the camera sensor. In some implementations, considering the effective resolution of the imaging system through the confocal pinhole, manual adjustment of the lens position (e.g., to within 1 mm) on the cage system is sufficient for the long focal length of the imaging lens (e.g., f>50 mm). Further, for a long focal length imaging lens (e.g., f>50 mm), the axial positioning of pinhole from camera sensor plane, in some implementations, must be within less than or equal to a millimeter. For long focal length of the collimating lens (e.g., f>50 mm), which are needed to generate large beam diameter to illuminate the full micro lens array, manual adjustment of the axial positioning of the fiber collimation lens (e.g., to 1 mm) on the cage system is sufficient.

For a collimation of fibered light source, the lateral position of the fiber collimation lens is critical. A XY micrometer, for example, may be used to center optical fiber on collimating lens optical axis.

In scanning microscopy, the resolution of the image may depend on the position of the reader while scanning the sample. In some implementations, the image is reconstructed based on the relation between the position of the reader relative to the sample and the corresponding signal measured by the detector. Image quality may be deteriorated by imprecise position measurement. In some implementations, positioning feedback is accomplished using a closed loop positioning system to compensate for non-linearity, hysteresis and drift issues.

In some implementations, focusing elements may be used for positioning feedback. For example, one or more micro lenses can be used to record the image of a local known pattern, thereby providing a two or three-dimensional position feedback. In some implementations, the achromatic property of the lens allows for using a different wavelength for the feedback than the one used to image the sample. This allows image information to be easily separated from the positioning information with a dichroic beam splitter.

As described above in relation to FIG. 4 and FIG. 5, the disclosed technology, in certain embodiments, includes a sample holder. In some embodiments, the disclosed technology also includes a kinematic support. In certain embodiments, the specimen imaging interface designates the part of the assembly on which the specimen is imaged.

FIGS. 11A through 11G illustrate an example implementation of a specimen imaging area in accordance with an embodiment of the disclosed technology. In this example, the design is optimized to take into account requirements for use in hospital and ergonomic integration in the operating room workflow. The system is designed to be robust to fluid leakage. In particular, it includes a containment ring sealed on the glass window to prevent liquid related to the sample from being in contact with the rest of the device (e.g., for safety—hygiene). Additionally, the design minimizes the risk of liquid flowing inside the device during the cleaning of the device (efficacy).

FIGS. 11A and 11B illustrate an example specimen imaging interface on the microscopy instrument. FIG. 11A illustrates the specimen imaging interface 1100 connected to the rest of the imaging system 1190 whereas FIG. 11B illustrates the specimen imaging interface 1100 alone. The optical interface 1102 is the surface on which the specimen lies. It protects the optical chip 1104 and the rest of the instrument from the environment (dust, liquids, etc. including the specimen itself). It is compatible with the imaging process (transparency, planarity, etc.).

The optical interface mount 1106 is the mechanical support for the optical interface 1102. The optical interface clamp 1108 is the ring-shaped part (although other shapes can be used) that maintains the optical interface 1102 (e.g., transparent window) in place against the optical interface mount 1106. The optical interface clamp 1108 seals the device with O-ring gaskets (not shown). In certain embodiments, the optical interface clamp 1108 is designed to be in contact with the specimen while preventing the optical interface mount 1106 from contacting the specimen during use.

Figure 11E:
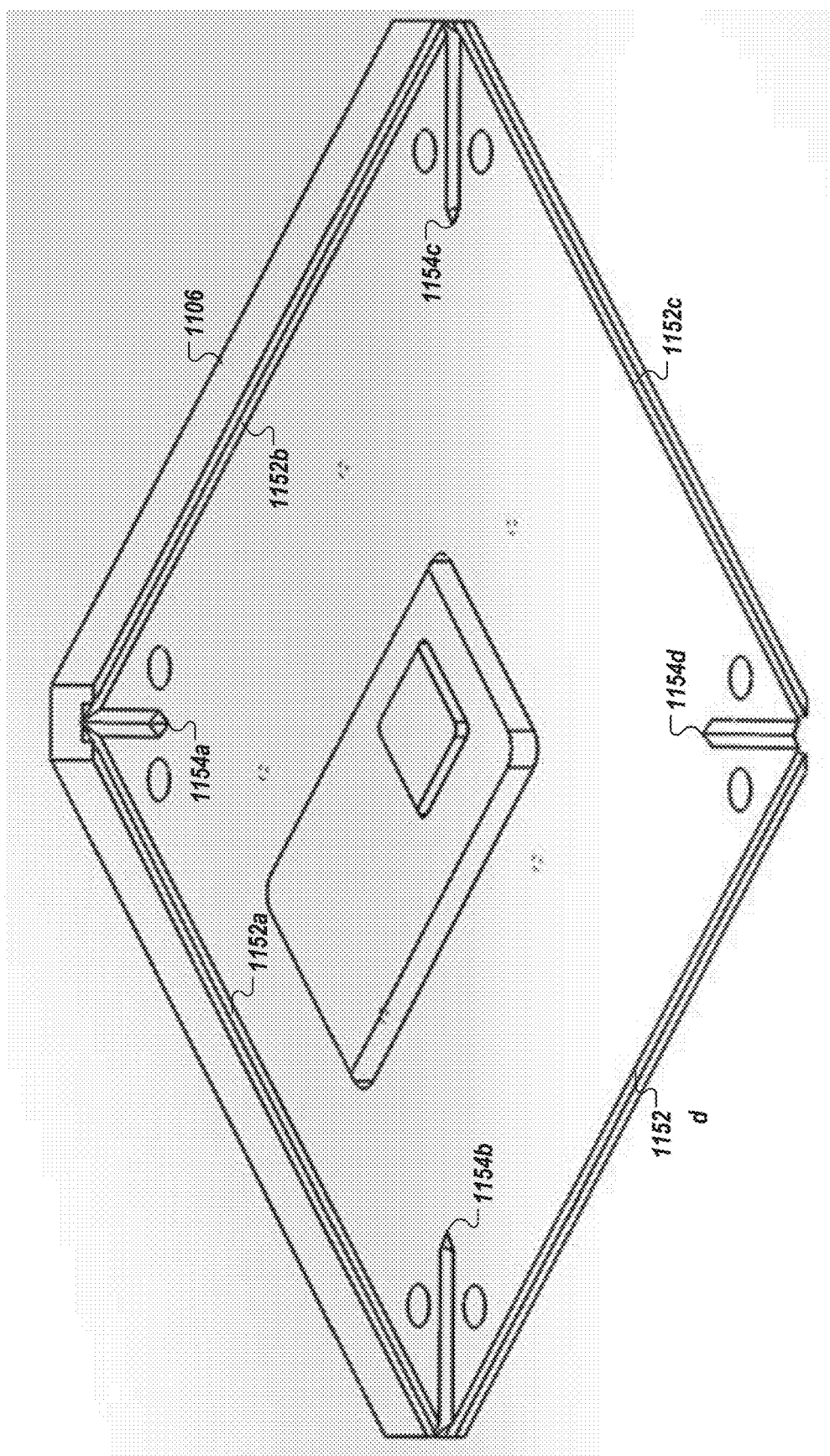

The kinematic blocks 1112 serve to mount the precision adjusters 1114 which form the basis of the kinematic system. In certain embodiments, the kinematic system is a three-point kinematic system that uses only three adjusters for kinematic positioning of the optical interface mount 1106. In other embodiments, the kinematic system is a four-point kinematic system that uses four adjusters. Other variations are possible as well. Additionally, the kinematic blocks 1112 serve to mount the protective plates that delimit the perimeter of the specimen imaging interface, and protect sensitive components located under the optical interface mount 1106 from the outside environment. The top of the adjusters 1114 on each kinematic block 1112 contact at least a portion of a respective groove 1154a-d (collectively 1154) on the bottom side of the optical interface mount 1106 such that the grooves 1154 on the bottom side of the optical interface mount 1106 each sit on a respective kinematic block 1112 as shown in FIGS. 11E and 11F.

The base plate/frame refers to the mechanical backbone of the instrument on which all the components and modules are fixed. The baseplate is not part of the specimen imaging interface.

As illustrated in FIG. 11C, the entire optical interface mount assembly (with optical interface 1102, optical interface clamp 1108, etc.) can be magnetically maintained in position on the kinematic system and can be removed easily. Removing the optical interface mount 1106 exposes sensitive components (notably the optical chip 1104 and the scanning stage) to the "outside" environment (dust, liquid spill, mechanical impact, etc.) and allows removal of the optical interface 1102 itself. In this example, as shown in FIG. 11C, the optical interface clamp 1108 is fastened by five screws and can thus be removed relatively easily to allow replacement of the optical interface 1102 or the O-ring seals. Other attachment systems or numbers of screws can be used to fasten the optical interface clamp 1108 to the system.

The optical interface mount 1106 sits on the precision adjusters 1114 (e.g., three precision adjusters 1114) of the kinematic system. The position of the optical interface mount 1106 can be maintained by magnets. The optical interface mount 1106 can thus be easily removed from the microscopy instrument. In the example shown in FIG. 11A through 11C, the optical interface mount 1106 is machined from a 200 mm×200 mm×8 mm aluminum plate and has a anodized finish.

In certain embodiments, the optical interface clamp 1108 has two hidden grooves that accommodate O-rings to seal off the device by (i) preventing liquids inside the ring 1108 from flowing into the device, and (ii) preventing liquid spilled outside the ring 1108 from flowing into the device. FIG. 11D illustrates two examples of optical interface clamps 1108. In both of these examples, the optical interface clamp 1108 is fastened to the optical interface mount 1106 by hardware 1010, such as countersunk flat head screws. In this example, the optical interface clamp 1108 and optical interface 1102 can be disposable or sterilizable. The optical interface clamp 1108 can secure the optical interface 1102 onto the system and seal against the optical interface 1102 and/or optical interface mount 1106 to prevent liquid leakage from the sample into the system.

FIGS. 11E through 11G illustrate an example of a spill-proof optical interface mount 1106. Specifically, FIG. 11E is a top view of the optical interface mount 1106 showing the groove 1152a-d (collectively groove 1152) in the bottom of the optical interface mount 1106. FIG. 11F is a bottom view of the example spill-proof optical interface mount 1106 and FIG. 11G is a cross-sectional view of the example spill-proof optical interface mount 1106 along section A-A as shown in FIG. 11F. It is important, in certain embodiments, to prevent liquid spilled on the optical interface mount 1106 from flowing into the device. In this example, the bottom surface of the optical interface mount 1106 near the perimeter of the optical interface mount 1006 is has a groove 1152 (e.g., a groove with a rectangular, circular, oval, triangular, or square cross-section) that prevents droplets on the bottom surface from migrating inwards). If liquid drains off the edge of the top surface of the interface mount 1106, it will fall down when it reaches the groove 1152. This prevents or reduces the likelihood that the liquid enters the system under the optical interface mount 1106.

Figure 12A:
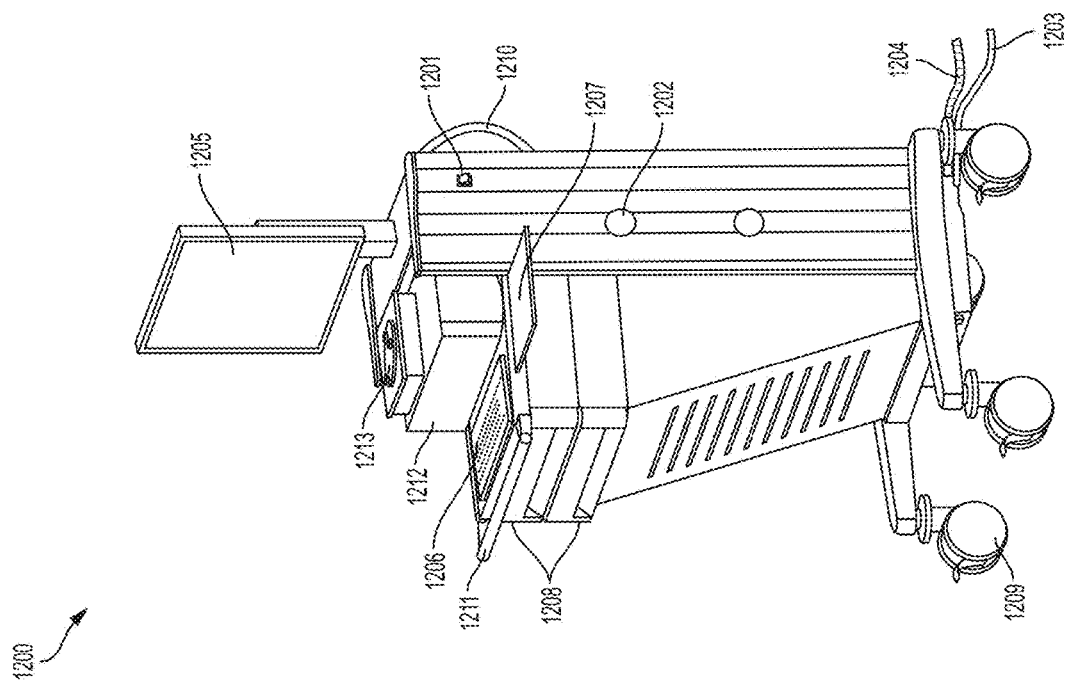
FIG. 12A is an illustration of an example mobile cart in accordance with an embodiment of the invention.
Figure 12B:
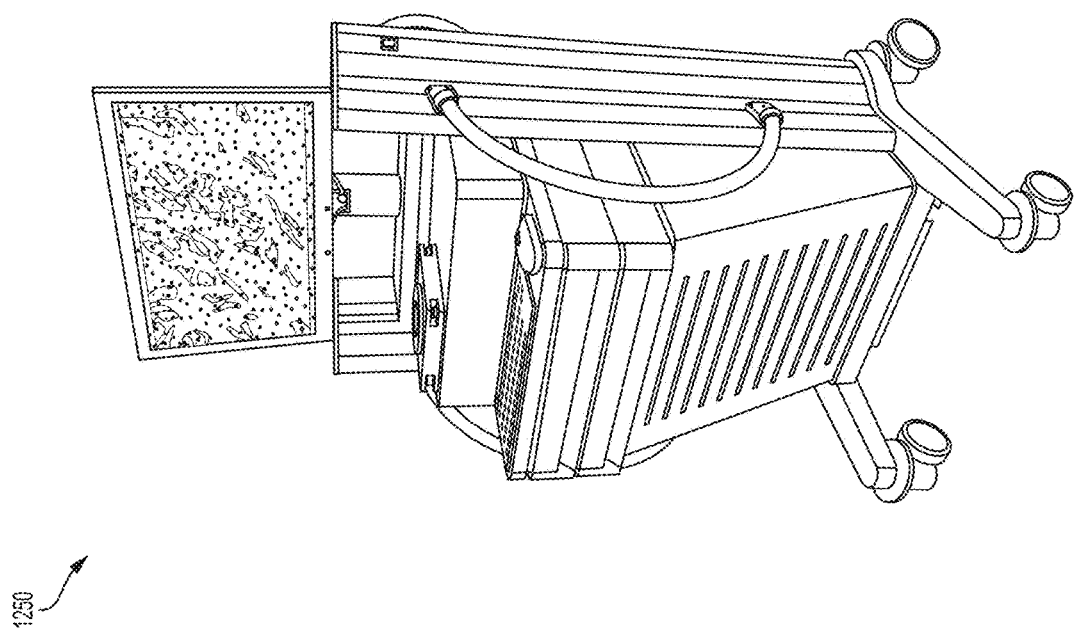
FIG. 12B is an illustration of an example mobile cart in accordance with an embodiment of the invention.

FIG. 12A is an illustration of an example mobile cart with an imaging device thereon for providing in-operating-theatre imaging of fresh thick tissue resected during surgery for pathology assessment and FIG. 12B is an illustration of an example of such a mobile cart.

As shown in FIG. 12A, an example mobile cart 1200 may include a plurality (e.g., three or four) wheels 1209 on which the cart can be rolled. Other transportation systems may be used as well, such as tracks. The cart 1200 can be motorized or can be pulled/pushed by a user. The mobile cart includes a microscopy instrument 1210, such as the instrument described herein, with a specimen imaging interface 1212. In certain embodiments, the mobile cart 1200 includes a display monitor 1205, a keyboard, 1206, and a user interaction device 1207 (e.g., touch pad, touch screen on the display monitor 1205, and/or computer mouse). The microscopy instrument 1210 can be connected to the display monitor 1205 such that scans/images of the specimen in the imaging area 1213 can be shown on the display monitor 1206.

In certain embodiments, the cart includes handles, such as a front side handle 1211 and backside handles 1210. The mobile cart 1200 can be equipped with a power switch 1201 (e.g., on/off switch) that is used to control power to equipment on the mobile cart 1200. A power cable 1203 can be used to connect the mobile cart 1200 to a power source. In certain embodiments, the cart 1200 has a battery for self-sufficient use. The mobile cart 1200 can also include an equipotential bonding cable 1204. The mobile cart 1200 can include one or more drawers 1208 (e.g., two drawers as shown in FIG. 12A). The mobile cart 1200 can also include a cable winder 1202 around which one or more cables can be wound for storage during, before, or after use.

Experiments

Several experiments were performed to identify sufficient optical chip designs. In these experiments, optical chip designs were tested using different curvature lenses and different lens orientations. Specifically, the lens orientation varied from facing the illumination beam and facing the sample. The shape of the lenses varied from spherical to conical. Table 1 summarizes the test results by showing the main quality criteria evaluated along with the tested optical chip configurations and curvature shapes.

TABLE 1

| | Optical Chip Design | | |
|---|---|---|---|
| | 1 | 2 | 3 |
| Configuration | A | | B |
| Curvature shape | Spherical | | Conical (k = −2.0) |
| Performance criteria | | | |
| fWD (um) | 110 | 420 | 400 |
| Spot size RMS radius (um) | 2.1 | 11.6 | 0.34 |
| Performance for microscopy | Lower performance; lower specification | Poor Performance; out of specification | High Performance; best specification |
| Strehl ratio level of aberration | <0.8 aberrated optics | <0.8 aberrated optics | 0.91 diffraction limited |

In these experiments, three optical chips designs were tested. The optical chip design of configuration A utilized lenses having a curvature facing the illumination beam. In contrast, the optical chip designs of configuration B utilized lenses having a curvature facing the sample. Optical chip designs 1 and 2 utilized spherical lenses as described above while chip design 3 utilized conical lenses as described above. The optimization aims to maximize the free working distance (fWD) while minimizing the spot radius and maintaining high performance microscopy. The spot radius is representative of the smallest detail that can be distinguished by the optical system, hence it relates to resolution. Thus, optimization aims at minimizing the spot radius value. The Strehl ratio is a way of quantifying the level of aberration. Being diffraction limited means that the system reaches the physical limits and can therefore be considered as a non-aberrated optical system.

Figure 13:
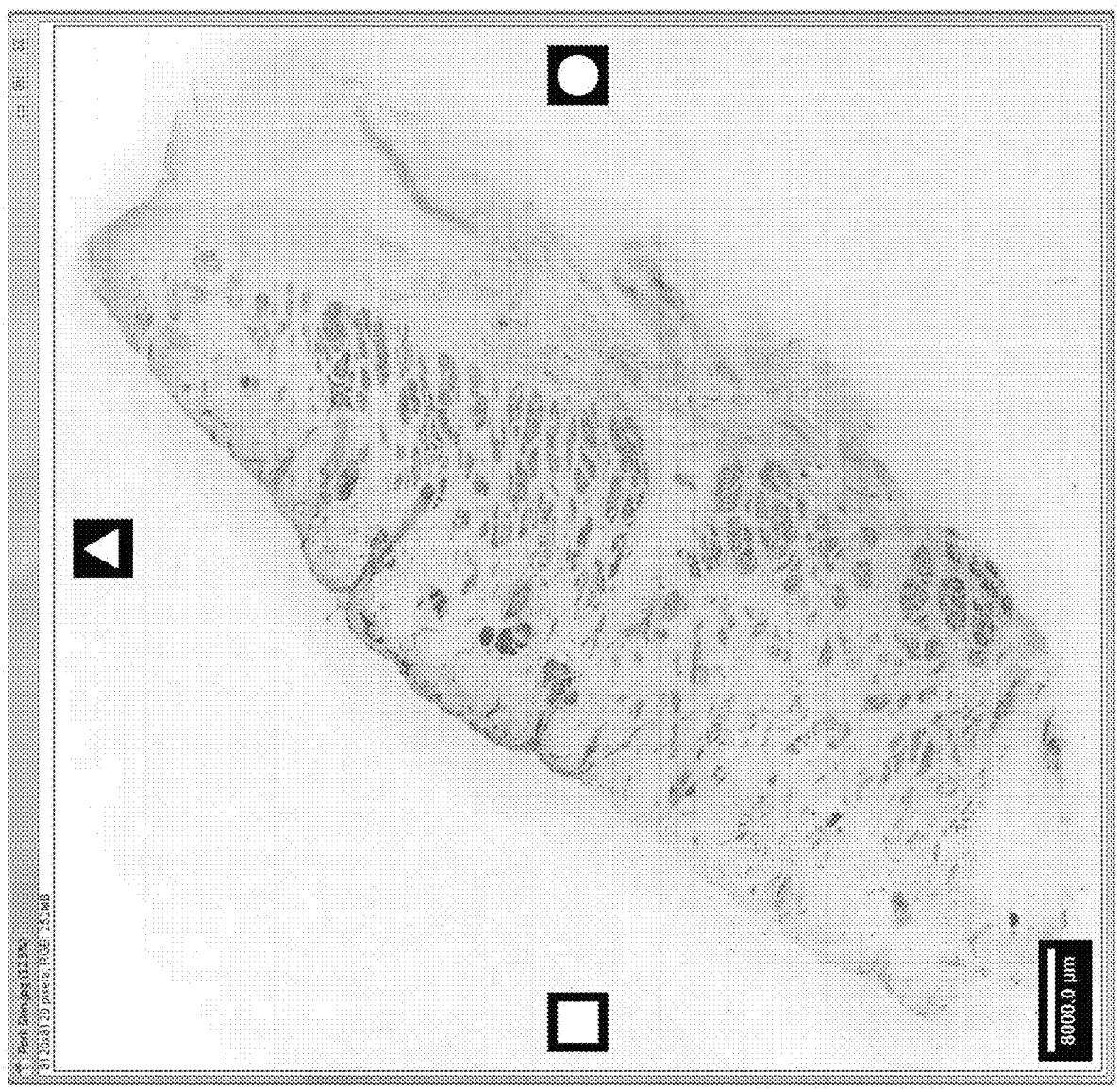
FIG. 13 is a screenshot of a microscopy image acquired on fresh tissue using the disclosed technology.
Figure 13:
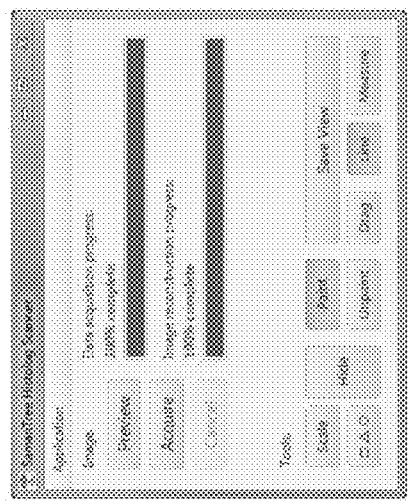

FIG. 13 is a screenshot of a microscopy image of fresh tissue acquired using the disclosed technology, specifically using optical chip design 3 from Table 1. The screenshot shows the Graphical User Interface (GUI), the alignment marks (e.g. square, triangle and round) to recognize tissue orientation, and the image obtained with a fresh porcine eyelid tissue deposited on the scanner instrument. The disclosed technology was used to capture an image that represents a digital slice of the fresh tissue—thus, allowing an image of a cross section of the tissue to be taken without actually slicing the tissue.

Figure 14:
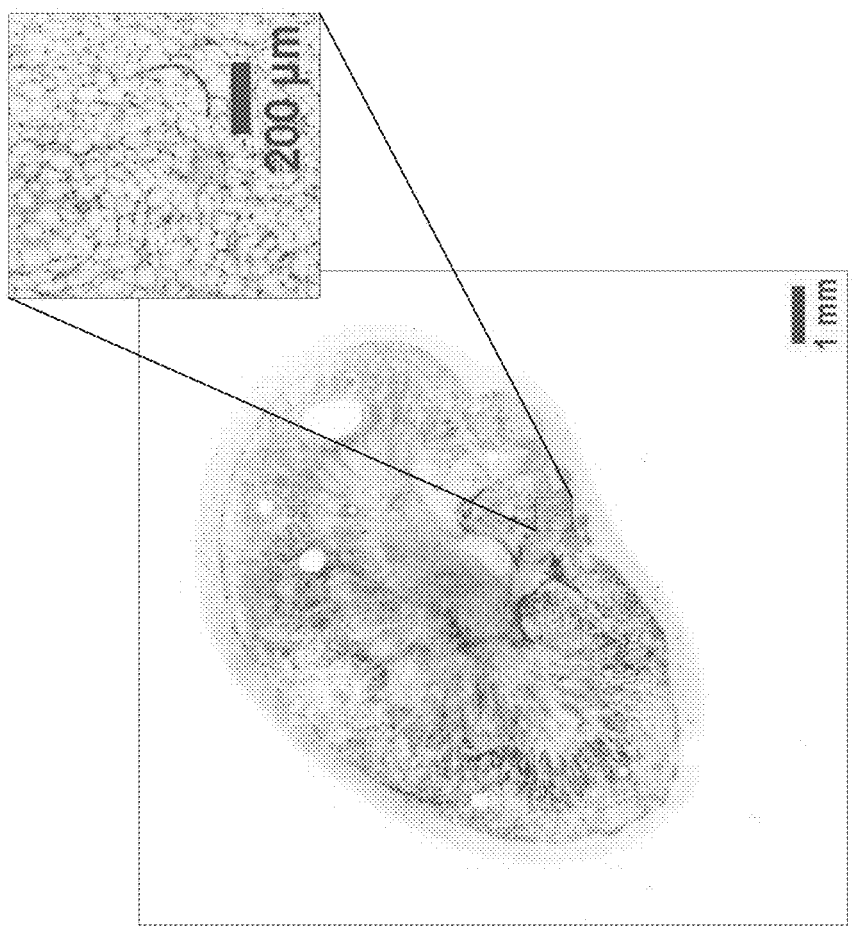
FIG. 14 is an image acquired on fresh mice kidney tissue using the disclosed technology.

FIG. 14 is an image acquired on fresh mice kidney tissue (i.e., the piece of tissue has been deposited on the instrument). The insert in the image shows a zoomed adipose tissue region and illustrates that the whole image is not showed at full resolution and can be zoomed to reveal further details with appropriate software display tool. Again, the disclosed technology was used to capture an image that represents a digital slice of the fresh tissue—thus, allowing an image of a cross section of the tissue to be taken without actually slicing the tissue.

Figure 15:
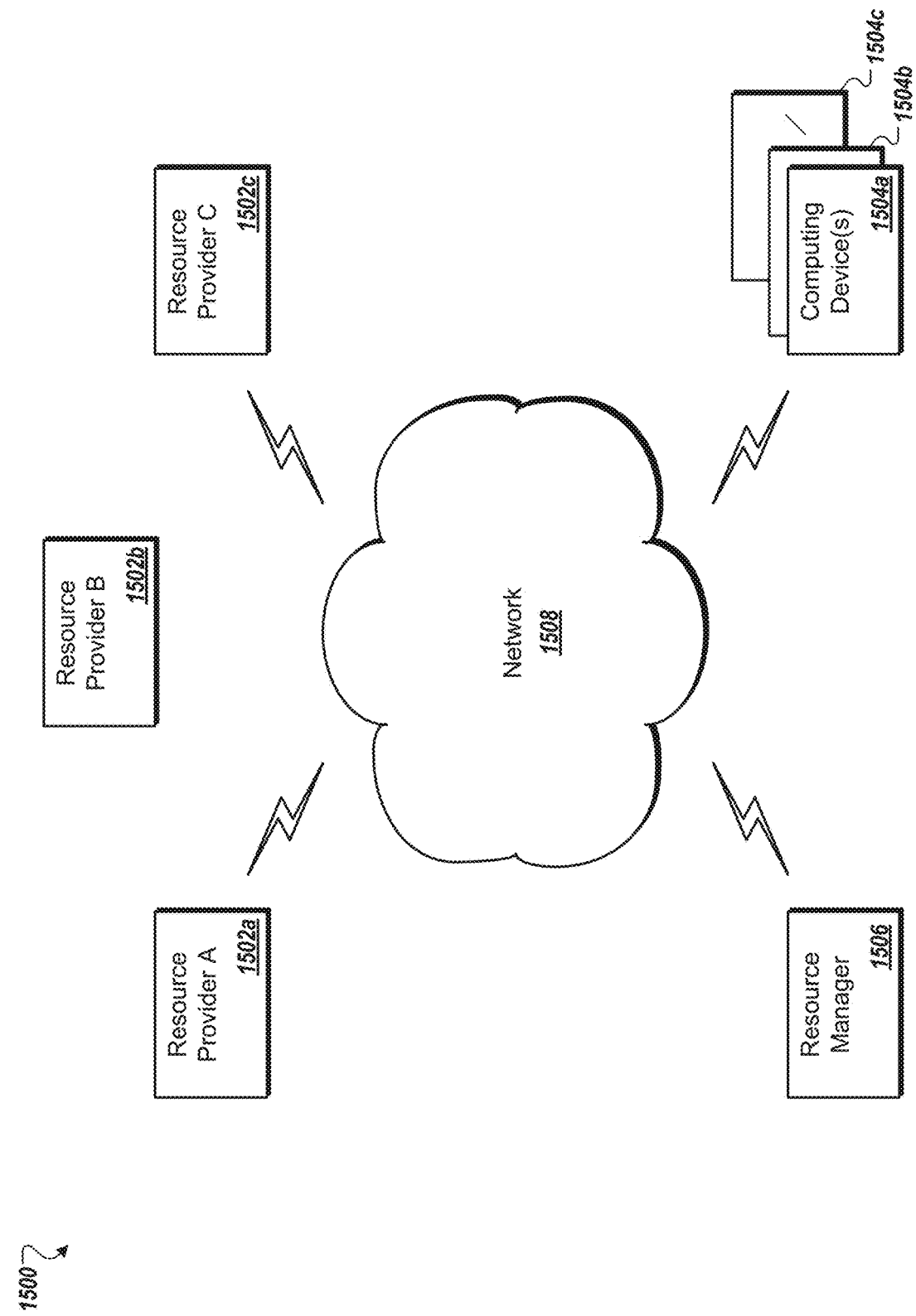
FIG. 15 shows a block diagram of an exemplary cloud computing environment.

As shown in FIG. 15, an implementation of a network environment 1500 for use providing in-operating-theatre imaging of fresh thick tissue resected during surgery for pathology assessment is shown and described. In brief overview, referring now to FIG. 15, a block diagram of an exemplary cloud computing environment 1500 is shown and described. The cloud computing environment 1500 may include one or more resource providers 1502a, 1502b, 1502c (collectively, 1502). Each resource provider 1502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1502 may be connected to any other resource provider 1502 in the cloud computing environment 1500. In some implementations, the resource providers 1502 may be connected over a computer network 1508. Each resource provider 1502 may be connected to one or more computing device 1504a, 1504b, 1504c (collectively, 1504), over the computer network 1508.

The cloud computing environment 1500 may include a resource manager 1506. The resource manager 1506 may be connected to the resource providers 1502 and the computing devices 1504 over the computer network 1508. In some implementations, the resource manager 1506 may facilitate the provision of computing resources by one or more resource providers 1502 to one or more computing devices 1504. The resource manager 1506 may receive a request for a computing resource from a particular computing device 1504. The resource manager 1506 may identify one or more resource providers 1502 capable of providing the computing resource requested by the computing device 1504. The resource manager 1506 may select a resource provider 1502 to provide the computing resource. The resource manager 1506 may facilitate a connection between the resource provider 1502 and a particular computing device 1504. In some implementations, the resource manager 1506 may establish a connection between a particular resource provider 1502 and a particular computing device 1504. In some implementations, the resource manager 1506 may redirect a particular computing device 1104 to a particular resource provider 1102 with the requested computing resource.

Figure 16:
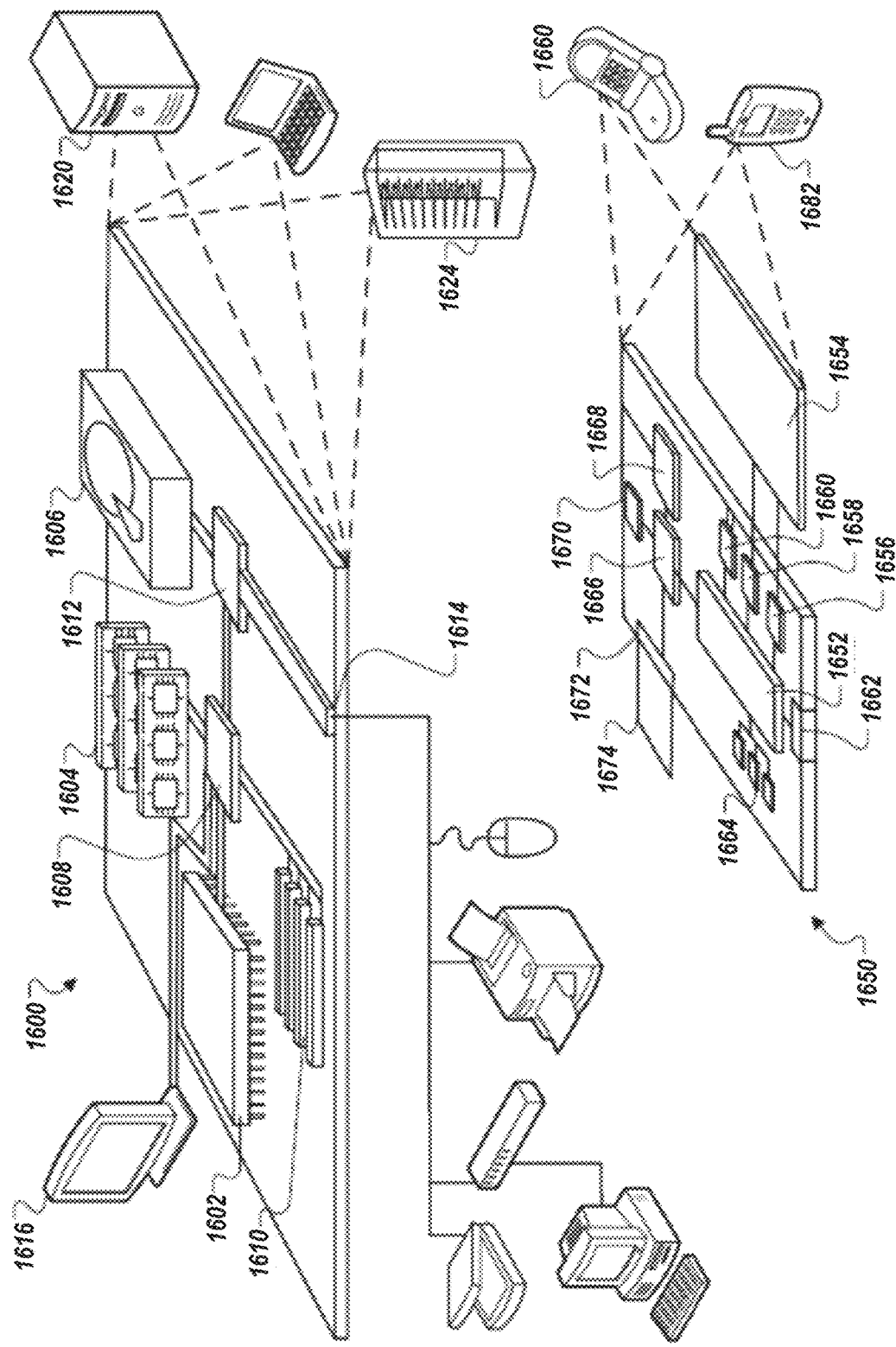
FIG. 16 is a block diagram of a computing device and a mobile computing device.

FIG. 16 shows an example of a computing device 1600 and a mobile computing device 1650 that can be used to implement the techniques described in this disclosure. The computing device 1600 is intended to represent various forms of digital computers, such as laptops, desktops, workstations, personal digital assistants, servers, blade servers, mainframes, and other appropriate computers. The mobile computing device 1650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1600 includes a processor 1602, a memory 1604, a storage device 1606, a high-speed interface 1608 connecting to the memory 1604 and multiple high-speed expansion ports 1610, and a low-speed interface 1612 connecting to a low-speed expansion port 1614 and the storage device 1606. Each of the processor 1602, the memory 1604, the storage device 1606, the high-speed interface 1608, the high-speed expansion ports 1610, and the low-speed interface 1612, are interconnected using various busses, and may be mounted on a common motherboard or in other manners as appropriate. The processor 1602 can process instructions for execution within the computing device 1600, including instructions stored in the memory 1604 or on the storage device 1606 to display graphical information for a GUI on an external input/output device, such as a display 1616 coupled to the high-speed interface 1608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1604 stores information within the computing device 1600. In some implementations, the memory 1604 is a volatile memory unit or units. In some implementations, the memory 1604 is a non-volatile memory unit or units. The memory 1604 may also be another form of computer-readable medium, such as a magnetic or optical disk.

The storage device 1606 is capable of providing mass storage for the computing device 1600. In some implementations, the storage device 1606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1602), perform one or more methods, such as those described above. The instructions can also be stored by one or more storage devices such as computer- or machine-readable mediums (for example, the memory 1604, the storage device 1606, or memory on the processor 1602).

The high-speed interface 1608 manages bandwidth-intensive operations for the computing device 1600, while the low-speed interface 1612 manages lower bandwidth-intensive operations. Such allocation of functions is an example only. In some implementations, the high-speed interface 1608 is coupled to the memory 1604, the display 1616 (e.g., through a graphics processor or accelerator), and to the high-speed expansion ports 1610, which may accept various expansion cards (not shown). In the implementation, the low-speed interface 1612 is coupled to the storage device 1606 and the low-speed expansion port 1614. The low-speed expansion port 1614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1600 may be implemented in a number of different forms, as shown in the figure. For example, it may be implemented as a standard server 1620, or multiple times in a group of such servers. In addition, it may be implemented in a personal computer such as a laptop computer 1622. It may also be implemented as part of a rack server system 1624. Alternatively, components from the computing device 1600 may be combined with other components in a mobile device (not shown), such as a mobile computing device 1650. Each of such devices may contain one or more of the computing device 1600 and the mobile computing device 1650, and an entire system may be made up of multiple computing devices communicating with each other.

The mobile computing device 1650 includes a processor 1652, a memory 1664, an input/output device such as a display 1654, a communication interface 1666, and a transceiver 1668, among other components. The mobile computing device 1650 may also be provided with a storage device, such as a micro-drive or other device, to provide additional storage. Each of the processor 1652, the memory 1664, the display 1654, the communication interface 1666, and the transceiver 1668, are interconnected using various buses, and several of the components may be mounted on a common motherboard or in other manners as appropriate.

The processor 1652 can execute instructions within the mobile computing device 1650, including instructions stored in the memory 1664. The processor 1652 may be implemented as a chipset of chips that include separate and multiple analog and digital processors. The processor 1652 may provide, for example, for coordination of the other components of the mobile computing device 1650, such as control of user interfaces, applications run by the mobile computing device 1650, and wireless communication by the mobile computing device 1650.

The processor 1652 may communicate with a user through a control interface 1658 and a display interface 1656 coupled to the display 1654. The display 1654 may be, for example, a TFT (Thin-Film-Transistor Liquid Crystal Display) display or an OLED (Organic Light Emitting Diode) display, or other appropriate display technology. The display interface 1656 may comprise appropriate circuitry for driving the display 1654 to present graphical and other information to a user. The control interface 1658 may receive commands from a user and convert them for submission to the processor 1652. In addition, an external interface 1662 may provide communication with the processor 1652, so as to enable near area communication of the mobile computing device 1650 with other devices. The external interface 1662 may provide, for example, for wired communication in some implementations, or for wireless communication in other implementations, and multiple interfaces may also be used.

The memory 1664 stores information within the mobile computing device 1650. The memory 1664 can be implemented as one or more of a computer-readable medium or media, a volatile memory unit or units, or a non-volatile memory unit or units. An expansion memory 1674 may also be provided and connected to the mobile computing device 1650 through an expansion interface 1672, which may include, for example, a SIMM (Single In Line Memory Module) card interface. The expansion memory 1674 may provide extra storage space for the mobile computing device 1650, or may also store applications or other information for the mobile computing device 1650. Specifically, the expansion memory 1674 may include instructions to carry out or supplement the processes described above, and may include secure information also. Thus, for example, the expansion memory 1674 may be provide as a security module for the mobile computing device 1650, and may be programmed with instructions that permit secure use of the mobile computing device 1650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1652), perform one or more methods, such as those described above. The instructions can also be stored by one or more storage devices, such as one or more computer- or machine-readable mediums (for example, the memory 1664, the expansion memory 1674, or memory on the processor 1652). In some implementations, the instructions can be received in a propagated signal, for example, over the transceiver 1668 or the external interface 1662.

The mobile computing device 1650 may communicate wirelessly through the communication interface 1666, which may include digital signal processing circuitry where necessary. The communication interface 1666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1668 using a radio-frequency. In addition, short-range communication may occur, such as using a Bluetooth®, Wi-Fi™, or other such transceiver (not shown). In addition, a GPS (Global Positioning System) receiver module 1670 may provide additional navigation- and location-related wireless data to the mobile computing device 1650, which may be used as appropriate by applications running on the mobile computing device 1650.

The mobile computing device 1650 may also communicate audibly using an audio codec 1660, which may receive spoken information from a user and convert it to usable digital information. The audio codec 1660 may likewise generate audible sound for a user, such as through a speaker, e.g., in a handset of the mobile computing device 1650. Such sound may include sound from voice telephone calls, may include recorded sound (e.g., voice messages, music files, etc.) and may also include sound generated by applications operating on the mobile computing device 1650.

The mobile computing device 1650 may be implemented in a number of different forms, as shown in the figure. For example, it may be implemented as a cellular telephone 1680. It may also be implemented as part of a smart-phone 1682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Components described herein may be made of polymer, metal, metalloid, glass, ceramic, or other materials, or composites thereof. In certain embodiments, components are made of surgical grade materials. Components may be sterilizable, autoclaveable, reusable, and/or disposable. Disposable components may be designed for single use or limited multi-use (e.g., between 2 and 10 uses).

In view of the structure, functions and apparatus of the systems and methods described here, in some implementations, a system and method for providing in-operating-theatre imaging of fresh thick tissue resected during surgery for pathology assessment are provided. Having described certain implementations of methods and apparatus for supporting in-operating-theatre imaging of fresh thick tissue resected during surgery for pathology assessment, it will now become apparent to one of skill in the art that other implementations incorporating the concepts of the disclosure may be used. Therefore, the disclosure should not be limited to certain implementations, but rather should be limited only by the spirit and scope of the following claims.

Having described certain implementations of methods and apparatus for supporting transfer printing capacitors, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A method for imaging a sample, the method comprising:
   for each of a plurality of positions in a scan pattern and each of a plurality of micro optical elements comprised in a micro optical element array:
   (i) focusing a portion of an illumination beam on or in the sample with the micro optical element,
   (ii) collecting back-emitted light from the sample with the micro optical element, wherein illuminating the sample with the illumination beam causes the sample to emit the back-emitted light,
   (iii) directing the back-emitted light toward a detector array, the detector array comprising detectors, wherein the number of the detectors in the detector array is more than the number of the micro optical elements in the micro optical element array, and
   (iv) receiving, by the detector array, the back-emitted light; and
   laterally moving, by a scanning stage, a position of the micro optical element array relative to the sample and to the detector array along the scan pattern while a position of the sample relative to the detector array remains fixed.

2. The method of claim 1, comprising constructing, by a processor of a computing device, an image based on the back-emitted light received at the detector array from each of the micro optical elements at each position in the scan pattern.

3. The method of claim 2, comprising sending, by the processor, via a network, the image to a second computing device such that the image can be viewed in a remote location.

4. The method of claim 2, wherein (i) an imaging system comprises the micro optical element array and the scanning stage, (ii) the imaging system has a field of view of a size comparable to a size of the micro optical element array, and (iii) the image corresponds in size to the field of view.

5. The method of claim 1, wherein a scan range of the micro optical element array over the scan pattern corresponds to a pitch of the array.

6. The method of claim 1, wherein the sample is freshly resected tissue.

7. The method of claim 1, wherein the method occurs intraoperatively.

8. The method of claim 1, comprising detecting, independently by each of the detectors of the detector array, a portion of the back-emitted light collected by a micro optical element in the micro optical element array.

9. The method of claim 1, comprising directing the illumination with a beam splitter toward the micro optical element array, wherein (iii) directing the back-emitted light toward the detector array comprises passing the back-emitted light through the beam splitter.

10. The method of claim 1, wherein directing the back-emitted light toward the detector comprises rejecting out-of-focus light from reaching the detector.

11. The method of claim 1, comprising expanding, by a beam expander disposed prior to the micro optical element array on an optical path, a waist of the illumination beam to a size comparable to a field of view to be illuminated.

12. The method of claim 1, wherein focusing a portion of the illumination beam on or in the sample with the micro optical element causes the sample to be excited with the portion of the illumination beam such that the sample fluoresces, wherein the back-emitted light collected by each micro optical element in the micro optical element array comprises the fluorescence.

13. The method of claim 1, comprising providing the illumination beam with a laser light source.

14. The method of claim 1, wherein the micro optical element array comprises one or more intermediate areas, wherein each of the one or more intermediate areas is located in between a first micro optical element of the micro optical element array and a second micro optical element array, wherein the one or more intermediate areas is covered with an absorptive and/or reflective layer.

15. The method of claim 1, wherein the micro optical element array comprises from 1,000 to 100,000 micro optical elements.

16. The method of claim 1, wherein each micro optical element of the micro optical element array is a plano-convex-lens with a curved surface facing the sample.

17. The method of claim 1, wherein the scanning stage is a two-axis positioning stage.

18. The method of claim 1, wherein a ratio of the micro optical elements to the detectors is from 1:5 to 1:80.

19. The method of claim 1, wherein the sample disposed on or over a transparent window.

20. The method of claim 1, wherein the plurality of micro optical elements of the micro optical element array focuses onto a focal plane that is located in a range of from 10 μm to 200 μm above the transparent window.

\* \* \* \* \*